US009492525B2

(12) United States Patent
Fattom et al.

(10) Patent No.: US 9,492,525 B2
(45) Date of Patent: Nov. 15, 2016

(54) HUMAN RESPIRATORY SYNCYTIAL VIRUS VACCINE

(75) Inventors: Ali I. Fattom, Ann Arbor, MI (US);
Nicolas Lukacs, Ann Arbor, MI (US);
James R. Baker, Jr., Ann Arbor, MI (US); Vira Bitko, Ann Arbor, MI (US);
Tarek Hamouda, Milan, MI (US)

(73) Assignee: NANOBIO CORPORATION, Ann Arbor, MI (US)

( * ) Notice: Subject to any disclaimer, the term of this patent is extended or adjusted under 35 U.S.C. 154(b) by 604 days.

(21) Appl. No.: 13/543,493

(22) Filed: Jul. 6, 2012

(65) Prior Publication Data

US 2013/0011443 A1   Jan. 10, 2013

Related U.S. Application Data

(60) Provisional application No. 61/504,989, filed on Jul. 6, 2011, provisional application No. 61/548,248, filed on Oct. 18, 2011.

(51) Int. Cl.
| | |
|---|---|
| *A61K 9/107* | (2006.01) |
| *A61P 37/04* | (2006.01) |
| *A61K 39/155* | (2006.01) |
| *A61K 39/12* | (2006.01) |
| *C07K 16/10* | (2006.01) |
| *C12N 7/00* | (2006.01) |
| *A61K 9/00* | (2006.01) |
| *A61K 9/06* | (2006.01) |
| *A61K 9/127* | (2006.01) |
| *A61K 9/51* | (2006.01) |
| *A61K 31/716* | (2006.01) |
| *A61K 31/722* | (2006.01) |
| *A61K 39/00* | (2006.01) |

(52) U.S. Cl.
CPC ............ *A61K 39/12* (2013.01); *A61K 9/0019* (2013.01); *A61K 9/06* (2013.01); *A61K 9/1271* (2013.01); *A61K 9/5115* (2013.01); *A61K 31/716* (2013.01); *A61K 31/722* (2013.01); *C07K 16/1027* (2013.01); *C12N 7/00* (2013.01); *A61K 2039/5252* (2013.01); *A61K 2039/543* (2013.01); *A61K 2039/55555* (2013.01); *A61K 2039/55566* (2013.01); *A61K 2039/55583* (2013.01); *C07K 2317/33* (2013.01); *C07K 2317/76* (2013.01); *C12N 2760/18521* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| | | | |
|---|---|---|---|
| 4,826,687 A | 5/1989 | Nerome et al. | |
| 4,895,452 A | 1/1990 | Yiournas et al. | |
| 5,103,497 A | 4/1992 | Hicks | |
| 5,962,298 A | 10/1999 | Fiers et al. | |
| 6,015,832 A | 1/2000 | Baker, Jr. et al. | |
| 6,077,514 A | 6/2000 | Maassab et al. | |
| 6,194,546 B1 | 2/2001 | Newton et al. | |
| 6,506,803 B1 | 1/2003 | Baker, Jr. et al. | |
| 6,559,189 B2 | 5/2003 | Baker, Jr. et al. | |
| 6,635,676 B2 | 10/2003 | Baker, Jr. et al. | |
| 6,861,244 B2 | 3/2005 | Barrett et al. | |
| 7,192,595 B2 | 3/2007 | Arnon et al. | |
| 7,314,624 B2* | 1/2008 | Baker et al. ............... | 424/192.1 |
| 2004/0043041 A1 | 3/2004 | Baker, Jr. et al. | |
| 2005/0208083 A1 | 9/2005 | Annis | |
| 2006/0251684 A1 | 11/2006 | Annis et al. | |
| 2007/0036831 A1 | 2/2007 | Baker | |
| 2007/0054834 A1 | 3/2007 | Baker | |
| 2008/0248057 A1 | 10/2008 | Cates et al. | |
| 2008/0317799 A1 | 12/2008 | Baker et al. | |
| 2010/0316673 A1 | 12/2010 | Lukacs et al. | |

FOREIGN PATENT DOCUMENTS

| | | |
|---|---|---|
| WO | WO 2010/148111 A1 | 6/2010 |
| WO | WO 2013/006797 A1 | 1/2013 |

OTHER PUBLICATIONS

Herlocher et al. 1999 Vaccine vol. 17, pp. 172-181.*
Bielinska et al., "A Novel, Killed-Virus Nasal Vaccinia Virus Vaccine," *Clin. Vaccine Immunol.*, vol. 15, No. 2, pp. 348-358 (2008).
Bielinska et al., "Mucosal Immunization with a Novel Nanoemulsion-Based Recombinant Anthrax Protective Antigen Vaccine Protects against Bacillus anthracis Spore Challenge," *Infect Immun.*, vol. 75, No. 8, pp. 4020-4029 (2007).
Bielinska et al., "Nasal Immunization with a Recombinant HIV gp120 and Nanoemulsion Adjuvant Produces Th1 Polarized Responses and Neutralizing Antibodies to Primary HIV Type 1 Isolates," *AIDS Research and Human Retroviruses*, vol. 24, No. 2, pp. 271-281 (2008).
Gomez et al., "Phase-I study MEDI-534, of a live attenuated intranasal vaccine against respiratory syncytial virus and parainfluenza-3 virus in seropositive children," *Ped Infect J.*, vol. 28, pp. 655-658 (2009).
Graham, B., "Biological challenges and technological opportunities for respiratory syncytial virus vaccine development," *Immunological Reviews*, vol. 239, pp. 149-166 (2011).
Hacking et al., "Respiratory syncytial virus — virus biology and host response," *J. Infection.*, vol. 45 pp. 18-24 (2002).

(Continued)

*Primary Examiner* — Shanon A Foley
*Assistant Examiner* — Myron Hill
(74) *Attorney, Agent, or Firm* — Foley & Lardner LLP

(57) ABSTRACT

The present invention relates to RSV vaccines and methods for inducing an immune response to RSV in a subject comprising administering an RSV vaccine.

25 Claims, 25 Drawing Sheets

(56) References Cited

OTHER PUBLICATIONS

Figure 1:
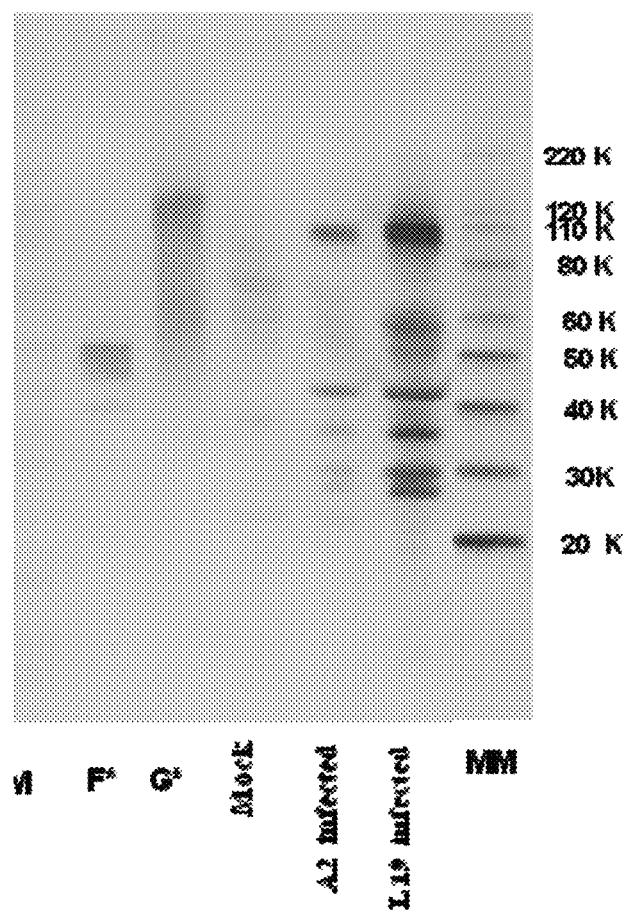

Herlocher et al., "Immunological properties of plaque purified strains of live attenuated respiratory syncytial virus (RSV) for human vaccine," *Vaccine*, vol. 17, No. 2, pp. 172-181 (1999).

Huang et al., "Recombinant respiratory syncytial virus F protein expression is hindered by inefficient nuclear export and mRNA processing," *Virus Genes*, vol. 40, pp. 212-221 (2010).

Kim et al.," Single mucosal immunization of recombinant adenovirus-based vaccine expressing F1 protein fragment induces protective mucosal immunity against respiratory syncytial virus infection," *Vaccine*, vol. 28, pp. 3801-3808 (2010).

Kruijens et al., "Local innate and adaptive immune responses regulate inflammatory cell influx into the lungs after vaccination with formalin inactivated RSV," *Vaccine*, vol. 29, pp. 2730-2741 (2011).

Langley et al., "A dose ranging study of a subunit Respiratory Syncytial Virus subtype A vaccine with and without aluminum phosphate adjuvantation in adults ?65 years of age," *Vaccine*, vol. 27, pp. 5913-5919 2009.

Lukacs et al., "Differential immune responses and pulmonary pathophysiology are induced by two different strains of respiratory syncytial virus," *Am J Pathol*, vol. 169, No. 3, pp. 977-986 (2006).

Makidon et al., "Pre Clinical Evaluation of a Novel Nanoemulsion-Based Hepatitis B Mucosal Vaccine," *PLoS ONE*, vol. 3, No. 8, pp. 2954; 1-15 (2008).

McLellan et al., "Structure of the Respiratory Syncytial Virus Fusion glycoprotein in the post-fusion conformation reveals preservation of neutralizing epitopes," *J Virology*, pp. 7788-7796 (2011).

Myc et al., "Development of immune response that protects mice from viral pneumonitis after a single intranasal immunization with influenza A virus and nanoemulsion," *Vaccine*, vol. 21, pp. 3801-3814 (2003).

Nallet et al., Respiratory Syncytial Virus subunit vaccine based on a recombinant fusion protein expressed transiently in mammalian cells, vol. 27, pp. 6415-6419 (2009).

Singh et al.," Immuogenicity and efficacy of recombinant RSV-F vaccine in a mouse model," *Vaccine*, vol. 25, pp. 6211-6223 (2007).

Swanson et al., "Structural basis for immunization with postfusion respiratory syncytial virus fusion F glycoprotein (RSV F) to elicit high neutralizing antibody titers," *PNAS*, vol. 108, pp. 9619-9624 (2011).

Warren et al., "Pharmacological and Toxicological Studies on Cetylpyridinium Chloride, A New Germicide," *J. Pharmacol. Exp. Ther.*, vol. 74, pp. 401-408 (1942).

Office Action issued in related U.S. Appl. No. 13/608,317, dated Nov. 20, 2014.

Moore, et al., "A Chimeric A2 Strain of Respiratory Syncytial Virus (RSV) with the Fusion Protein of RSV Strain Line 19 Exhibits Enhanced Viral Load, Mucas, and Airway Dysfunction," *Journ. of Virology*, pp. 4185-4194 (2009).

Stokes, et al., "Differential Pathogenesis of Respiratory Syncytial Virus Clinical Isolates in BALB/c Mice," *Journ. of Virology*, pp. 5782-5793 (2011).

Genbank: FJ614813.1, "Respiratory Syncytial Virus Strain 19, Complete Genome," 7 pages (2009).

Office Action issued in related U.S. Appl. No. 13/608,317, dated Jun. 19, 2015.

Lindell, et al., "A Novel Inactivated Intranasal Respiratory Syncytial Virus Vaccine Promotes Viral Clearance without TH2 Associated Vaccine-Enhanced Disease," PLos ONE, vol. 6, No. 7, 14 pages (2011).

McGinnes, et al., "Assembly and Immunological Properties of Newcastle Disease Virus-Like Particles Containing the Respiratory Syncytial Virus F and G Proteins," *Journ. of Viroglogy*, pp. 366-377 (2011).

Passmore et al., "Intranasal immunization with $W_{80}5EC$ adjuvanted recombinant RSV rF-ptn enhances clearance of respiratory syncytial virus in a mouse model," *Human Vaccines & Immunotherapeutics*, vol. 10, No. 3, pp. 615-622 (2014).

European Search Report issued in related European Patent Application No. 12829559, dated Mar. 17, 2015.

Notice of Reasons for Rejection issued in related Japanese Patent Application No. 2014-529937, dated Jun. 7, 2016.

Office Action issued in related U.S. Appl. No. 13/608,317, dated Jun. 28, 2016.

* cited by examiner

\* Recombinant protein
\*\* 7.5 µL virus was loaded in each lane.

HUMAN RESPIRATORY SYNCYTIAL VIRUS VACCINE

CROSS-REFERENCE TO RELATED APPLICATIONS

This present application claims priority of U.S. Provisional Patent Application Nos. 61/504,989, filed Jul. 6, 2011, and 61/548,248, filed Oct. 18, 2011, which are specifically incorporated by reference in their entirety.

FIELD OF THE APPLICATION

The present application relates to the field of immunology, in particular, a vaccine composition of the human respiratory syncytial virus (HRSV) strain, L19 (HRSV-L19) that is a hyperproducer of the structural Fusion (F) and Glycoprotein (G) viral proteins, and the use of HRSV-L19 as a vaccine against HRSV infections. The application further relates to the combination of HRSV-L19 with a nanoemulsion, which is a potent immune enhancer, to induce a protective immune response and avoid vaccine-induce disease enhancement.

BACKGROUND OF THE INVENTION

Respiratory Syncytial Virus (RSV) is a leading cause of serious respiratory disease in young children and the elderly worldwide and there is no vaccine available against this pathogen. Human respiratory syncytial virus (HRSV) infection commonly results in bronchiolitis and is the leading cause for infant hospitalization in the developed countries. In addition, HRSV is increasingly being described as a major pathogen in the elderly, transplant patients, and chronic obstructive pulmonary disease (COPD) patients (ref 1). The development of a safe and immunogenic vaccine to address the infant and elderly population presents a unique opportunity.

Previous methods of viral inactivation for vaccine formulation, such as formaldehyde, resulted in enhanced pulmonary disease and mortality. Extensive research into the development of viral vaccines to address HRSV has met with limited success. Some of the major challenges for HRSV vaccine development include early age of infection, evasion of innate immunity, failure of natural infection to induce immunity that prevent infection, and the demonstration of vaccine-enhance illness (ref 2).

Approaches have included inactivation of viruses with formalin and the demonstration of vaccine-induced enhancement of diseases when infected with HRSV. The observation that formalin inactivated vaccines have shown disease-enhancement, including showing the skewed immune response that is important to prevent enhancement, and priming by mature dendritic cells, are essential for a protective immune response. Moreover, having F protein in its native state to maintain conformational epitopes is essential for the generation of neutralizing antibodies (refs. 3, 4, 5). The uses of live attenuated vaccines have met with limited success, as the vaccines have been shown to be minimally immunogenic (ref 6). The utilization of a recombinant F protein vaccine showed reduced immunogenicity, with the demonstration that the purified F protein is structurally immature and not the appropriate version for eliciting neutralizing antibodies (ref 7, 8). With the use of a subunit vaccine, having an optimal level of F protein is critical for inducing the appropriate immune response, as the subunit vaccines have been hindered by the inefficient and inappropriate expression of F protein (ref 9. 10). The observation that a subunit vaccine containing F protein, even with adjuvant, is not completely protective and optimal (ref 11), suggests that F protein presentation within its native state in the virion is essential for usage as a vaccine.

The biological challenges and safety concerns of development of a HRSV-L19 present a unique opportunity for a safe and durable vaccine against HRSV.

As with most vaccines, greater immunogenicity is also sought as it correlates with greater efficacy in humans. The prior art has typically disclosed the use of recombinant proteins (e.g., U.S. Pat. Nos. 7,192,595; 6,194,546; 5,962,298), as well as the addition of adjuvants such as aluminum (U.S. Pat. No. 6,861,244) and muramyldipeptide (U.S. Pat. No. 4,826,687) to compositions to increase the immunogenicity. However, there still exists a need to develop highly effective RSV vaccines with improved storage stability and ease of administration, which are characteristics of the nanoemulsion vaccines of the present invention.

Prior teachings related to nanoemulsions are described in U.S. Pat. No. 6,015,832, which is directed to methods of inactivating Gram-positive bacteria, a bacterial spore, or Gram-negative bacteria. The methods comprise contacting the Gram-positive bacteria, bacterial spore, or Gram-negative bacteria with a bacteria-inactivating (or bacterial-spore inactivating) emulsion. U.S. Pat. No. 6,506,803 is directed to methods of killing or neutralizing microbial agents (e.g., bacterial, virus, spores, fungus, on or in humans using an emulsion. U.S. Pat. No. 6,559,189 is directed to methods for decontaminating a sample (human, animal, food, medical device, etc.) comprising contacting the sample with a nanoemulsion. The nanoemulsion, when contacted with bacteria, virus, fungi, protozoa or spores, kills or disables the pathogens. The antimicrobial nanoemulsion comprises a quaternary ammonium compound, one of ethanol/glycerol/PEG, and a surfactant. U.S. Pat. No. 6,635,676 is directed to two different compositions and methods of decontaminating samples by treating a sample with either of the compositions. Composition 1 comprises an emulsion that is antimicrobial against bacteria, virus, fungi, protozoa, and spores. The emulsions comprise an oil and a quaternary ammonium compound. U.S. Pat. No. 7,314,624 is directed to methods of inducing an immune response to an immunogen comprising treating a subject via a mucosal surface with a combination of an immunogen and a nanoemulsion. The nanoemulsion comprises oil, ethanol, a surfactant, a quaternary ammonium compound, and distilled water. US-2005-0208083-A1 and US-2006-0251684-A1 are directed to nanoemulsions having droplets with preferred sizes. US-2007-0054834-A1 is directed to compositions comprising quaternary ammonium halides and methods of using the same to treat infectious conditions. The quaternary ammonium compound may be provided as part of an emulsion. Finally, US-2007-0036831-A1 is directed to nanoemulsions comprising an anti-inflammatory agent. However, none of these references teach the methods, compositions and kits of the present invention.

In particular, U.S. Pat. No. 7,314,624 describes nanoemulsion vaccines. However, this reference does not teach the ability to induce a protective immune response to RSV using the immunogen of the invention.

There remains a need in the art for an effective RSV vaccine and methods of making and using the same. The present invention satisfies these needs.

SUMMARY OF THE INVENTION

The present invention provides a novel approach for inducing a protective immune response against HRSV infection by the isolation of a HRSV viral strain which is a hyperproducer of the pivotal immunogenic viral structural proteins, F and G proteins. Having a vaccine candidate that produces higher levels of F protein in its native state within the confines of the normal viral replication cycle is seminal for its usage as an immunogen, as ample amount and proper conformational epitopes will be presented for the generation of neutralizing antibodies and further induction of the protective cellular arm of the immune response.

The inventors have succeeded in cultivating HRSV-L19 and demonstrating that the viral strain is a hyperproducer of F and G viral proteins when compared to the commonly used RSV viral strain A2. The more than 2-fold greater levels of the immunogenic F and G protein found within HRSV-L19 is a novel observation which allows for the use of either attenuated or inactivated virus as a vaccine.

The invention encompasses a vaccine composition comprising a purified respiratory syncytial virus (RSV) strain L19 (RSV-L19). In another embodiment, the RSV-L19 virus is a hyperproducer of Fusion (F) and Glycoprotein (G) structural proteins associated with viral particles. In yet another embodiment, the RSV-L19 virus is attenuated human respiratory syncytial virus (HRSV) strain L19. In one embodiment, the vaccine composition comprises a human respiratory syncytial virus deposited with the American Type Culture Collection (ATCC) as HRSV-L19.

In another embodiment of the invention, there is provided a method for preparing an immunogenic preparation, whereby HRSV-L19 is genetically engineered with attenuating mutations and deletions resulting in an attenuating phenotype. The resulting attenuated virus is cultured in an appropriate cell line and harvested. The harvested virus is then purified free from cellular and serum components. The purified virus is then mixed in an acceptable pharmaceutical carrier for use a vaccine composition. Thus, described are vaccine compositions comprising an RSV viral genome (such as RSV strain L19) comprising at least one attenuating mutation. In yet another embodiment, the vaccine compositions comprise an RSV viral genome (such as RSV strain L19) comprising nucleotide modifications denoting attenuating phenotypes.

In one embodiment, described is a method for enhancing immunity to human respiratory syncytial virus infections comprising administering to a subject a nanoemulsion formulation comprising HRSV-L19. Another embodiment of the invention is directed to a method for inducing an enhanced immunity against disease caused by human respiratory syncytial virus comprising the step of administering to a subject an effective amount of a purified HRSV-L19 vaccine composition. In some embodiments, the subject can produce a protective immune response after at least a single administration of the nanoemulsion vaccine. In addition, the immune response can be protective against one or more strains of RSV. The induction of enhanced immunity to HRSV is dependent upon the presence of optimal levels of antigen. Furthermore, the identification of the critical level of antigen is important for providing a robust immune response. The demonstration that F protein levels are directly correlated with the presence and persistence of neutralizing antibodies and protection against viral challenge, demonstrates that having a viral strain that produces optimal levels of the critical immunogenic F protein expressed in its natural orientation is seminal for usage as a vaccine candidate.

In one embodiment of the invention, there is provided a method for preparing an immunogenic preparation, whereby the viral strain HRSV-L19 is cultured in an appropriate cell line and harvested. The harvested virus is concentrated and purified free from cellular and serum components. In a further embodiment of the invention, the purified HRSV-L19 is then inactivated and adjuvanted with a nanoemulsion formulation to provide a non-infectious and immunogenic virus. The simple mixing of a nanoemulsion with a vaccine candidate has been shown to produce both mucosal and system immune response. The mixing of the RSV virion particles with a nanoemulsion results in discrete antigen particles in the oil core of the droplet. The antigen is incorporated within the core and this allows it to be in a free form which promotes the normal antigen conformation.

In one embodiment of the invention, the RSV vaccines comprise an adjuvant. In another embodiment, the adjuvant is a nanoemulsion. The nanoemulsion can comprise an aqueous phase, at least one oil, at least one surfactant, and at least one solvent.

In one embodiment of the invention, the present invention provides methods, compositions and kits for inducing an immune response to RSV in a subject. The methods comprise administering to a subject a nanoemulsion RSV vaccine, wherein the nanoemulsion RSV vaccine comprises droplets having an average diameter of less than about 1000 nm. The nanoemulsion RSV vaccine can further comprise an aqueous phase, at least one oil, at least one surfactant, at least one organic solvent, at least one RSV immunogen, and optionally at least one chelating agent. In another embodiment, the nanoemulsion RSV vaccine may be administered via any pharmaceutically acceptable method, including but not limited to intranasally. In yet another embodiment of the invention, the nanoemulsion RSV vaccine lacks an organic solvent. Furthermore, additional adjuvants may be added to the nanoemulsion RSV vaccine.

The RSV vaccines may be formulated as a liquid dispersion, gel, aerosol, pulmonary aerosol, nasal aerosol, ointment, cream, or solid dose. In addition, the RSV vaccines may be administered via any pharmaceutically acceptable method, such as parenterally, orally or intranasally. The parenteral administration can be by subcutaneous, intraperitoneal or intramuscular injection.

In another embodiment of the invention, the nanoemulsion and/or nanoemulsion vaccine is not systemically toxic to the subject, produces minimal or no inflammation upon administration, or any combination thereof.

In one embodiment of the invention, the subject undergoes seroconversion after a single administration of the RSV vaccine.

In yet another embodiment of the invention, the nanoemulsion RSV vaccine composition comprises (a) at least one cationic surfactant; (b) a cationic surfactant which is cetylpyridinium chloride; (c) a cationic surfactant, and wherein the concentration of the cationic surfactant is less than about 5.0% and greater than about 0.001%; (d) a cationic surfactant, and wherein the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, less than about 0.10%, greater than about 0.001%, greater than about 0.002%, greater than about 0.003%, greater than about 0.004%, greater than about 0.005%, greater than about 0.006%, greater than about 0.007%, greater than about 0.008%, greater than about 0.009%, and greater than about 0.010%; or (e) any combination thereof.

In another embodiment of the invention, the nanoemulsion RSV vaccine composition comprises (a) at least one cationic surfactant and at least one non-cationic surfactant; (b) at least one cationic surfactant and at least one non-cationic surfactant, wherein the non-cationic surfactant is a nonionic surfactant; (c) at least one cationic surfactant and at least one non-cationic surfactant, wherein the non-cationic surfactant is a polysorbate nonionic surfactant, a poloxamer nonionic surfactant, or a combination thereof; (d) at least one cationic surfactant and at least one nonionic surfactant which is polysorbate 20, polysorbate 80, poloxamer 188, poloxamer 407, or a combination thereof; (e) at least one cationic surfactant and at least one nonionic surfactant which is polysorbate 20, polysorbate 80, poloxamer 188, poloxamer 407, or a combination thereof, and wherein the nonionic surfactant is present at about 0.01% to about 5.0%, or at about 0.1% to about 3%; (e) at least one cationic surfactant and at least one non-cationic surfactant, wherein the non-cationic surfactant is a nonionic surfactant, and the non-ionic surfactant is present in a concentration of about 0.05% to about 10%, about 0.05% to about 7.0%, about 0.1% to about 7%, or about 0.5% to about 4%; (f) at least one cationic surfactant and at least one a nonionic surfactant, wherein the cationic surfactant is present in a concentration of about 0.05% to about 2% or about 0.01% to about 2%; or (g) any combination thereof.

In yet another embodiment of the invention, the RSV vaccines comprise low molecular weight chitosan, medium molecular weight chitosan, high molecular weight chitosan, a glucan, or any combination thereof. The low molecular weight chitosan, median molecular weight chitosan, high molecular weight chitosan, a glucan, or any combination thereof can be present in the nanoemulsion.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

DESCRIPTION OF THE FIGURES

FIG. 1: Shows an SDS PAGE of HRSV Infected Cell Lysate (SDS treated) with L19 and A2.

FIG. 2: Shows an SDS-PAGE of RSV strain L19 and RSV strain A2 HRSV Cell Lysate (cells & supernatant).

FIG. 3: Shows an SDS PAGE of HRSV strain L19 and strain A2 Purified Virus.

FIG. 4: Shows a Western blot of HRSV strain L19 and strain A2 F and G Protein expression 24 hours after Virus Infection.

FIG. 5: Shows a Western Blot of HRSV strain L19 and strain A2 F and G Protein expression 4 days after Virus Infection.

FIG. 6: Shows TEM cross section images of the 20% $W_{80}$5EC nanoemulsion with and without 30 μg total HA. FIG. 6A shows a 20% nanoemulsion without added antigen. FIG. 6B (panel on the right) shows a 20% nanoemulsion combined with 30 μg Fluzone®, and illustrates that the HA antigens are located in the oil droplets. The darkly stained antigens are located outside of the nanoemulsion particles.

FIG. 7: Shows the viral inactivation by Western blot assessment, with lanes containing: (1) $W_{80}$5EC (Lane 1), (2) $W_{80}$5EC+0.03% B 1,3 Glucan (lane 2), (3) $W_{80}$5EC+0.3% Chitosan (medium molecular weight)+acetic acid (lane 3), (4) $W_{80}$5EC+0.3% P407 (lane 4), (5) $W_{80}$5EC+0.3% Chitosan (low molecular weight)+0.1% acetic acid (lane 5), (6) media alone (lane 6); (7) βPL-inactivated virus (lane 7), and (8) L19 positive control (lane 9).

FIG. 8: Shows Western blot analysis performed with anti-RSV antibody (anti-G); L19 virus $4\times10^6$ PFU/lane, $2\times10^6$ PFU/lane, and $1\times10^6$ PFU/lane+/−βPL inactivation combined with $W_{80}$5EC as indicated. Specimens were analyzed fresh (FIG. 8A) or after 14 days at 4° C. or room temperature (RT) (FIG. 8B). MM=Molecular weight.

FIG. 9: Shows the immune response (IgG, μg/ml) at week 3 following vaccination in mice vaccinated IM with different nanoemulsion formulations with and without chitosan: (1) RSV strain L19+2.5% $W_{80}$5EC+0.1% Low Mol. Wt. Chitosan; (2) RSV strain L19+5% $W_{80}$5EC; (3) RSV strain L19+2.5% $W_{80}$5EC; (4) RSV strain L19+βPL inactivated virus; and (5) naive mice (no vaccine).

FIG. 10: Shows a vaccination schedule for an evaluation of two nanoemulsion-adjuvanted vaccines in cotton rats (Example 10). The two formulations evaluated include the $W_{80}$5EC and the $W_{80}P_{188}$5EC (1:1:5) (see Tables 10 and 11 below). Cotton rats received two doses of 30 μl IN of the nanoemulsion-adjuvanted vaccine containing 6.6 μg F-ptn. They were challenged with $5\times10^5$ pfu RSV strain A2 at week 23. Half of the animals were sacrificed at day 4 and half were sacrificed on day 8.

FIG. 11: Shows the results of an immunogenicity study of $W_{80}$P1885EC nanoemulsion inactivated RSV vaccine in cotton rats. In the left panel, the Y axis shows the end point titers of specific antibody to F protein and the X axis shows the time period in weeks. In the right panel the Y-axis shows the serum antibody levels in μg/ml and the X-axis shows the time period in weeks. D4 and D8 show the antibody level in the sera after the challenge.

FIG. 12: Shows the results of an immunogenicity study of $W_{805}$EC nanoemulsion inactivated RSV vaccine in cotton rats. The Y axis shows the end point titers of specific antibody to F protein and the X axis shows the time period in weeks.

FIG. 13: Shows the immunogenicity of RSV neutralization in cotton rats. Cotton rats were vaccinated with 30 μl of vaccine intranasally, boosted at 4 weeks, and bled at weeks 0, 4, 6, and 8. Study groups included two groups that received 20% $W_{80}$5EC nanoemulsion mixed with either $1.6\times10^5$ PFU RSV strain L19 containing 3.3 μg F protein (n=8) or $3.2\times10^5$ PFU RSV strain L19 containing 6.6 μg F protein (n=8), as well as two groups that received 20% $W_{80}P_{188}$5EC nanoemulsion mixed with either $1.6\times10^5$ PFU RSV strain L19 containing 3.3 μg F protein (n=8) or $3.2\times10^5$ PFU RSV strain L19 containing 6.6 μg F protein (n=8). Neutralization units (NEU) represent a reciprocal of the highest dilution that resulted in 50% plaque reduction. NEU measurements were performed at 4 weeks (pre boost) and at 6 weeks (2 weeks post boost). Specimens obtained at 6 weeks generated humoral immune responses adequate to allow for NEU analysis. Data is presented as geometric mean with 95% confidence interval (CI) (FIG. 13A). Correlation between EU and NEU is for all animals at 6 weeks using Spearman rho FIG. 14: Shows neutralizing antibodies on day 4 and day 8. FIG. 14A shows the results for $W_{80}P_{188}$5EC nanoemulsion combined with RSV strain L19, and FIG. 14B shows the results for $W_{80}$5EC nanoemulsion combined with RSV strain L19. All cotton rats demonstrated high neutralizing antibodies (NU) against the vaccine RSV strain L19. Neutralizing antibodies were rising steadily following the challenge (Y axis). Day 8 neutralizing units (NU) were higher than Day 4 NU. Naïve Cotton Rats did not show any neutralization activity in their sera.

Figures 15, 15A, 15B:
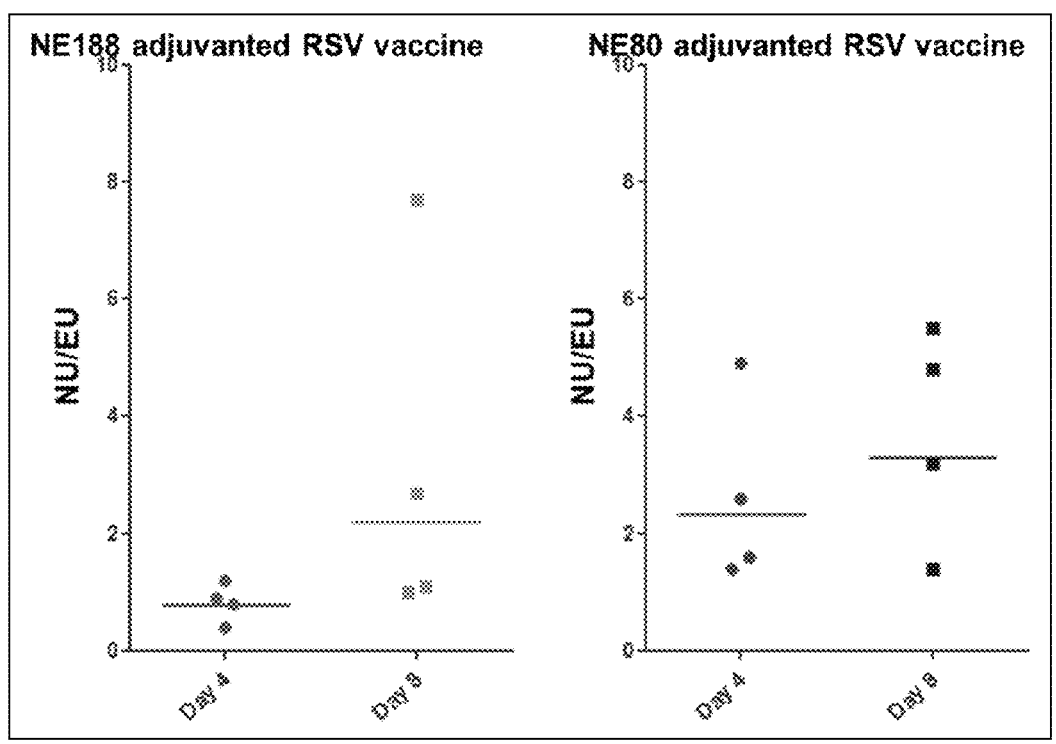

FIG. 15: Shows the Specific activity of serum antibodies showed that the specific activity (Neutralizing units/ELISA units) of the serum antibodies tends to increase on Day 8 when compared to Day 4 post-challenge. FIG. 15A shows the results for $W_{80}P_{188}5EC$ nanoemulsion combined with RSV strain L19 (NU/EU for the Y axis), at Day 4 and Day 8. FIG. 15B shows the results for $W_{80}5EC$ nanoemulsion combined with RSV strain L19 (NU/EU for the Y axis), at Day 4 and Day 8.

Figure 16:
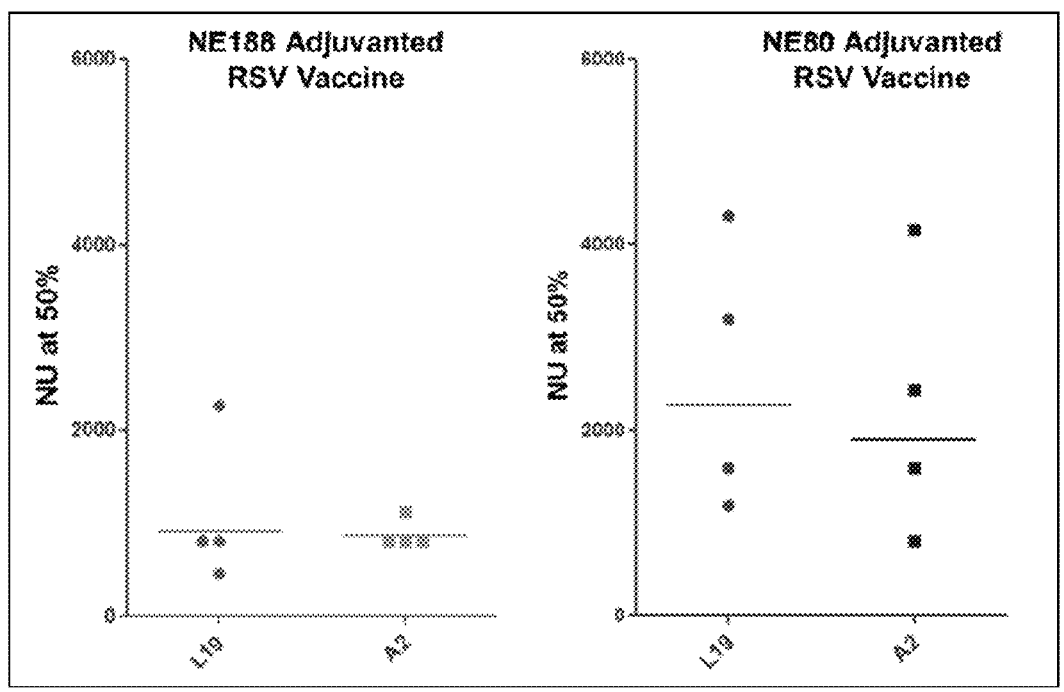

FIG. 16: Shows cross protection at Day 4 for cotton rats that received 3 doses of RSV L19 adjuvanted vaccine, then challenged with RSV strain A2. FIG. 16A shows the results for $W_{80}P_{188}5EC$ nanoemulsion combined with RSV strain L19, and FIG. 16B shows the results for $W_{80}5EC$ nanoemulsion combined with RSV strain L19. Serum neutralization activity shows equivalent NU against RSV strain L19 or RSV strain A2, demonstrating cross protection between the two RSV strains.

Figure 17:
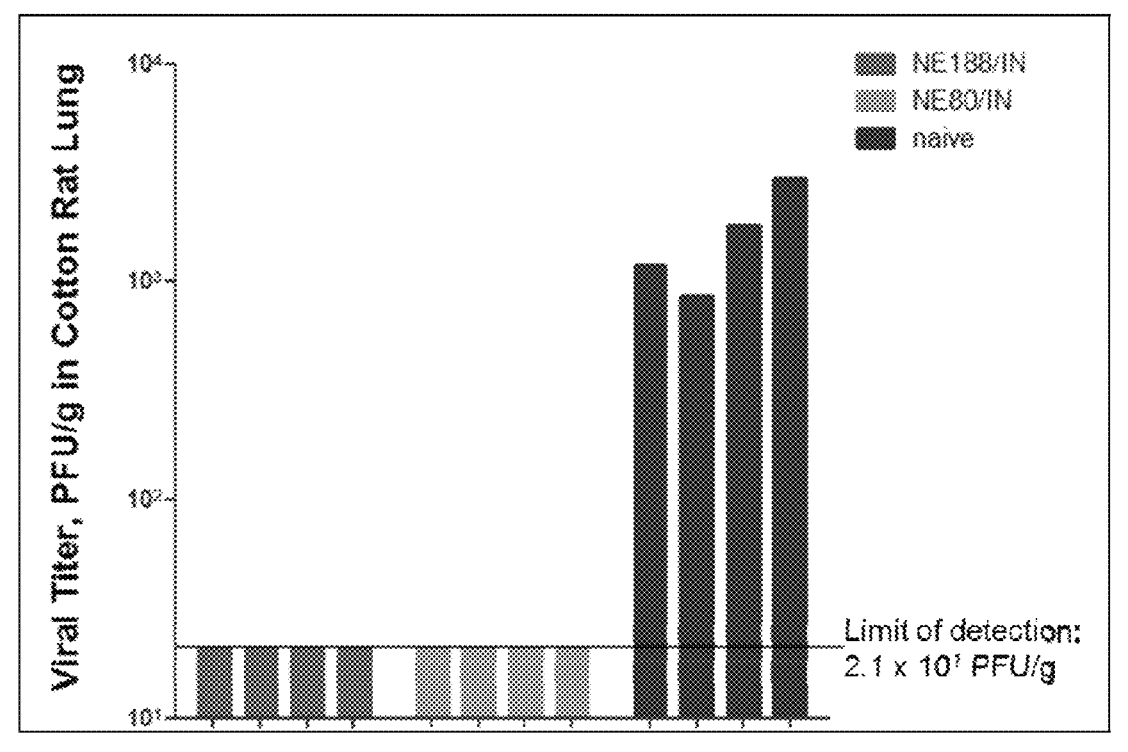

FIG. 17: Shows viral clearance (RSV strain A2) at Day 4 in lungs of Cotton Rats. Vaccinated cotton rats (vaccinated with $W_{80}P_{188}5EC$ nanoemulsion combined with RSV strain L19, or $W_{80}5EC$ nanoemulsion combined with RSV strain L19) showed complete clearance of RSV strain A2 challenged virus from the lungs of cotton rats. Naïve animals were showing >$10^3$ pfu RSV strain A2/gram of lung.

Figure 18:
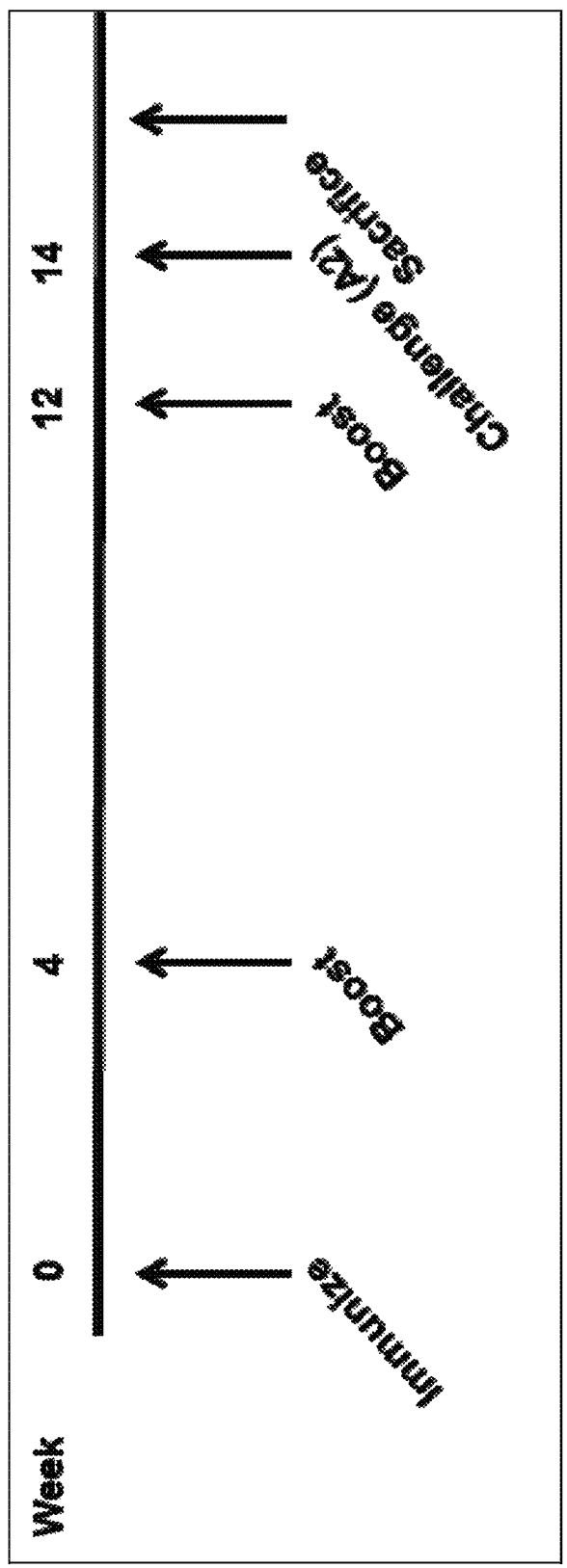

FIG. 18: Shows IM Cotton rat vaccination and challenge schedule.

Figure 19:
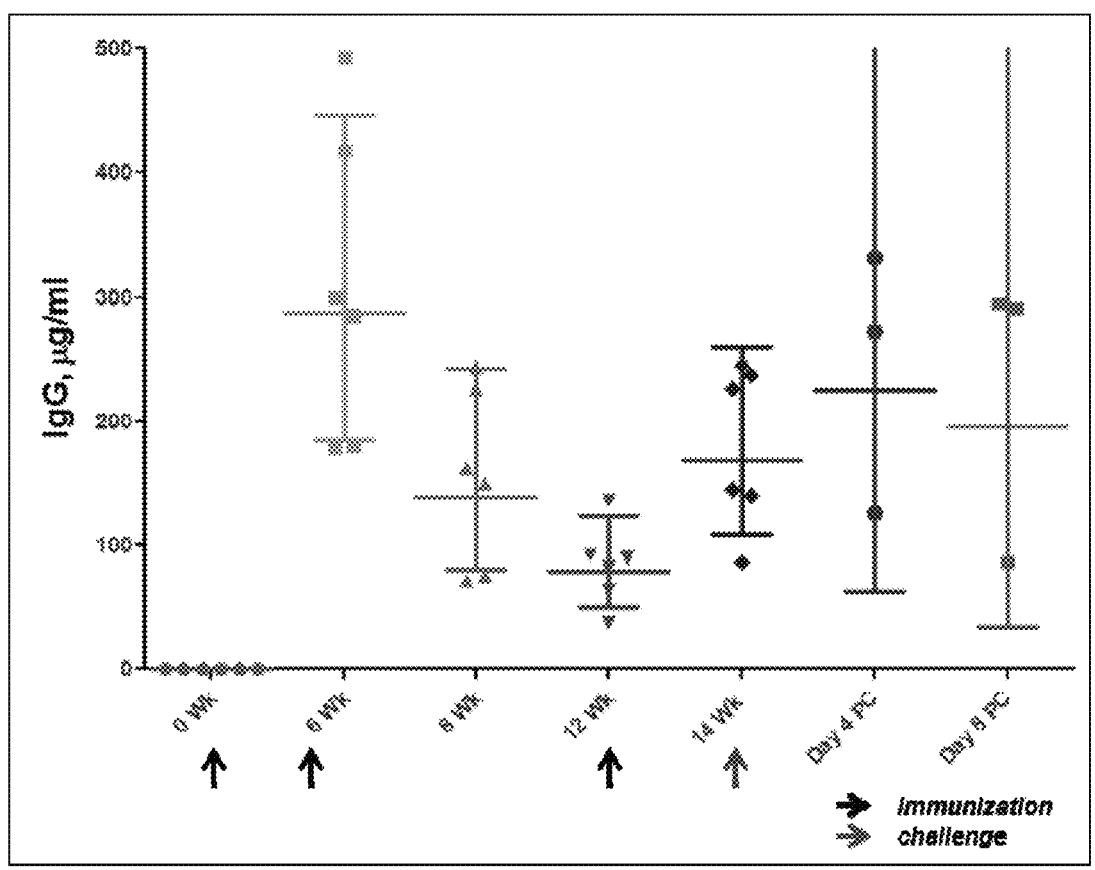
Figure 20:
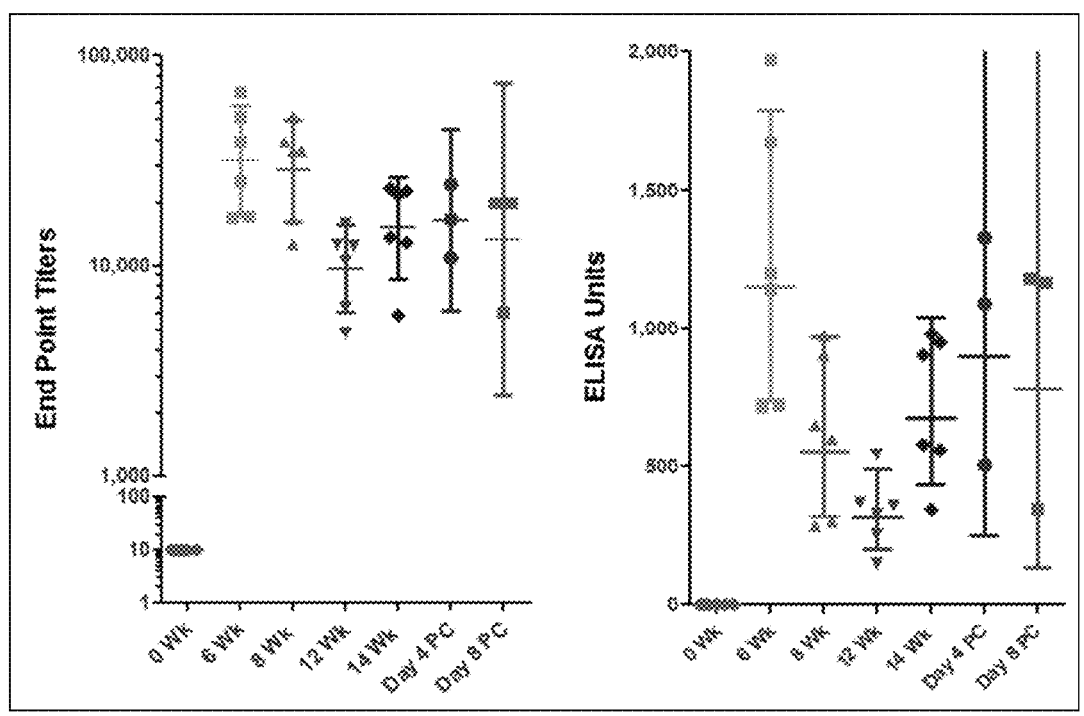

FIG. 19: Shows Serum immune response in cotton rats vaccinated IM with 20% $W_{80}5EC$ nanoemulsion mixed with $1.6 \times 10^5$ PFU RSV strain L19 containing 3.3 µg F protein. The Y axis shows serum IgG, µg/mL, over a 14 week period, at day 4 post-challenge, and at day 8 post-challenge FIG. 20: Shows Serum immune response in cotton rats vaccinated IM with 20% $W_{80}5EC$ nanoemulsion mixed with $1.6 \times 10^5$ PFU RSV strain L19 containing 3.3 µg F protein. FIG. 20A shows the end point titers (Y axis) over a 14 week period, at day 4 post-challenge, and at day 8 post-challenge. FIG. 20B shows the ELISA units (Y axis) over a 14 week period, at day 4 post-challenge, and at day 8 post-challenge.

Figure 21:
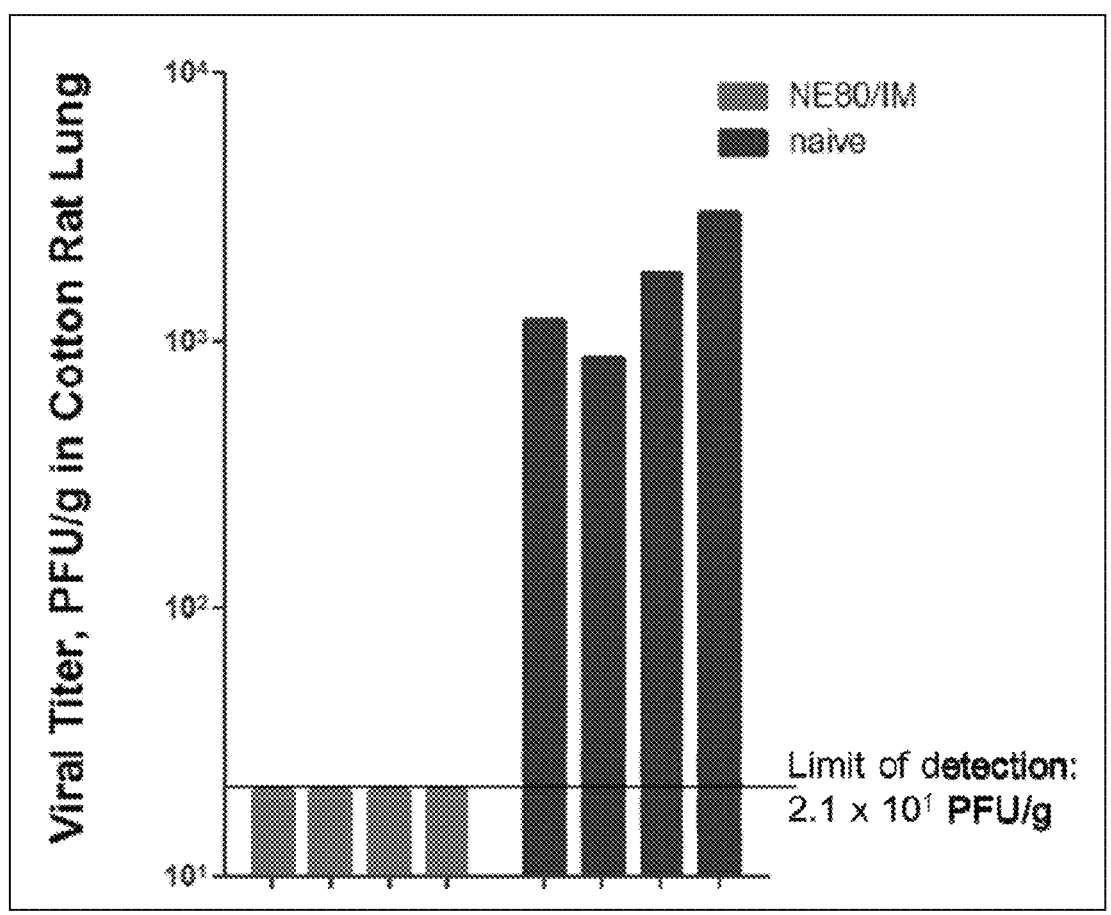

FIG. 21: Shows IM vaccinated cotton rats showed complete clearance of the RSV 4 days following the challenge compared to Naïve animals. Shows viral clearance (RSV strain A2) at Day 4 in lungs of Cotton Rats. IM vaccinated cotton rats (vaccinated with $W_{80}5EC$ nanoemulsion combined with RSV strain L19) showed complete clearance of RSV strain A2 challenged virus from the lungs of cotton rats. Naïve animals were showing $10^3$ pfu RSV strain A2 or greater/gram of lung.

Figure 22:
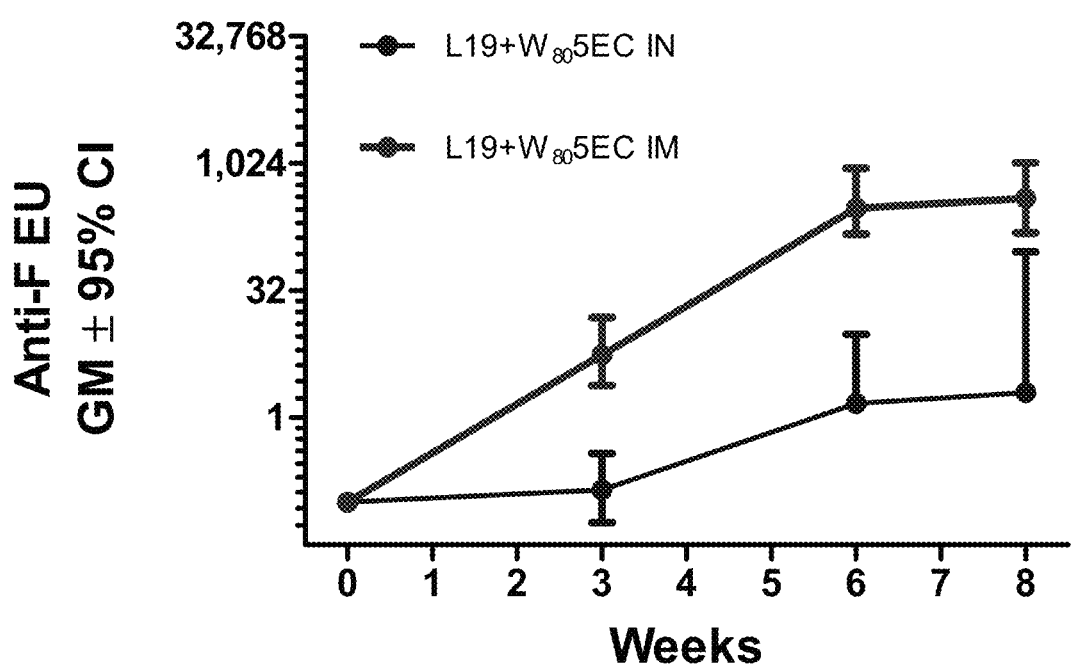

FIG. 22: Shows the measurement of anti-F antibodies (Y axis) over an 8 week period (X axis) for mice vaccinated either IM or IN with RSV vaccine containing $2 \times 10^5$ plaque forming units (PFU) of L19 RSV virus with 1.7 µg of F protein inactivated with 20% $W_{80}5EC$ nanoemulsion adjuvant. BALB/C mice (n=10/arm) were vaccinated at weeks 0 and 4 IN or IM. Serum was analyzed for anti-F antibodies.

Figure 23:
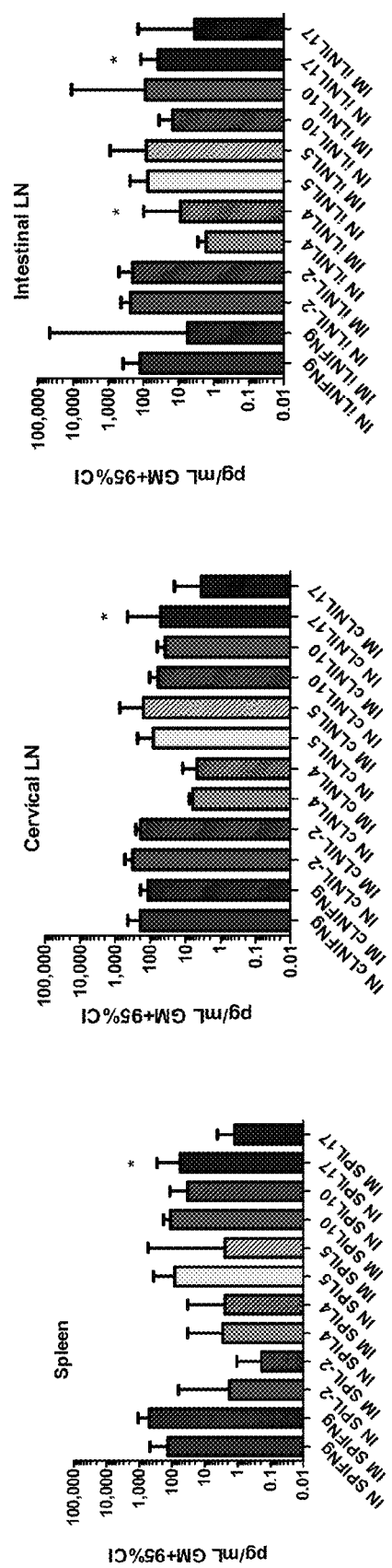

FIG. 23: Shows the measurement of RSV-specific cytokines. Cytokines were measured in cells from spleens, cervical and intestinal lymph nodes (LN) following vaccination of BALB/C mice (n=10/arm) at weeks 0 and 4 IN or IM with RSV vaccine containing $2 \times 10^5$ plaque forming units (PFU) of L19 RSV virus with 1.7 µg of F protein inactivated with 20% $W_{80}5EC$ nanoemulsion adjuvant. Cytokines measured included IFNg, IL-2, IL-4, IL-5, IL-10, and IL-17.

Figure 24:
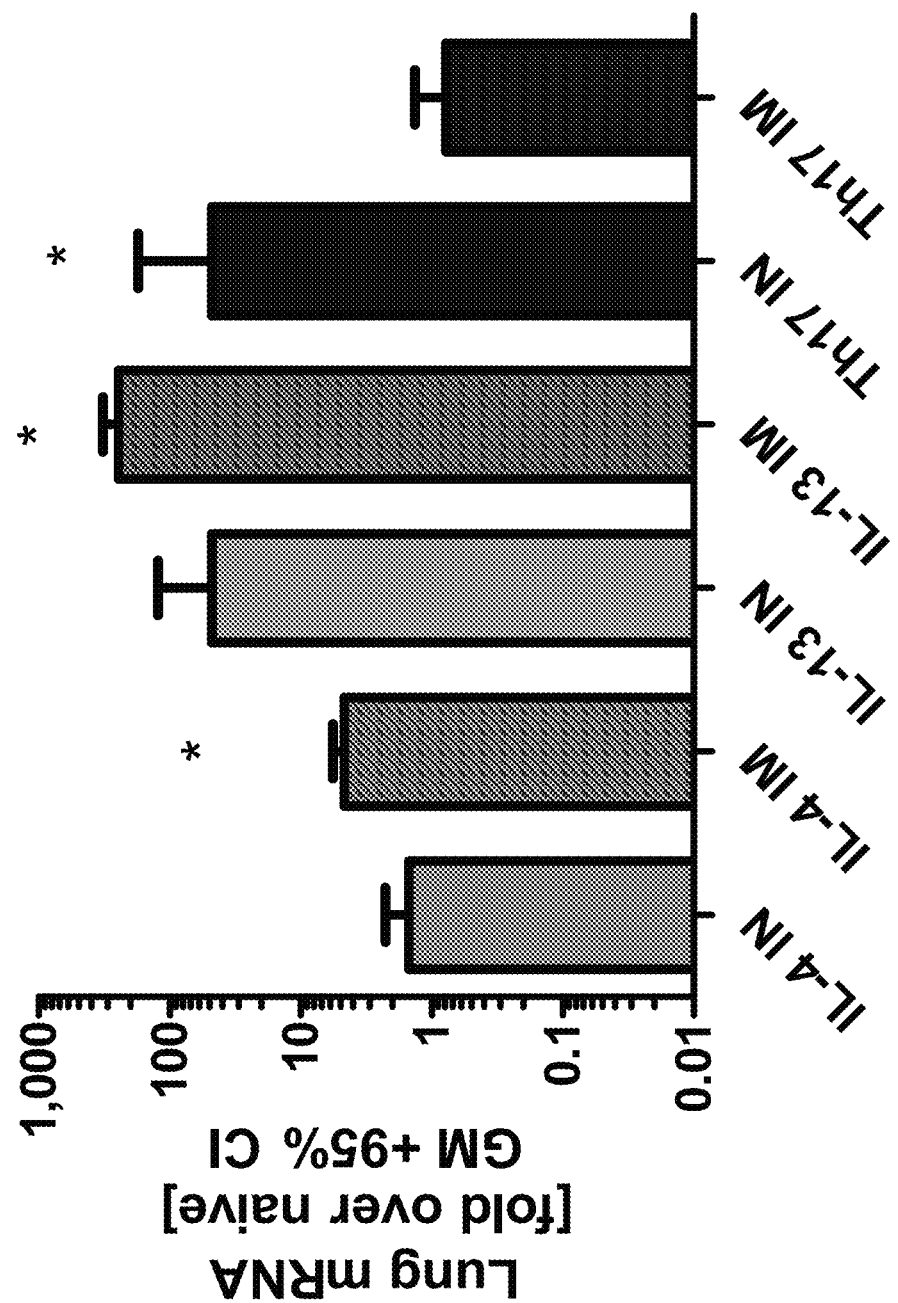

FIG. 24: Shows measurement of the cytokines IL-4, IL-13, and IL-17 in lung tissue following either IN or IM vaccination of BALB/C mice (n=10/arm) at weeks 0 and 4 IN or IM with RSV vaccine containing $2 \times 10^5$ plaque forming units (PFU) of L19 RSV virus with 1.7 µg of F protein inactivated with 20% $W_{80}5EC$ nanoemulsion adjuvant. IL-4 and IL-13 showing greater expression following IM administration, with IL-17 showing greater expression following IN administration.

Figure 25:
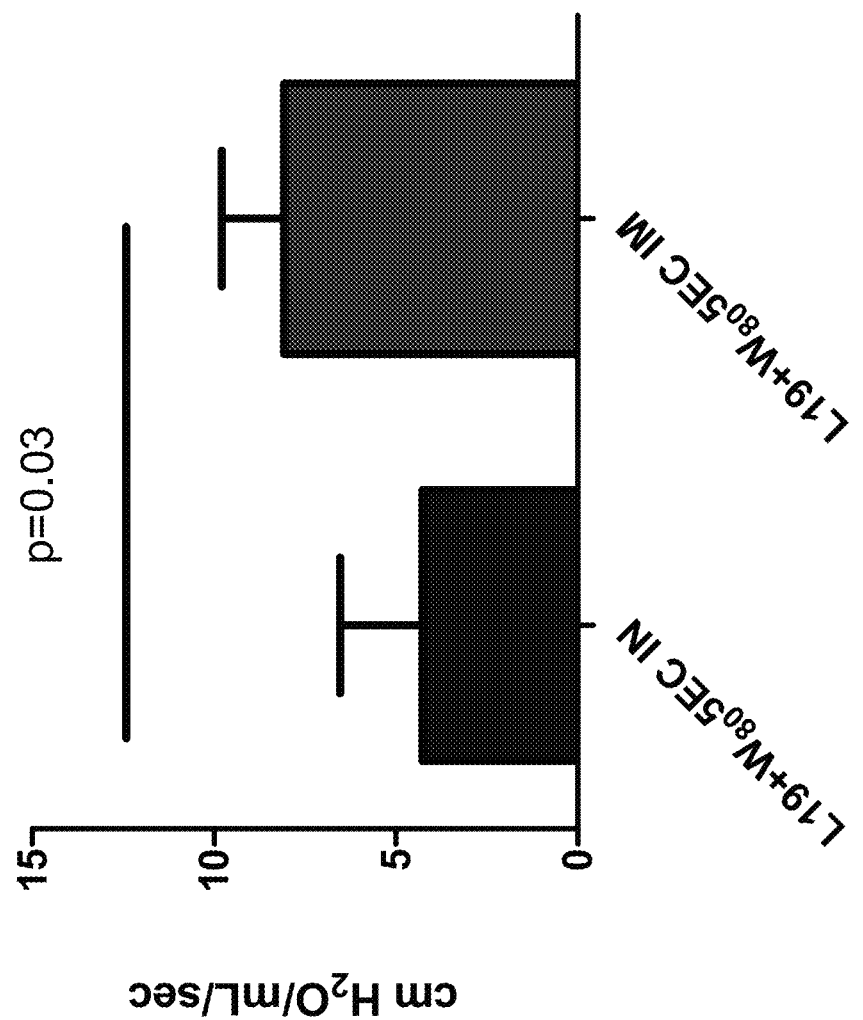

FIG. 25: Shows the measurement of airway resistance (cm $H_2O$/mL/sec) in mice following either IN or IM vaccination of BALB/C mice (n=10/arm) at weeks 0 and 4 IN or IM with RSV vaccine containing $2 \times 10^5$ plaque forming units (PFU) of L19 RSV virus with 1.7 µg of F protein

DETAILED DESCRIPTION OF THE INVENTION

The present invention provides methods, compositions and kits for the stimulation of an immune response to an RSV immunogen. The present inventors surprisingly discovered that cells infected with RSV L19 virus produce between 3-11 fold higher quantities of RSV viral proteins as compared to cells infected with RSV A2 virus (see Example 1, infra.). In one embodiment of the invention, the RSV antigen present in the vaccines of the invention is RSV L19 virus, and more preferably human RSV L19 virus, including the purified, attenuated human respiratory syncytial virus (HRSV) strain L19 (HRSV-L19). In yet other embodiments of the invention, the HSV viral genome can comprise at least one attenuating mutation, including but not limited to nucleotide modifications denoting attenuating phenotypes.

RSV L19 strain was found to cause infection and enhanced respiratory disease (ERD) in mice. Moreover, data published showed that it conferred protection without induction of ERD in mice when formulated with nanoemulsion.

The RSV Strain L19 isolate was isolated from an RSV-infected infant with respiratory illness in Ann Arbor, Mich. on 3 Jan. 1967 in WI-38 cells and passaged in SPAFAS primary chick kidney cells followed by passage in SPAFAS primary chick lung cells prior to transfer to MRC-5 cells (Herlocher 1999) and subsequently Hep2 cells (Lukacs 2006). Comparison of RSV L19 genome (15,191-nt; GenBank accession number FJ614813) with the RSV strain A2 (15,222-nt; GenBank accession number M74568) shows that 98% of the genomes are identical. See Example 5. Most coding differences between L19 and A2 are in the F and G genes. Amino acid alignment of the two strains showed that F protein has 14 (97% identical) and G protein has 20 (93% identical) amino acid differences.

RSV L19 strain has been demonstrated in animal models to mimic human infection by stimulating mucus production and significant induction of IL-13 using an inoculum of $1 \times 10^5$ plaque forming units (PFU)/mouse by intra-tracheal administration (Lukacs 2006).

Rationale for Selection of RSV L19 Strain: NanoBio developed and optimized RSV propagation and purification methods for three viral strains grown in Vero cells and has established multiplicity of Infection (MOI), optimized purification and concentration of the antigen using PEG6000 precipitation and ultracentrifugation. Importantly and uniquely, the RSV L19 viral strain is unique in that it produces significantly higher yields of F protein (approximately 10-30 fold more per PFU) than the other strains. F protein content may be a key factor in immunogenicity and the L19 strain currently elicits the most robust immune response. The L19 strain has a shorter propagation time and therefore will be more efficient from a manufacturing perspective. The results comparing the three viral strains are provided in Table 11, Example 6.

Most significantly, as detailed in Examples 11 and 12 below, all RSV vaccines formulated in nanoemulsion and administered intranasally (IN) or intramuscularly (IM) elicited a protective immune response that prevented infection of immunized animals. Moreover, nanoemulsion-inactivated and adjuvanted RSV L19 vaccines are highly immunogenic in the universally accepted cotton rat model. Cotton rats elicited a rise in antibody titers after one immunization and a significant boost after the second immunization (approximately a 10-fold increase). The antibodies generated are highly effective in neutralizing live virus and there is a linear relationship between neutralization and antibody titers. Furthermore, antibodies generated in cotton rats showed cross protection when immunized with the RSV L19 strain and challenged with the RSV A2 strain. Both IM and IN immunization established memory that can be invoked or recalled after an exposure to antigen either as a second boost or exposure to live virus.

The methods comprise administering to a subject a nanoemulsion RSV vaccine, wherein the nanoemulsion vaccine comprises droplets having an average diameter of less than about 1000 nm. The nanoemulsion RSV vaccine further comprises (a) an aqueous phase, (b) at least one oil, (c) at least one surfactant, (d) at least one organic solvent, (e) at least one RSV antigen, and (f) optionally comprising at least one chelating agent, or any combination thereof. In another embodiment of the invention, the nanoemulsion lacks an organic solvent.

In one embodiment, the subject is selected from adults, elderly subjects, juvenile subjects, infants, high risk subjects, pregnant women, and immunocompromised subjects. In another embodiment, the nanoemulsion RSV vaccine may be administered intranasally.

The nanoemulsion compositions of the invention function as a vaccine adjuvant. Adjuvants serve to: (1) bring the antigen—the substance that stimulates the specific protective immune response—into contact with the immune system and influence the type of immunity produced, as well as the quality of the immune response (magnitude or duration); (2) decrease the toxicity of certain antigens; (3) reduce the amount of antigen needed for a protective response; (4) reduce the number of doses required for protection; (5) enhance immunity in poorly responding subsets of the population and/or (7) provide solubility to some vaccines components. The nanoemulsion vaccine adjuvants are particularly useful for adjuvanting RSV vaccines.

In one embodiment of the invention, the RSV vaccines comprise F protein of an RSV strain, such as but not limited to F protein of RSV strain L19. In another embodiment, the RSV vaccines comprise about 0.1 μg up to about 100 μg, and any amount in-between, of RSV F protein, such as F protein of RSV strain L19. For example, the RSV vaccines can comprise about 0.1 μg, about 0.2 μg, about 0.3 μg, about 0.4 μg, about 0.5 μg, about 0.6 μg, about 0.7 μg, about 0.8 μg, about 0.9 μg, about 1.0 μg, about 1.1 μg, about 1.2 μg, about 1.3 μg, about 1.4 μg, about 1.5 μg, about 1.6 μg, about 1.7 μg, about 1.8 μg, about 1.9 μg, about 2.0 μg, about 2.1 μg, about 2.2 μg, about 2.3 μg, about 2.4 μg, about 2.5 μg, about 2.6 μg, about 2.7 μg, about 2.8 μg, about 2.9 μg, about 3.0 μg, about 3.1 μg, about 3.2 μg, about 3.3 μg, about 3.4 μg, about 3.5 μg, about 3.6 μg, about 3.7 μg, about 3.8 μg, about 3.9 μg, about 4.0 μg, about 4.1 μg, about 4.2 μg, about 4.3 μg, about 4.4 μg, about 4.5 μg, about 4.6 μg, about 4.7 μg, about 4.8 μg, about 4.9 μg, about 5.0 μg, about 5.1 μg, about 5.2 μg, about 5.3 μg, about 5.4 μg, about 5.5 μg, about 5.6 μg, about 5.7 μg, about 5.8 μg, about 5.9 μg, about 6.0 μg, about 6.1 μg, about 6.2 μg, about 6.3 μg, about 6.4 μg, about 6.5 μg, about 6.6 μg, about 6.7 μg, about 6.8 μg, about 6.9 μg, about 7.0 μg, about 7.5 μg, about 8.0 μg, about 8.5 μg, about 9.0 μg, about 9.5 μg, about 10.0 μg, about 10.5 μg, about 11.0 μg, about 11.5 μg, about 12.0 μg, about 12.5 μg, about 13.0 μg, about 13.5 μg, about 14.0 μg, about 14.5 μg, about 15.0 μg, about 15.5 μg, about 16.0 μg, about 16.5 μg, about 17.0 μg, about 17.5 μg, about 18.0 μg, about 18.5 μg, about 19.0 μg, about 19.5 μg, about 20.0 μg, about 21.0 μg, about 22.0 μg, about 23.0 μg, about 24.0 μg, about 25.0 μg, about 26.0 μg, about 27.0 μg, about 28.0 μg, about 29.0 μg, about 30.0 μg, about 35.0 μg, about 40.0 μg, about 45.0 μg, about 50.0 μg, about 55.0 μg, about 60.0 μg, about 65.0 μg, about 70.0 μg, about 75.0 μg, about 80.0 μg, about 85.0 μg, about 90.0 μg, about 95.0 μg, or about 100.0 μg of RSV F protein, such as F protein of RSV strain L19.

In another embodiment of the invention, the RSV vaccines of the invention comprise about $1.0\times10^5$ pfu (plaque forming units (pfu) up to about $1.0\times10^8$ pfu, and any amount in-between, of an RSV virus, such as RSV strain L19. The RSV virus in inactivated by the presence of the nanoemulsion adjuvant. For example, the RSV vaccines can comprise about $1.0\times10^5$, $1.1\times10^5$, $1.2\times10^5$, $1.3\times10^5$, $1.4\times10^5$, $1.5\times10^5$, $1.6\times10^5$, $1.7\times10^5$, $1.8\times10^5$, $1.9\times10^5$, $2.0\times10^5$, $2.1\times10^5$, $2.2\times10^5$, $2.3\times10^5$, $2.4\times10^5$, $2.5\times10^5$, $2.6\times10^5$, $2.7\times10^5$, $2.8\times10^5$, $2.9\times10^5$, $3.0\times10^5$, $3.1\times10^5$, $3.2\times10^5$, $3.3\times10^5$, $3.4\times10^5$, $3.5\times10^5$, $3.6\times10^5$, $3.7\times10^5$, $3.8\times10^5$, $3.9\times10^5$, $4.0\times10^5$, $4.1\times10^5$, $4.2\times10^5$, $4.3\times10^5$, $4.4\times10^5$, $4.5\times10^5$, $4.6\times10^5$, $4.7\times10^5$, $4.8\times10^5$, $4.9\times10^5$, $5.0\times10^5$, $5.5\times10^5$, $6.0\times10^5$, $6.5\times10^5$, $7.0\times10^5$, $7.5\times10^5$, $8.0\times10^5$, $8.5\times10^5$, $9.0\times10^5$, $9.5\times10^5$, $1.0\times10^6$, $1.5\times10^6$, $2.0\times10^6$, $2.5\times10^6$, $3.0\times10^6$, $3.5\times10^6$, $4.0\times10^6$, $4.5\times10^6$, $5.0\times10^6$, $5.5\times10^6$, $6.0\times10^6$, $6.5\times10^6$, $7.0\times10^6$, $7.5\times10^6$, $8.0\times10^6$, $8.5\times10^6$, $9.0\times10^6$, $9.5\times10^6$, $1.0\times10^7$, $1.5\times10^7$, $2.0\times10^7$, $2.5\times10^7$, $3.0\times10^7$, $3.5\times10^7$, $4.0\times10^7$, $4.5\times10^7$, $5.0\times10^7$, $5.5\times10^7$, $6.0\times10^7$, $6.5\times10^7$, $7.0\times10^7$, $7.5\times10^7$, $8.0\times10^7$, $8.5\times10^7$, $9.0\times10^7$, $9.5\times10^7$, $1.0\times10^8$ pfu of an RSV virus, such as RSV strain L19.

In another embodiment of the invention, the RSV vaccines of the invention comprising RSV strain L19 are cross-reactive against at least one other RSV strain (or cross-reactive against one or more RSV strains). As it is known to one of ordinary skill in the art, cross reactivity can be measured 1) using ELISA method to see if the sera from vaccinated animals or individuals will produce antibodies against strains that were not used in the administered vaccine; 2) Immune cells will produce cytokines when stimulated in vitro using stains that were not used in the administered vaccine. Cross protection can be measured in vitro when antibodies in sera of animals vaccinated with one strain will neutralize infectivity of another virus not used in the administered vaccine.

For example, the RSV vaccines of the invention comprising RSV strain L19 can be cross reactive against one or more RSV strains selected from the group consisting of RSV strain A2 (wild type) (ATCC VR-1540P), RSV strain rA2cp248/404, RSV Strain 2-20, RSV strain 3-12, RSV strain 58-104, RSV strain Long (ATCC VR-26), RSV strain 9320 (ATCC VR-955), RSV strain B WV/14617/85 (ATCC VR-1400), RSV strain 18537 (ATCC VR-1580), RSV strain A2 cpts-248 (ATCC VR-2450), RSV strain A2 cpts-530/1009 (ATCC VR-2451), RSV strain A2 cpts-530 (ATCC VR-2452), RSV strain A2 cpts-248/955 (ATCC VR-2453), RSV strain A2 cpts-248/404 (ATCC VR-2454), RSV strain A2 cpts-530/1030 (ATCC VR-2455), RSV strain subgroup B cp23 Clone 1A2 (ATCC VR-2579), RSV strain Subgroup B, Strain B1, and cp52 Clone 2B5 (ATCC VR-2542).

In another embodiment of the invention, the RSV vaccines of the invention result in a protective immune response following one or two doses of the RSV vaccine.

In another embodiment of the invention, the RSV vaccines of the invention result in generation of robust neutralizing antibodies. For example, Administration of one or two doses of an RSV vaccine according to the invention can result in neutralizing antibody titers ranging from 2 to $10^6$ or more.

Nanoemulsions are oil-in-water emulsions composed of nanometer sized droplets with surfactant(s) at the oil-water interface. Because of their size, the nanoemulsion droplets are pinocytosed by dendritic cells triggering cell maturation and efficient antigen presentation to the immune system. When mixed with different antigens, nanoemulsion adjuvants elicit and up-modulate strong humoral and cellular $T_H1$-type responses as well as mucosal immunity (Makidon et al., "Pre-Clinical Evaluation of a Novel Nanoemulsion-Based Hepatitis B Mucosal Vaccine," PLoS ONE. 3(8): 2954; 1-15 (2008); Hamouda et al., "A Novel Nanoemulsion Adjuvant Enhancing The Immune Response from Intranasal Influenza Vaccine in Mice in National Foundation for Infectious Disease," 11th Annual Conference on Vaccine Research. Baltimore, Md. (2008); Myc et al., "Development of immune response that protects mice from viral pneumonitis after a single intranasal immunization with influenza A virus and nanoemulsion," Vaccine, 21(25-26):3801-14 (2003); Bielinska et al., "Mucosal Immunization with a Novel Nanoemulsion-Based Recombinant Anthrax Protective Antigen Vaccine Protects against *Bacillus anthracis* Spore Challenge," *Infect Immun.*, 75(8): 4020-9 (2007); Bielinska et al., "Nasal Immunization with a Recombinant HIV gp120 and Nanoemulsion Adjuvant Produces Th1 Polarized Responses and Neutralizing Antibodies to Primary HIV Type 1 Isolates," *AIDS Research and Human Retroviruses*, 24(2): 271-81 (2008); Bielinska et al., "A Novel, Killed-Virus Nasal Vaccinia Virus Vaccine," *Clin. Vaccine Immunol.*, 15(2): 348-58 (2008); Warren et al., "Pharmacological and Toxicological Studies on Cetylpyridinium Chloride, A New Germicide," *J. Pharmacol. Exp. Ther.*, 74:401-8) (1942)). Examples of such antigens include protective antigen (PA) of anthrax (Bielinska et al., Infect. Immun., 75(8): 4020-9 (2007)), whole vaccinia virus (Bielinska et al., Clin. Vaccine Immunol., 15(2): 348-58 (2008)) or gp120 protein of Human Immune Deficiency Virus (Bielinska et al., AIDS Research and Human Retroviruses. 24(2): 271-81 (2008)). These studies demonstrate the broad application of the nanoemulsion adjuvant with a variety of antigens including RSV antigens.

The nanoemulsion RSV vaccine of the invention can be administered to a subject using any pharmaceutically acceptable method, such as for example, intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, topically administered after scarification, mucosally administered, via an aerosol, or via a buccal or nasal spray formulation. Further, the nanoemulsion RSV vaccine can be formulated into any pharmaceutically acceptable dosage form, such as a liquid dispersion, gel, aerosol, pulmonary aerosol, nasal aerosol, ointment, cream, semi-solid dosage form, or a suspension. Further, the nanoemulsion RSV vaccine may be a controlled release formulation, sustained release formulation, immediate release formulation, or any combination thereof. Further, the nanoemulsion RSV vaccine may be a transdermal delivery system such as a patch or administered by a pressurized or pneumatic device (i.e., a "gene gun").

In one embodiment of the invention, the nanoemulsion RSV vaccine comprises droplets having an average diameter of less than about 1000 nm and: (a) an aqueous phase; (b) about 1% oil to about 80% oil; (c) about 0.1% to about 50% organic solvent; (d) about 0.001% to about 10% of a surfactant or detergent; or (e) any combination thereof. In another embodiment of the invention, the nanoemulsion vaccine comprises: (a) an aqueous phase; (b) about 1% oil to about 80% oil; (c) about 0.1% to about 50% organic solvent; (d) about 0.001% to about 10% of a surfactant or detergent; and (e) at least one RSV immunogen. In another embodiment of the invention, the nanoemulsion lacks an organic solvent.

The quantities of each component present in the nanoemulsion and/or nanoemulsion vaccine refer to a therapeutic nanoemulsion and/or nanoemulsion RSV vaccine.

In one embodiment, the nanoemulsion vaccine droplets have an average diameter selected from the group consisting of less than about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, greater than about 50 nm, greater than about 70 nm, greater than about 125 nm, and any combination thereof.

In one embodiment, the nanoemulsion and/or nanoemulsion vaccine comprises a cationic surfactant which is cetylpyridinium chloride (CPC). CPC may have a concentration in the nanoemulsion RSV vaccine of less than about 5.0% and greater than about 0.001%, or further, may have a concentration of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, less than about 0.10%, greater than about 0.001%, greater than about 0.002%, greater than about 0.003%, greater than about 0.004%, greater than about 0.005%, greater than about 0.006%, greater than about 0.007%, greater than about 0.008%, greater than about 0.009%, and greater than about 0.010%.

In a further embodiment, the nanoemulsion RSV vaccine comprises a non-ionic surfactant, such as a polysorbate surfactant, which may be polysorbate 80 or polysorbate 20, and may have a concentration of about 0.01% to about 5.0%, or about 0.1% to about 3% of polysorbate 80. The nanoemulsion RSV vaccine may further comprise at least one preservative. In another embodiment of the invention, the nanoemulsion RSV vaccine comprises a chelating agent.

In yet another embodiment, the nanoemulsion RSV vaccine further comprises an immune modulator, such as chitosan or glucan. An immune modulator can be present in the vaccine composition at any pharmaceutically acceptable amount including, but not limited to, from about 0.001% up to about 10%, and any amount in between, such as about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10%.

A. DEFINITIONS

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the term "adjuvant" refers to an agent that increases the immune response to an antigen (e.g., a pathogen). As used herein, the term "immune response" refers to a subject's (e.g., a human or another animal) response by the immune system to immunogens (i.e., antigens) which the subject's immune system recognizes as foreign. Immune responses include both cell-mediated immune responses (responses mediated by antigen-specific T cells and non-specific cells of the immune system) and humoral immune responses (responses mediated by antibodies present in the plasma lymph, and tissue fluids). The term "immune response" encompasses both the initial responses to an immunogen (e.g., a pathogen) as well as memory responses that are a result of "acquired immunity."

As used herein, the term "attenuated" HRSV refers to viral particles with reduced virulence and pathogenicity and in animal models and human will not result in clinical diseases.

The terms "chelator" or "chelating agent" refer to any materials having more than one atom with a lone pair of electrons that are available to bond to a metal ion.

As used herein, the term "enhanced immunity" refers to an increase in the level of acquired immunity to a given pathogen following administration of a vaccine of the present invention relative to the level of acquired immunity when a vaccine of the present invention has not been administered.

As used herein, the term "hyperproducer" refers to a viral strain that is capable of selectively producing at least 2-fold higher levels of viral structural proteins over standard viral strains. In the preferred embodiment, hyperproducer refers to the unique demonstration that HRSV-L19 produces levels of F and G proteins that are considerably higher than the comparable A2 HRSV strain.

As used herein, the term "immunogen" refers to an antigen that is capable of eliciting an immune response in a subject. In preferred embodiments, immunogens elicit immunity against the immunogen (e.g., a pathogen or a pathogen product) when administered in combination with a nanoemulsion of the present invention.

As used herein, the term "inactivated" HRSV refers to virion particles that are incapable of infecting host cells and are noninfectious in pertinent animal models.

As used herein, the term "intranasal(ly)" refers to application of the compositions of the present invention to the surface of the skin and mucosal cells and tissues of the nasal passages, e.g., nasal mucosa, sinus cavity, nasal turbinates, or other tissues and cells which line the nasal passages.

The term "nanoemulsion," as used herein, includes small oil-in-water dispersions or droplets, as well as other lipid structures which can form as a result of hydrophobic forces which drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. The present invention contemplates that one skilled in the art will appreciate this distinction when necessary for understanding the specific embodiments herein disclosed.

The terms "pharmaceutically acceptable" or "pharmacologically acceptable," as used herein, refer to compositions that do not substantially produce adverse allergic or adverse immunological reactions when administered to a host (e.g., an animal or a human). Such formulations include any pharmaceutically acceptable dosage form. Examples of such pharmaceutically acceptable dosage forms include, but are not limited to, dips, sprays, seed dressings, stem injections, lyophilized dosage forms, sprays, and mists. As used herein, "pharmaceutically acceptable carrier" includes any and all solvents, dispersion media, coatings, wetting agents (e.g., sodium lauryl sulfate), isotonic and absorption delaying agents, disintegrants (e.g., potato starch or sodium starch glycolate), and the like.

As used herein, the term "topical(ly)" refers to application of the compositions of the present invention to the surface of the skin and mucosal cells and tissues (e.g., buccal, lingual, sublingual, masticatory, respiratory or nasal mucosa, nasal turbinates and other tissues and cells which line hollow organs or body cavities).

As used herein, "viral particles" refers to mature virions, partial virions, empty capsids, defective interfering particles, and viral envelopes.

B. STABILITY OF THE NANOEMULSION RSV VACCINES OF THE INVENTION

The nanoemulsion RSV vaccines of the invention can be stable at about 40° C. and about 75% relative humidity for a time period of at least up to about 2 days, at least up to about 2 weeks, at least up to about 1 month, at least up to about 3 months, at least up to about 6 months, at least up to about 12 months, at least up to about 18 months, at least up to about 2 years, at least up to about 2.5 years, or at least up to about 3 years.

In another embodiment of the invention, the nanoemulsion RSV vaccines of the invention can be stable at about 25° C. and about 60% relative humidity for a time period of at least up least up to about 2 days, at least up to about 2 weeks, to about 1 month, at least up to about 3 months, at least up to about 6 months, at least up to about 12 months, at least up to about 18 months, at least up to about 2 years, at least up to about 2.5 years, or at least up to about 3 years, at least up to about 3.5 years, at least up to about 4 years, at least up to about 4.5 years, or at least up to about 5 years.

Further, the nanoemulsion RSV vaccines of the invention can be stable at about 4° C. for a time period of at least up to about 1 month, at least up to about 3 months, at least up to about 6 months, at least up to about 12 months, at least up to about 18 months, at least up to about 2 years, at least up to about 2.5 years, at least up to about 3 years, at least up to about 3.5 years, at least up to about 4 years, at least up to about 4.5 years, at least up to about 5 years, at least up to about 5.5 years, at least up to about 6 years, at least up to about 6.5 years, or at least up to about 7 years.

The nanoemulsion RSV vaccines of the invention can be stable at about −20° C. for a time period of at least up to about 1 month, at least up to about 3 months, at least up to about 6 months, at least up to about 12 months, at least up to about 18 months, at least up to about 2 years, at least up to about 2.5 years, at least up to about 3 years, at least up to about 3.5 years, at least up to about 4 years, at least up to about 4.5 years, at least up to about 5 years, at least up to about 5.5 years, at least up to about 6 years, at least up to about 6.5 years, or at least up to about 7 years.

These stability parameters are also applicable to nanoemulsion adjuvants and/or nanoemulsion RSV vaccines.

C. IMMUNE RESPONSE

The immune response of the subject can be measured by determining the titer and/or presence of antibodies against the RSV immunogen after administration of the nanoemulsion RSV vaccine to evaluate the humoral response to the immunogen. Seroconversion refers to the development of specific antibodies to an immunogen and may be used to evaluate the presence of a protective immune response. Such antibody-based detection is often measured using Western blotting or enzyme-linked immunosorbent (ELISA) assays or hemagglutination inhibition assays (HAI). Persons of skill in the art would readily select and use appropriate detection methods.

Another method for determining the subject's immune response is to determine the cellular immune response, such as through immunogen-specific cell responses, such as cytotoxic T lymphocytes, or immunogen-specific lymphocyte proliferation assay. Additionally, challenge by the pathogen may be used to determine the immune response, either in the subject, or, more likely, in an animal model. A person of skill in the art would be well versed in the methods of determining the immune response of a subject and the invention is not limited to any particular method.

D. NANOEMULSION RSV VACCINES

1. Droplet Size

The nanoemulsion RSV vaccine of the present invention comprises droplets having an average diameter size of less than about 1,000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, or any combination thereof. In one embodiment, the droplets have an average diameter size greater than about 125 nm and less than or equal to about 600 nm. In a different embodiment, the droplets have an average diameter size greater than about 50 nm or greater than about 70 nm, and less than or equal to about 125 nm.

2. Aqueous Phase

The aqueous phase can comprise any type of aqueous phase including, but not limited to, water (e.g., $H_2O$, distilled water, purified water, water for injection, de-ionized water, tap water) and solutions (e.g., phosphate buffered saline (PBS) solution). In certain embodiments, the aqueous phase comprises water at a pH of about 4 to 10, preferably about 6 to 8. The water can be deionized (hereinafter "$DiH_2O$"). In some embodiments the aqueous phase comprises phosphate buffered saline (PBS). The aqueous phase may further be sterile and pyrogen free.

3. Organic Solvents

Organic solvents in the nanoemulsion RSV vaccines of the invention include, but are not limited to, $C_1$-$C_{12}$ alcohol, diol, triol, dialkyl phosphate, tri-alkyl phosphate, such as tri-n-butyl phosphate, semi-synthetic derivatives thereof, and combinations thereof. In one aspect of the invention, the organic solvent is an alcohol chosen from a nonpolar solvent, a polar solvent, a protic solvent, or an aprotic solvent.

Suitable organic solvents for the nanoemulsion RSV vaccine include, but are not limited to, ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and any combination thereof.

4. Oil Phase

The oil in the nanoemulsion RSV vaccine of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (simmondsia chinensis seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, chenopodium oil, citronellal, citral, citronellol, chamazulene, yarrow, guaiazulene, chamomile, semi-synthetic derivatives, or combinations thereof.

In one aspect of the invention, the volatile oil in the silicone component is different than the oil in the oil phase.

5. Surfactants

The surfactant in the nanoemulsion RSV vaccine of the invention can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference.

Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxystearate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thighlycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isoproppyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2CH_2)_y$—$OH$, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23.

In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton®X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quarternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl (tetradecyl)ammonium bromide, 1,3,5-Triazine-1,3,5(2H, 4H,6H)-triethanol, 1-Decanaminium, N-decyl-N,N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy) ethyl dimethyl benzyl ammonium chloride, Alkyl 1 or 3 benzyl-1-(2-hydroxethyl)-2-imidazolinium chloride, Alkyl bis(2-hydroxyethyl)benzyl ammonium chloride, Alkyl demethyl benzyl ammonium chloride, Alkyl dimethyl 3,4-dichlorobenzyl ammonium chloride (100% $C_{12}$), Alkyl dimethyl 3,4-dichlorobenzyl ammonium chloride (50% $C_{14}$, 40% $C_{12}$, 10% $C_{16}$), Alkyl dimethyl 3,4-dichlorobenzyl ammonium chloride (55% $C_{14}$, 23% $C_{12}$, 20% $C_{16}$), Alkyl dimethyl benzyl ammonium chloride, Alkyl dimethyl benzyl ammonium chloride (100% $C_{14}$), Alkyl dimethyl benzyl ammonium chloride (100% $C_{16}$), Alkyl dimethyl benzyl ammonium chloride (41% $C_{14}$, 28% $C_{12}$), Alkyl dimethyl benzyl ammonium chloride (47% $C_{12}$, 18% $C_{14}$), Alkyl dimethyl benzyl ammonium chloride (55% C16, 20% $C_{14}$), Alkyl dimethyl benzyl ammonium chloride (58% $C_{14}$, 28% $C_{16}$), Alkyl dimethyl benzyl ammonium chloride (60% $C_{14}$, 25% $C_{12}$), Alkyl dimethyl benzyl ammonium chloride (61% $C_{11}$, 23% $C_{14}$), Alkyl dimethyl benzyl ammonium chloride (61% $C_{12}$, 23% $C_{14}$), Alkyl dimethyl benzyl ammonium chloride (65% $C_{12}$, 25% $C_{14}$), Alkyl dimethyl benzyl ammonium chloride (67% $C_{12}$, 24% $C_{14}$), Alkyl dimethyl benzyl ammonium chloride (67% $C_{12}$, 25% $C_{14}$), Alkyl dimethyl benzyl ammonium chloride (90% $C_{14}$, 5% $C_{12}$), Alkyl dimethyl benzyl ammonium chloride (93% $C_{14}$, 4% $C_{12}$), Alkyl dimethyl benzyl ammonium chloride (95% $C_{16}$, 5% $C_{18}$), Alkyl dimethyl benzyl ammonium chloride, Alkyl didecyl dimethyl ammonium chloride, Alkyl dimethyl benzyl ammonium chloride, Alkyl dimethyl benzyl ammonium chloride ($C_{12-16}$), Alkyl dimethyl benzyl ammonium chloride ($C_{12-18}$), Alkyl dimethyl benzyl ammonium chloride, dialkyl dimethyl benzyl ammonium chloride, Alkyl dimethyl dimethylbenzyl ammonium chloride, Alkyl dimethyl ethyl ammonium bromide (90% $C_{14}$, 5% $C_{16}$, 5% $C_{12}$), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% $C_{14}$), Alkyl dimethyl isopropylbenzyl ammonium chloride (50% $C_{12}$, 30% $C_{14}$, 17% $C_{16}$, 3% $C_{18}$), Alkyl trimethyl ammonium chloride (58% $C_{18}$, 40% $C_{16}$, 1% $C_{14}$, 1% $C_{12}$), Alkyl trimethyl ammonium chloride (90% $C_{18}$, 10% $C_{16}$), Alkyldimethyl (ethylbenzyl)ammonium chloride ($C_{12-18}$), Di-($C_{8-10}$)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis(2-hydroxyethyl)octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris(2-hydroxyethyl)-s-triazine, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysilyl propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetradecyltrimethylammonium bromide. In particularly preferred embodiments, the cationic halogen containing compound is CPC, although the compositions of the present invention are not limited to formulation with an particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4, 1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-Dodecyldimethylammonio)propanesulfonate inner salt, SigmaUltra, 3-(Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-Dimethyloctylammonio) propanesulfonate inner salt, 3-(N,N-Dimethylpalmitylammonio)propanesulfonate, semi-synthetic derivatives thereof, and combinations thereof.

In some embodiments, the nanoemulsion RSV vaccine comprises a cationic surfactant, which can be cetylpyridinium chloride. In other embodiments of the invention, the nanoemulsion RSV vaccine comprises a cationic surfactant, and the concentration of the cationic surfactant is less than about 5.0% and greater than about 0.001%. In yet another embodiment of the invention, the nanoemulsion RSV vaccine comprises a cationic surfactant, and the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, or less than about 0.10%. Further, the concentration of the cationic agent in the nanoemulsion vaccine is greater than about 0.002%, greater than about 0.003%, greater than about 0.004%, greater than about 0.005%, greater than about 0.006%, greater than about 0.007%, greater than about 0.008%, greater than about 0.009%, greater than about 0.010%, or greater than about 0.001%. In one embodiment, the concentration of the cationic agent in the nanoemulsion vaccine is less than about 5.0% and greater than about 0.001%.

In another embodiment of the invention, the nanoemulsion vaccine comprises at least one cationic surfactant and at least one non-cationic surfactant. The non-cationic surfactant is a nonionic surfactant, such as a polysorbate (Tween), such as polysorbate 80 or polysorbate 20. In one embodiment, the non-ionic surfactant is present in a concentration of about 0.01% to about 5.0%, or the non-ionic surfactant is present in a concentration of about 0.1% to about 3%. In yet another embodiment of the invention, the nanoemulsion vaccine comprises a cationic surfactant present in a concentration of about 0.01% to about 2%, in combination with a nonionic surfactant.

6. Additional Ingredients

Additional compounds suitable for use in the nanoemulsion RSV vaccines of the invention include but are not limited to one or more solvents, such as an organic phosphate-based solvent, bulking agents, coloring agents, pharmaceutically acceptable excipients, a preservative, pH adjuster, buffer, chelating agent, etc. The additional compounds can be admixed into a previously emulsified nanoemulsion vaccine, or the additional compounds can be added to the original mixture to be emulsified. In certain of these embodiments, one or more additional compounds are admixed into an existing nanoemulsion composition immediately prior to its use.

Suitable preservatives in the nanoemulsion RSV vaccines of the invention include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof. Other suitable preservatives include, but are not limited to, benzyl alcohol, chlorhexidine (bis(p-chlorophenyldiguanido) hexane), chlorphenesin (3-(-4-chlorophenoxy)-propane-1,2-diol), Kathon CG (methyl and methylchloroisothiazolinone), parabens (methyl, ethyl, propyl, butyl hydrobenzoates), phenoxyethanol (2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

The nanoemulsion RSV vaccine may further comprise at least one pH adjuster. Suitable pH adjusters in the nanoemulsion vaccine of the invention include, but are not limited to, diethyanolamine, lactic acid, monoethanolamine, triethylanolamine, sodium hydroxide, sodium phosphate, semi-synthetic derivatives thereof, and combinations thereof.

In addition, the nanoemulsion RSV vaccine can comprise a chelating agent. In one embodiment of the invention, the chelating agent is present in an amount of about 0.0005% to about 1%. Examples of chelating agents include, but are not limited to, ethylenediamine, ethylenediaminetetraacetic acid (EDTA), phytic acid, polyphosphoric acid, citric acid, gluconic acid, acetic acid, lactic acid, and dimercaprol, and a preferred chelating agent is ethylenediaminetetraacetic acid.

The nanoemulsion RSV vaccine can comprise a buffering agent, such as a pharmaceutically acceptable buffering agent. Examples of buffering agents include, but are not limited to, 2-Amino-2-methyl-1,3-propanediol, ≥99.5% (NT), 2-Amino-2-methyl-1-propanol, ≥99.0% (GC), L-(+)-Tartaric acid, ≥99.5% (T), ACES, ≥99.5% (T), ADA, ≥99.0% (T), Acetic acid, ≥99.5% (GC/T), Acetic acid, for luminescence, ≥99.5% (GC/T), Ammonium acetate solution, for molecular biology, ~5 M in $H_2O$, Ammonium acetate, for luminescence, ≥99.0% (calc. on dry substance, T), Ammonium bicarbonate, ≥99.5% (T), Ammonium citrate dibasic, ≥99.0% (T), Ammonium formate solution, 10 M in $H_2O$, Ammonium formate, ≥99.0% (calc. based on dry substance, NT), Ammonium oxalate monohydrate, ≥99.5% (RT), Ammonium phosphate dibasic solution, 2.5 M in $H_2O$, Ammonium phosphate dibasic, ≥99.0% (T), Ammonium phosphate monobasic solution, 2.5 M in $H_2O$, Ammonium phosphate monobasic, ≥99.5% (T), Ammonium sodium phosphate dibasic tetrahydrate, ≥99.5% (NT), Ammonium sulfate solution, for molecular biology, 3.2 M in $H_2O$, Ammonium tartrate dibasic solution, 2 M in $H_2O$ (colorless solution at 20° C.), Ammonium tartrate dibasic, ≥99.5% (T), BES buffered saline, for molecular biology, 2× concentrate, BES, ≥99.5% (T), BES, for molecular biology, ≥99.5% (T), BICINE buffer Solution, for molecular biology, 1 M in $H_2O$, BICINE, ≥99.5% (T), BIS-TRIS, ≥99.0% (NT), Bicarbonate buffer solution, >0.1 M $Na_2CO_3$, >0.2 M $NaHCO_3$, Boric acid, ≥99.5% (T), Boric acid, for molecular biology, ≥99.5% (T), CAPS, ≥99.0% (TLC), CHES, ≥99.5% (T), Calcium acetate hydrate, ≥99.0% (calc. on dried material, KT), Calcium carbonate, precipitated, ≥99.0% (KT), Calcium citrate tribasic tetrahydrate, ≥98.0% (calc. on dry substance, KT), Citrate Concentrated Solution, for molecular biology, 1 M in $H_2O$, Citric acid, anhydrous, ≥99.5% (T), Citric acid, for luminescence, anhydrous, ≥99.5% (T), Diethanolamine, ≥99.5% (GC), EPPS, ≥99.0% (T), Ethylenediaminetetraacetic acid disodium salt dihydrate, for molecular biology, ≥99.0% (T), Formic acid solution, 1.0 M in $H_2O$, Gly-Gly-Gly, ≥99.0% (NT), Gly-Gly, ≥99.5% (NT), Glycine, ≥99.0% (NT), Glycine, for luminescence, ≥99.0% (NT), Glycine, for molecular biology, ≥99.0% (NT), HEPES buffered saline, for molecular biology, 2× concentrate, HEPES, ≥99.5% (T), HEPES, for molecular biology, ≥99.5% (T), Imidazole buffer Solution, 1 M in $H_2O$, Imidazole, ≥99.5% (GC), Imidazole, for luminescence, ≥99.5% (GC), Imidazole, for molecular biology, ≥99.5% (GC), Lipoprotein Refolding Buffer, Lithium acetate dihydrate, ≥99.0% (NT), Lithium citrate tribasic tetrahydrate, ≥99.5% (NT), MES hydrate, ≥99.5% (T), MES monohydrate, for luminescence, ≥99.5% (T), MES solution, for molecular biology, 0.5 M in $H_2O$, MOPS, ≥99.5% (T), MOPS, for luminescence, ≥99.5% (T), MOPS, for molecular biology, ≥99.5% (T), Magnesium acetate solution, for molecular biology, ~1 M in $H_2O$, Magnesium acetate tetrahydrate, ≥99.0% (KT), Magnesium citrate tribasic nonahydrate, ≥98.0% (calc. based on dry substance, KT), Magnesium formate solution, 0.5 M in $H_2O$, Magnesium phosphate dibasic trihydrate, ≥98.0% (KT), Neutralization solution for the in-situ hybridization for in-situ hybridization, for molecular biology, Oxalic acid dihydrate, ≥99.5% (RT), PIPES, ≥99.5% (T), PIPES, for molecular biology, ≥99.5% (T), Phosphate buffered saline, solution (autoclaved), Phosphate buffered saline, washing buffer for peroxidase conjugates in Western Blotting, 10× concentrate, piperazine, anhydrous, ≥99.0% (T), Potassium D-tartrate monobasic, ≥99.0% (T), Potassium acetate solution, for molecular biology, Potassium acetate solution, for molecular biology, 5 M in $H_2O$, Potassium acetate solution, for molecular biology, ~1 M in $H_2O$, Potassium acetate, ≥99.0% (NT), Potassium acetate, for luminescence, ≥99.0% (NT), Potassium acetate, for molecular biology, ≥99.0% (NT), Potassium bicarbonate, ≥99.5% (T), Potassium carbonate, anhydrous, ≥99.0% (T), Potassium chloride, ≥99.5% (AT), Potassium citrate monobasic, ≥99.0% (dried material, NT), Potassium citrate tribasic solution, 1 M in $H_2O$, Potassium formate solution, 14 M in $H_2O$, Potassium formate, ≥99.5% (NT), Potassium oxalate monohydrate, ≥99.0% (RT), Potassium phosphate dibasic, anhydrous, ≥99.0% (T), Potassium phosphate dibasic, for luminescence, anhydrous, ≥99.0% (T), Potassium phosphate dibasic, for molecular biology, anhydrous, ≥99.0% (T), Potassium phosphate monobasic, anhydrous, ≥99.5% (T), Potassium phosphate monobasic, for molecular biology, anhydrous, ≥99.5% (T), Potassium phosphate tribasic monohydrate, ≥95% (T), Potassium phthalate monobasic, ≥99.5% (T), Potassium sodium tartrate solution, 1.5 M in $H_2O$, Potassium sodium tartrate tetrahydrate, ≥99.5% (NT), Potassium tetraborate tetrahydrate, ≥99.0% (T), Potassium tetraoxalate dihydrate, ≥99.5% (RT), Propionic acid solution, 1.0 M in $H_2O$, STE buffer solution, for molecular biology, pH 7.8, STET buffer solution, for molecular biology, pH 8.0, Sodium 5,5-diethylbarbiturate, ≥99.5% (NT), Sodium acetate solution, for molecular biology, ~3 M in $H_2O$, Sodium acetate trihydrate, ≥99.5% (NT), Sodium acetate, anhydrous, ≥99.0% (NT), Sodium acetate, for luminescence, anhydrous, ≥99.0% (NT), Sodium acetate, for molecular biology, anhydrous, ≥99.0% (NT), Sodium bicarbonate, ≥99.5% (T), Sodium bitartrate monohydrate, ≥99.0% (T), Sodium carbonate decahydrate, ≥99.5% (T), Sodium carbonate, anhydrous, ≥99.5% (calc. on dry substance, T), Sodium citrate monobasic, anhydrous, ≥99.5% (T), Sodium citrate tribasic dihydrate, ≥99.0% (NT), Sodium citrate tribasic dihydrate, for luminescence, ≥99.0% (NT), Sodium citrate tribasic dihydrate, for molecular biology, ≥99.5% (NT), Sodium formate solution, 8 M in $H_2O$, Sodium oxalate, ≥99.5% (RT), Sodium phosphate dibasic dihydrate, ≥99.0% (T), Sodium phosphate dibasic dihydrate, for luminescence, ≥99.0% (T), Sodium phosphate dibasic dihydrate, for molecular biology, ≥99.0% (T), Sodium phosphate dibasic dodecahydrate, ≥99.0% (T), Sodium phosphate dibasic solution, 0.5 M in $H_2O$, Sodium phosphate dibasic, anhydrous, ≥99.5% (T), Sodium phosphate dibasic, for molecular biology, ≥99.5% (T), Sodium phosphate monobasic dihydrate, ≥99.0% (T), Sodium phosphate monobasic dihydrate, for molecular biology, ≥99.0% (T), Sodium phosphate monobasic monohydrate, for molecular biology, ≥99.5% (T), Sodium phosphate monobasic solution, 5 M in $H_2O$, Sodium pyrophosphate dibasic, ≥99.0% (T), Sodium pyrophosphate tetrabasic decahydrate, ≥99.5% (T), Sodium tartrate dibasic dihydrate, ≥99.0% (NT), Sodium tartrate dibasic solution, 1.5 M in $H_2O$ (colorless solution at 20° C.), Sodium tetraborate decahydrate, ≥99.5% (T), TAPS, ≥99.5% (T), TES, ≥99.5% (calc. based on dry substance, T), TM buffer solution, for molecular biology, pH 7.4, TNT buffer solution, for molecular biology, pH 8.0, TRIS Glycine buffer solution, 10× concentrate, TRIS acetate-EDTA buffer solution, for molecular biology, TRIS buffered saline, 10× concentrate, TRIS glycine SDS buffer solution, for electrophoresis, 10× concentrate, TRIS phosphate-EDTA buffer solution, for molecular biology, concentrate, 10× concentrate, Tricine, ≥99.5% (NT), Triethanolamine, ≥99.5% (GC), Triethylamine, ≥99.5% (GC), Triethylammonium acetate buffer, volatile buffer, ~1.0 M in $H_2O$, Triethylammonium phosphate solution, volatile buffer, ~1.0 M in $H_2O$, Trimethylammonium acetate solution, volatile buffer, ~1.0 M in $H_2O$, Trimethylammonium phosphate solution, volatile buffer, ~1 M in $H_2O$, Tris-EDTA buffer solution, for molecular biology, concentrate, 100× concentrate, Tris-EDTA buffer solution, for molecular biology, pH 7.4, Tris-EDTA buffer solution, for molecular biology, pH 8.0, Trizma® acetate, ≥99.0% (NT), Trizma® base, ≥99.8% (T), Trizma® base, ≥99.8% (T), Trizma® base, for luminescence, ≥99.8% (T), Trizma® base, for molecular biology, ≥99.8% (T), Trizma® carbonate, ≥98.5% (T), Trizma® hydrochloride buffer solution, for molecular biology, pH 7.2, Trizma® hydrochloride buffer solution, for molecular biology, pH 7.4, Trizma® hydrochloride buffer solution, for molecular biology, pH 7.6, Trizma® hydrochloride buffer solution, for molecular biology, pH 8.0, Trizma® hydrochloride, ≥99.0% (AT), Trizma® hydrochloride, for luminescence, ≥99.0% (AT), Trizma® hydrochloride, for molecular biology, ≥99.0% (AT), and Trizma® maleate, ≥99.5% (NT).

The nanoemulsion RSV vaccine can comprise one or more emulsifying agents to aid in the formation of emulsions. Emulsifying agents include compounds that aggregate at the oil/water interface to form a kind of continuous membrane that prevents direct contact between two adjacent droplets. Certain embodiments of the present invention feature nanoemulsion vaccines that may readily be diluted with water or another aqueous phase to a desired concentration without impairing their desired properties.

7. Immune Modulators

As noted above, the RSV vaccine can further comprise one or more immune modulators. Examples of immune modulators include, but are not limited to, chitosan, glucan, enterotoxin, nucleic acid (CpG motifs), MF59, alum, ASO system, etc. It is within the purview of one of ordinary skill in the art to employ suitable immune modulators in the context of the present invention.

An immune modulator can be present in the vaccine composition at any pharmaceutically acceptable amount including, but not limited to, from about 0.001% up to about 10%, and any amount inbetween, such as about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10%.

E. PHARMACEUTICAL COMPOSITIONS

The nanoemulsion RSV vaccines of the invention may be formulated into pharmaceutical compositions that comprise the nanoemulsion RSV vaccine in a therapeutically effective amount and suitable, pharmaceutically-acceptable excipients for pharmaceutically acceptable delivery. Such excipients are well known in the art.

By the phrase "therapeutically effective amount" it is meant any amount of the nanoemulsion RSV vaccine that is effective in preventing, treating or ameliorating a disease caused by the RSV pathogen associated with the immunogen administered in the composition comprising the nanoemulsion RSV vaccine. By "protective immune response" it is meant that the immune response is associated with prevention, treating, or amelioration of a disease. Complete prevention is not required, though is encompassed by the present invention. The immune response can be evaluated using the methods discussed herein or by any method known by a person of skill in the art.

Intranasal administration includes administration via the nose, either with or without concomitant inhalation during administration. Such administration is typically through contact by the composition comprising the nanoemulsion RSV vaccine with the nasal mucosa, nasal turbinates or sinus cavity. Administration by inhalation comprises intranasal administration, or may include oral inhalation. Such administration may also include contact with the oral mucosa, bronchial mucosa, and other epithelia.

Exemplary dosage forms for pharmaceutical administration are described herein. Examples include but are not limited to liquids, ointments, creams, emulsions, lotions, gels, bioadhesive gels, sprays, aerosols, pastes, foams, sunscreens, capsules, microcapsules, suspensions, pessary, powder, semi-solid dosage form, etc.

The pharmaceutical nanoemulsion RSV vaccines may be formulated for immediate release, sustained release, controlled release, delayed release, or any combinations thereof, into the epidermis or dermis. In some embodiments, the formulations may comprise a penetration-enhancing agent. Suitable penetration-enhancing agents include, but are not limited to, alcohols such as ethanol, triglycerides and aloe compositions. The amount of the penetration-enhancing agent may comprise from about 0.5% to about 40% by weight of the formulation.

The nanoemulsion RSV vaccines of the invention can be applied and/or delivered utilizing electrophoretic delivery/electrophoresis. Further, the composition may be a transdermal delivery system such as a patch or administered by a pressurized or pneumatic device (i.e., "gene gun"). Such methods, which comprise applying an electrical current, are well known in the art.

The pharmaceutical nanoemulsion RSV vaccines for administration may be applied in a single administration or in multiple administrations.

If applied topically, the nanoemulsion RSV vaccines may be occluded or semi-occluded. Occlusion or semi-occlusion may be performed by overlaying a bandage, polyoleofin film, article of clothing, impermeable barrier, or semi-impermeable barrier to the topical preparation.

An exemplary nanoemulsion adjuvant composition according to the invention is designated "$W_{80}5EC$" adjuvant. The composition of $W_{80}5EC$ adjuvant is shown in the table below (Table 1)H. The mean droplet size for the $W_{80}5EC$ adjuvant is ~400 nm. All of the components of the nanoemulsion are included on the FDA inactive ingredient list for Approved Drug Products.

TABLE 1

| $W_{80}5EC$ Formulation | |
|---|---|
| Function | $W_{80}5EC$-Adjuvant<br>Mean Droplet Size ≈ 400 nm |
| Aqueous Diluent | Purified Water, USP |
| Hydrophobic Oil (Core) | Soybean Oil, USP (super refined) |
| Organic Solvent | Dehydrated Alcohol, USP (anhydrous ethanol) |
| Surfactant | Polysorbate 80, NF |
| Emulsifying Agent Preservative | Cetylpyridinium Chloride, USP |

The nanoemulsion adjuvants are formed by emulsification of an oil, purified water, nonionic detergent, organic solvent and surfactant, such as a cationic surfactant. An exemplary specific nanoemulsion adjuvant is designated as "60% $W_{80}5EC$". The 60% $W_{80}5EC$-adjuvant is composed of the ingredients shown in Table 2 below: purified water, USP; soybean oil USP; Dehydrated Alcohol, USP [anhydrous ethanol]; Polysorbate 80, NF and cetylpyridinium chloride, USP (CPC). All components of this exemplary nanoemulsion are included on the FDA list of approved inactive ingredients for Approved Drug Products.

TABLE 2

| Composition of 60% $W_{80}5EC$-Adjavant (w/w %) | |
|---|---|
| Ingredients | 60% $W_{80}5EC$ |
| Purified Water, USP | 54.10% |
| Soybean Oil, USP | 37.67% |
| Dehydrated Alcohol, USP (anhydrous ethanol) | 4.04% |
| Polysorbate 80, NF | 3.55% |
| Cetylpyridinium Chloride, USP | 0.64% |

F. METHODS OF MANUFACTURE

The nanoemulsions of the invention can be formed using classic emulsion forming techniques. See e.g., U.S. 2004/0043041. In an exemplary method, the oil is mixed with the aqueous phase under relatively high shear forces (e.g., using high hydraulic and mechanical forces) to obtain a nanoemulsion comprising oil droplets having an average diameter of less than about 1000 nm. Some embodiments of the invention employ a nanoemulsion having an oil phase comprising an alcohol such as ethanol. The oil and aqueous phases can be blended using any apparatus capable of producing shear forces sufficient to form an emulsion, such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In an exemplary embodiment, the nanoemulsions used in the methods of the invention comprise droplets of an oily discontinuous phase dispersed in an aqueous continuous phase, such as water or PBS. The nanoemulsions of the invention are stable, and do not deteriorate even after long storage periods. Certain nanoemulsions of the invention are non-toxic and safe when swallowed, inhaled, or contacted to the skin of a subject.

The compositions of the invention can be produced in large quantities and are stable for many months at a broad range of temperatures. The nanoemulsion can have textures ranging from that of a semi-solid cream to that of a thin lotion, to that of a liquid and can be applied topically by any pharmaceutically acceptable method as stated above, e.g., by hand, or nasal drops/spray.

As stated above, at least a portion of the emulsion may be in the form of lipid structures including, but not limited to, unilamellar, multilamellar, and paucliamellar lipid vesicles, micelles, and lamellar phases.

The present invention contemplates that many variations of the described nanoemulsions will be useful in the methods of the present invention. To determine if a candidate nanoemulsion is suitable for use with the present invention, three criteria are analyzed. Using the methods and standards described herein, candidate emulsions can be easily tested to determine if they are suitable. First, the desired ingredients are prepared using the methods described herein, to determine if a nanoemulsion can be formed. If a nanoemulsion cannot be formed, the candidate is rejected. Second, the candidate nanoemulsion should form a stable emulsion. A nanoemulsion is stable if it remains in emulsion form for a sufficient period to allow its intended use. For example, for nanoemulsions that are to be stored, shipped, etc., it may be desired that the nanoemulsion remain in emulsion form for months to years. Typical nanoemulsions that are relatively unstable, will lose their form within a day. Third, the candidate nanoemulsion should have efficacy for its intended use. For example, the emulsions of the invention should kill or disable RSV virus to a detectable level, or induce a protective immune response to a detectable level. The nanoemulsion of the invention can be provided in many different types of containers and delivery systems. For example, in some embodiments of the invention, the nanoemulsions are provided in a cream or other solid or semi-solid form. The nanoemulsions of the invention may be incorporated into hydrogel formulations.

The nanoemulsions can be delivered (e.g., to a subject or customers) in any suitable container. Suitable containers can be used that provide one or more single use or multi-use dosages of the nanoemulsion for the desired application. In some embodiments of the invention, the nanoemulsions are provided in a suspension or liquid form. Such nanoemulsions can be delivered in any suitable container including spray bottles and any suitable pressurized spray device. Such spray bottles may be suitable for delivering the nanoemulsions intranasally or via inhalation.

These nanoemulsion-containing containers can further be packaged with instructions for use to form kits.

The invention is further described by reference to the following examples, which are provided for illustration only. The invention is not limited to the examples, but rather includes all variations that are evident from the teachings provided herein. All publicly available documents referenced herein, including but not limited to U.S. patents, are specifically incorporated by reference.

EXAMPLES

Example 1

The purpose of this example is to compare HRSV Protein Expression for RSV A2 strain as compared to RSV L19 strain, and Cell Lysate vs. Supernatant.

Materials and Methods: All samples were prepared by infecting HEP-2 cells with the same amount of pfu from either A2 or L19 viruses. Twenty four hours post infection; the infected cells were treated with either one of the following:
 (1) Cell lysate to check for the cell associated proteins; after discarding the supernatant media, the cells were treated with SDS. This cell lysate was assayed for quantity of F protein associated with the cells.
 (2) Total cell and supernatant proteins; the cells and supernatant were frozen and thawed 3 times to lyse the cells and all the cell lysate was used to assay the F protein in the cells and the media.

L19 and A2 virus was extracted and purified from HEP-2 infected cells 4 days following infection. Purified virus was compared for protein contents.

Results: Normalized samples were assayed in Western blots using a polyclonal anti RSV antibodies. F and G protein contents were compared between L19 and A2 strains. The density of the bands was compared using image capturing and a Kodak software. A mock non-infected cell culture was prepared as a control.

Figure 2:
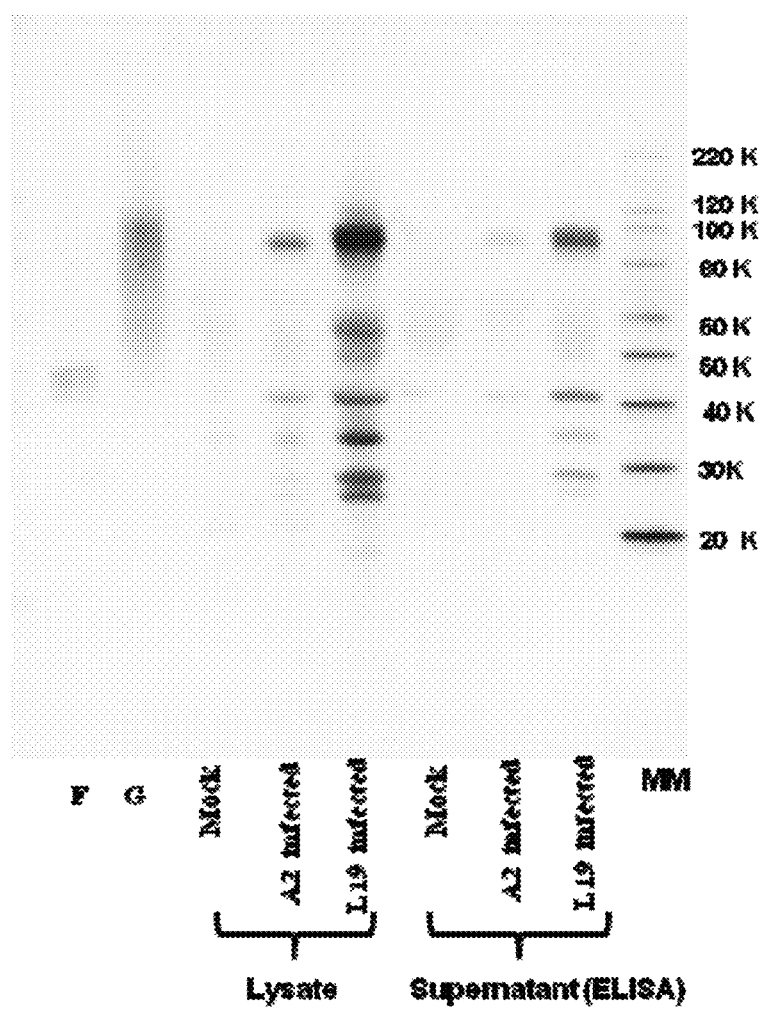
Figure 3:
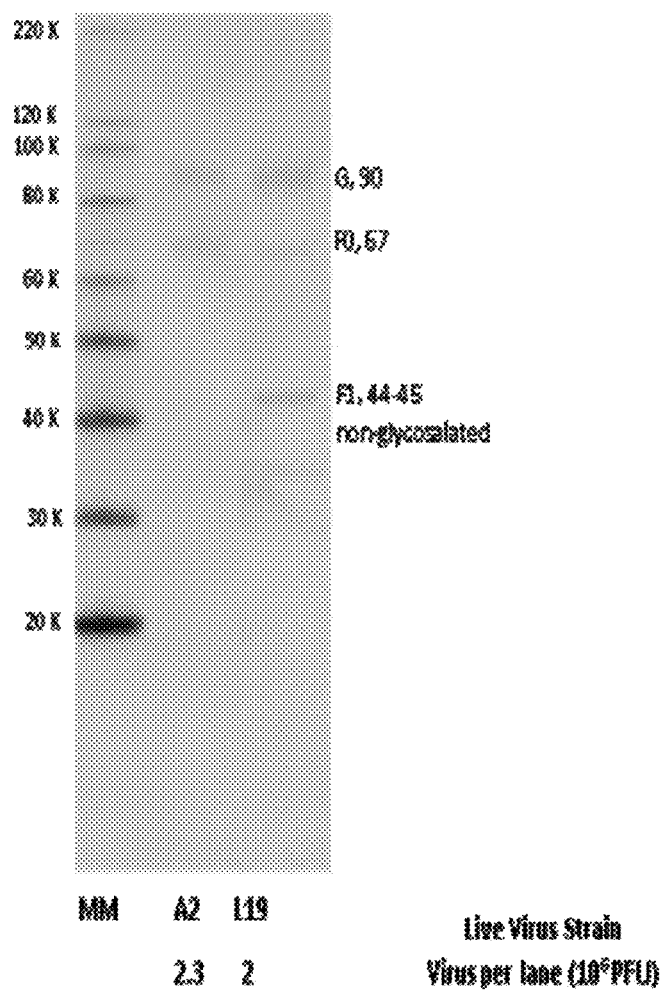

The results data are detailed in FIGS. 1-3 and Tables 3-5. FIG. 1 shows an SDS PAGE of HRSV Infected Cell Lysate (SDS treated) with L19 and A2, FIG. 2 shows an SDS-PAGE of L19 and A2 HRSV Cell Lysate (cells & supernatant), and FIG. 3 shows an SDS PAGE of HRSV L19 and A2 Purified Virus. Table 3 shows comparable HRSV F and G protein from L19 and A2 levels from SDS-PAGE. Table 4 shows comparable HRSV L19 and A2 F and G protein from infected cells (Lysate, Supernatant). Finally, Table 5 shows comparable HRSV L19 and A2 F and G protein from SDS PAGE.

TABLE 3

Comparable HRSV F and G Protein from L19 and A2 Levels from SDS-PAGE

|  | Mock | Infected with A2 | Infected with L19 | Band Density Ratio (L19/A2) |
|---|---|---|---|---|
| G (90 kDa) | No Band | 78241.1 | 356946.3 | 4.56 |
| F2 (44-45 kDa) | No Band | 38612 | 121328 | 3.14 |

TABLE 4

Comparable HRSV L19 and A2 F and G Protein from Infected Cells (Lysate, Supernatant)

|  | Lysate | | | Supernatant | | |
|---|---|---|---|---|---|---|
|  | Mock | Infected with A2 | Infected with L19 | Mock | Infected with A2 | Infected with L19 |
| G (90 kDa) | No Band | 27831 | 166308 | 0 | 4686 | 54142 |
| Ratio of L19:A2 | | | 6 | | | 11.6 |
| F2 (44-45 kDa) | No Band | 10645 | 43570 | No Band | 1860 | 18499 |
| Ratio of L19:A2 | | | 4.1 | | | 9.9 |

TABLE 5

Comparable HRSV L19 and A2 F and G Protein From SDS PAGE

|  | A2 ($2.3 \times 10^6$ pfu) | L19 ($2 \times 10^6$ pfu) | Ratio (L19/A2) |
|---|---|---|---|
| G | 5,039.1 | 11,401.1 | 2.26 |
| F0 + F2 | 4,481.81 | 9,700.39 | 2.16 |

Summary: RSV L19 virus infected cells produce between 3-11 fold higher quantities of RSV viral proteins as compared to A2 infected cells.

Example 2

The purpose of this example was to compare F protein expression in Hep-2 cells infected with different strains of RSV virus (L19 vs. A2) for various infection times (24 hours vs. 4 days).

Materials and Methods: Hep-2 cells were infected with either L19 or A2 RSV virus. 2 sets of 4 flasks total.

24 hours after virus infection, the first set of Hep-2 cells were lysed with or without culture supernatant. Samples were prepared as the following:

TABLE 6

| Plate 1 Infect with L19 | Plate 2 Infect with L19 24 hrs later | Plate 3 Infect with A2 | Plate 4 Infect with A2 |
|---|---|---|---|
| Discard Medium Add Tris Buffer (same volume) | Leave medium in | Discard medium Add Tris buffer Tris (Same volume) | Leave medium in |

TABLE 6-continued

| Plate 1 Infect with L19 | Plate 2 Infect with L19 24 hrs later | Plate 3 Infect with A2 | Plate 4 Infect with A2 |
|---|---|---|---|
| Lyze cells Lot # 1123, C + T | Lyze cells Lot # 1124, C + M | Lyze cells Lot # 1125, C + T | Lyze cells Lot # 1126, C + M |

C + TCCC + T = Cell + Tris Buffer (culture medium was discarded and replaced with equal volume of Tris buffer);
C + M = Cell + Culture Medium (culture medium reserved).

Four days after infection, the second set of Hep-2 cells were lysed with or without culture supernatant. Samples were prepared as the following:

TABLE 7

| Plate A Infected with L19 | | Plate B | | Plate C Infected with A2 4 days later | | Plate D | |
|---|---|---|---|---|---|---|---|
| Remove Medium and Save | | Leave Medium in | | Remove Medium and Save | | Leave Medium in | |
| Add Buffer (same volume) | Saved Medium | | | Add buffer (Same volume) | Saved Medium | | |
| Lyze cells Lot # 1127, C + T | | Lyze cells Lot # 1128, M | Lyze cells Lot # 1129, C + M | Lyze cells Lot # 1130, C + T | | Lyze cells Lot # 1131, M | Lyze cells Lot # 1132, C + M |

C + T = Cell + Tris Buffer (culture medium was replaced with equal volume of Tris buffer)
M = Culture Medium (culture medium was collected separately)
C + M = Cell + Culture Medium (culture medium reserved)

Some 7.5 µL of each sample was applied for Western blot analysis. The density of F and G protein bands were measured using Carestream Molecular Imaging Software 5.X.

Figure 4:
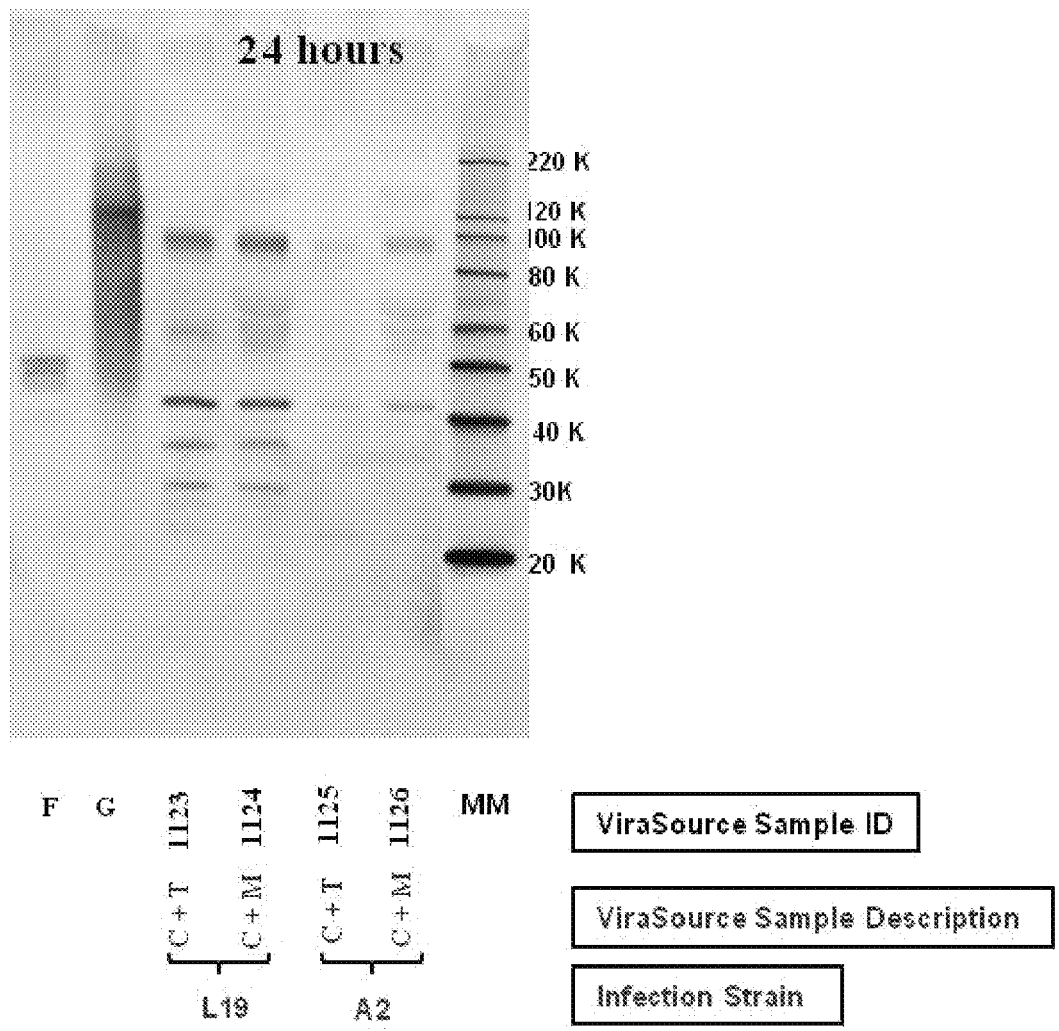
Figure 5:
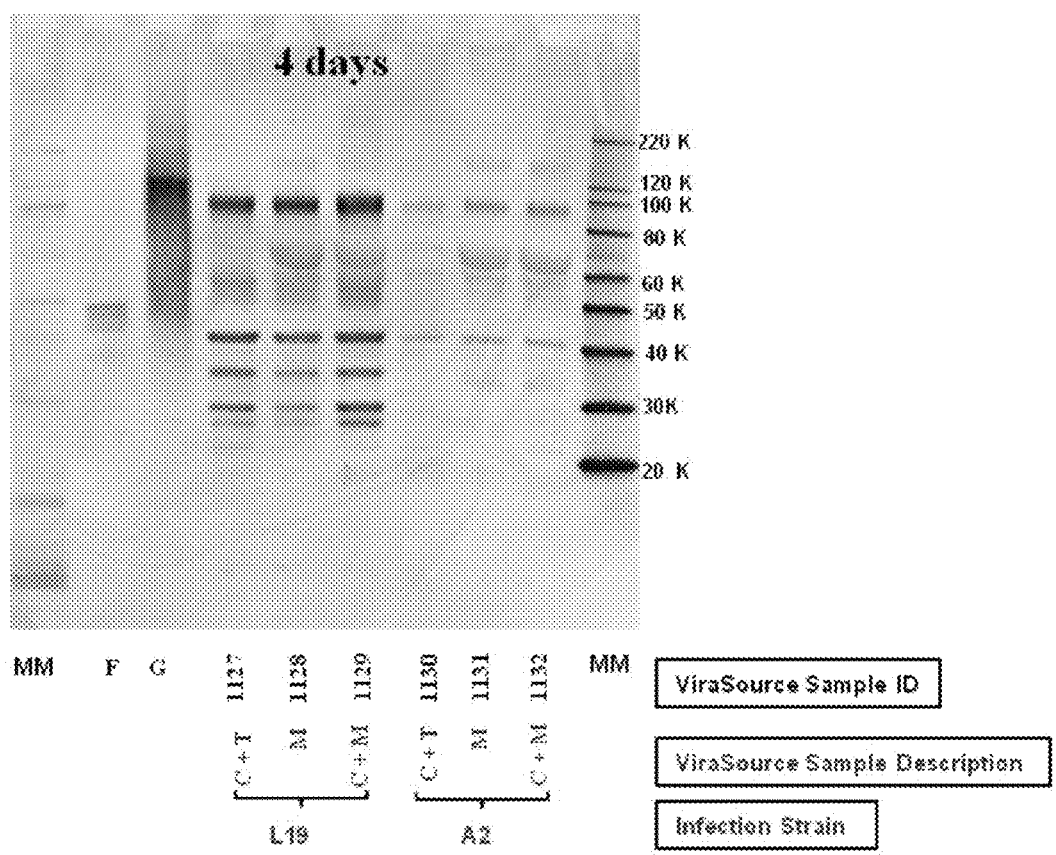

Results: The results are detailed in FIG. 4, which shows a Western blot of HRSV L19 and A2 F and G protein expression 24 hours after virus infection. In addition, Table 8 below shows a density analysis of HRSV F and G protein band from Western Blot.

In addition, both cell-associated viral particles and culture media-associated viral particles express much higher G in L19 infected cells compared to those infected with RSV A2 strain.

Example 3

The purpose of this example was to demonstrate the associated of a nanoemulsion with viral antigen.

Materials and Methods: Transmission Electron Micrographs and Sectioning Technique Twenty mL of the nanoemulsion adjuvant alone or with Fluzone® was fixed with 1% (w/v) osmium tetroxide solution. The fixed preparations were mixed with histogel in 1:10 ratio to form a solid mass. The solid mixture of was sliced into thin 1 mm slices and rinsed with double distilled deionizer water. The cross-sectioned samples were dehydrated with ascending concentrations (30%, 50%, 70%, 90%, 100%) of component A of the Durcupan® kit (Fluka, EM #14020) in double distilled deionizer water. These samples were transferred into embedding solution (mixture of components A, B, C and D) of the Durcupan® kit. The embedded samples were sectioned to a 75 nm thickness and placed on 300 mesh carbon-coated copper grid. The sections on the grids were stained with saturated uranyl acetate in distilled and deionizer water (pH 7) for 10 minutes followed by lead citrate for 5 minutes. The samples were viewed with a Philips CM-100 TEM equipped with a computer controlled compustage, a high resolution (2K×2K) digital camera and digitally imaged and captured using X-Stream imaging software (SEM Tech Solutions, Inc., North Billerica, Mass.).

Results: Electron Micrographs: Cross sectioned TEM of 20% $W_{80}5EC$ nanoemulsion showed nanoemulsion droplets with a uniform inner core material. Nanoemulsion vaccine containing 30 µg of HA shows discrete antigen materials/particles inside the oil core of the droplets that represent the Fluzone® antigens. Since the antigen is incorporated in the core, and is surrounded by the core material, it is protected from staining by the electron dense stain. This leads to a

TABLE 8

HRSV F and G Protein Band Density Analysis From Western Blot

| | | 24 hours After Infection | | | | 4 Days After Infection | | | | | |
|---|---|---|---|---|---|---|---|---|---|---|---|
| | | ViraSource Sample ID | | | | | | | | | |
| | | 1123 | 1124 | 1125 | 1126 | 1127 | 1128 | 1129 | 1130 | 1131 | 1132 |
| | | Virus Strain | | | | | | | | | |
| | | L19 | | A2 | | L19 | | | A2 | | |
| Sample Description | | C + T | C + M | C + T | C + M | C + T | M | C + M | C + T | M | C + M |
| Band Density | G (90 kDa) | 37130.4 | 39563.9 | 5076.6 | 15489.7 | 70377.4 | 70980.1 | 89469.8 | 5986.2 | 18172.8 | 19615.9 |
| | F2 (44-45 kDa) | 24309.2 | 22565.8 | 2160.4 | 7173.5 | 34428.1 | 25094.9 | 41726.3 | 6994.2 | 9542.6 | 7122.8 |
| Concentration (µg/mL) | G (90 kDa) | 7.7 | 8.2 | 1.1 | 3.2 | 8.9 | 9.0 | 11.4 | 0.8 | 2.3 | 2.5 |
| | F2 (44-45 kDa) | 36.8 | 34.1 | 3.3 | 10.9 | 32.5 | 23.7 | 39.4 | 6.6 | 9.0 | 6.7 |

Figure 6:
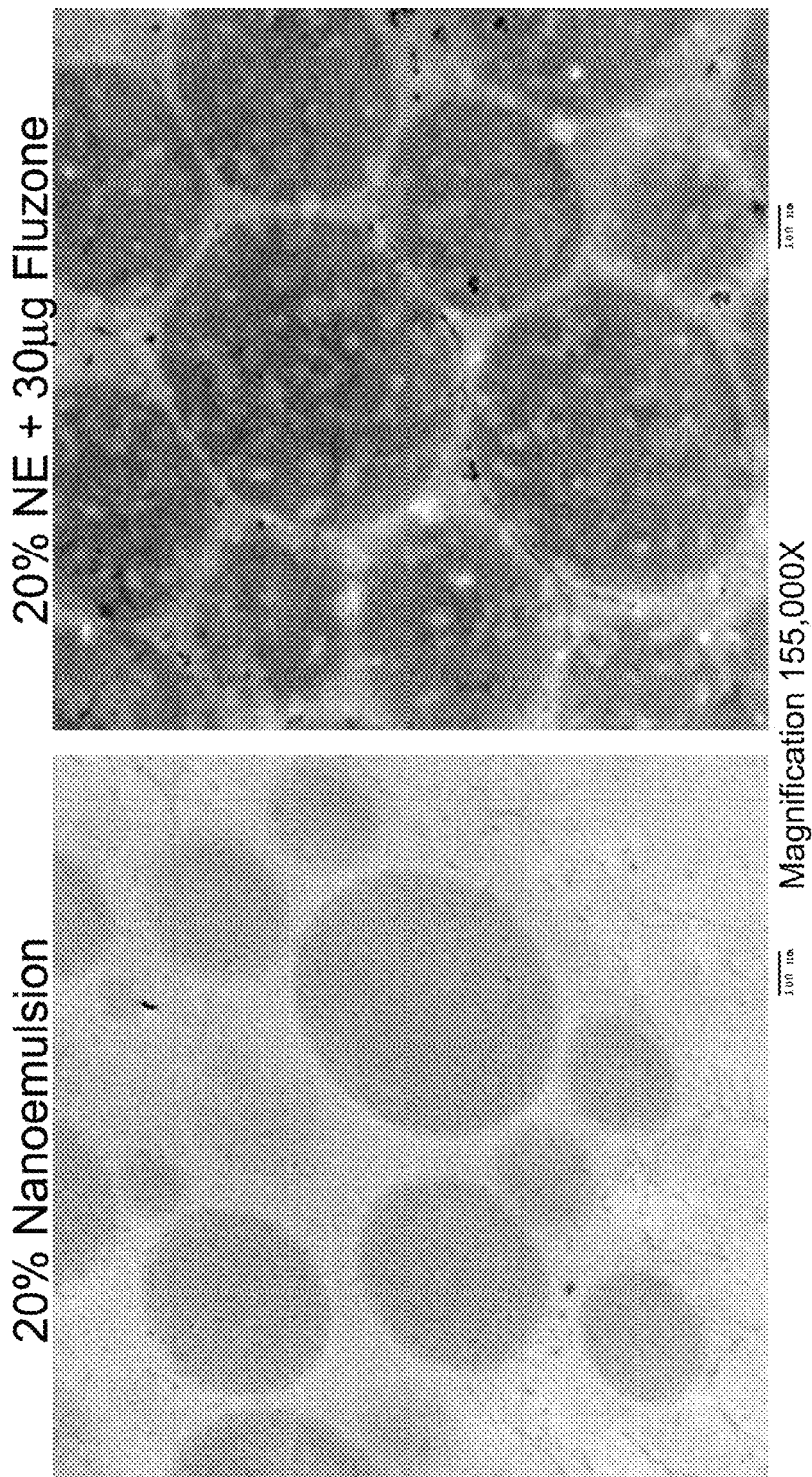

Summary: Both cell-associated viral particles and culture media-associated viral particles express much higher F (about 6 fold average) in L19 infected cells as compared to those infected with RSV A2 strain.

white counter staining effect in the core. The localization of the antigen within the core shields the antigen-sensitive protein subunits in the emulsion, and may protect the antigen from degradation, and thus enhancing stability. There are very few Fluzone® particles outside of the NE particles that were stained dark in color (FIGS. 6a and 6b).

Example 4

The purpose of this example was to compare several different approaches for inactivation of RSV, including β-propiolactone and $W_{80}5EC$ Nanoemulsion, via nasal vaccination in a mouse.

Methods: $W_{80}5EC$, an oil-in-water nanoemulsion with both antiviral and adjuvant activity, was compared with β-propiolactone (β-PL) inactivated virus (strain L19 @2×105 pfu/dose). The two vaccines were administered intranasally (IN) to BALB/C mice at weeks 0 and 4. Mice were bled prior to dosing and at 3 weeks post-boost and then tested for specific antibodies against F-protein.

Animals were challenged nasally with 1×10$^5$ pfu RSV L19 at week 8 and checked for airway hyper-reactivity (AHR), lung cytokines, and viral protein mRNA clearance using PCR.

Results: Both $W_{80}5EC$ and β-PL completely inactivated RSV and induced an immune response. β-PL vaccine induced higher antibody response compared to nanoemulsion-inactivated vaccine (p=0.006). Animals vaccinated with nanoemulsion-inactivated vaccine, however, had higher clearance of the RSV following the challenge, evidenced by lower proteins F and G mRNA in the lungs (p=0.06 and 0.0004, respectively). Moreover, animals receiving nanoemulsion-inactivated vaccine demonstrated a significant lower AHR (p=0.02). Both vaccines induced significant levels of lung IL-17 as compared to nonvaccinated control (<0.01), however, significantly higher levels were induced by nanoemulsion-inactivated vaccine (p=0.009).

Conclusions: β-PL inactivated RSV virus vaccine is associated with AHR following viral challenge in a mouse model of RSV infection. In contrast, nanoemulsion viral inactivation produced no AHR and induced a significantly increased IL-17 production and improved viral clearance. This suggests a novel pathway of immune protection that may provide benefit for vaccination against RSV.

Example 5

The purpose of this example is to describe exemplary nanoemulsions useful as adjuvants for an RSV vaccine.

A total of 10 nanoemulsion formulations were evaluated in mice and cotton rats. $W_{80}5EC$ alone, six $W_{80}5EC$+Poloxamer 407 and Poloxamer 188 (P407 and P188) formulations as well as two $W_{80}5EC$+Chitosan and one $W_{80}5EC$+Glucan formulation have been produced and assessed for stability over 2 weeks under accelerated conditions at 40° C. (Table 1). All 10 nanoemulsions were stable for at least 2 weeks at 40° C.

TABLE 9

$W_{80}5EC$ Formulations

| Nanoemulsion (lot) | Ratios: CPC:Tween: Poloxamer | Method of Addition of Poloxamer | Particle Size (nm) | Zeta Potential (mV) | pH |
|---|---|---|---|---|---|
| $W_{80}5EC$ | 1:6 | — | 450 | 60 | 4.9 |
| $W_{80}5EC$ + 3% P407 (AX1e-221-21-03) | 1:6 | External | 500 | 56 | 5.9 |

TABLE 9-continued $W_{80}5EC$ Formulations

| Nanoemulsion (lot) | Ratios: CPC:Tween: Poloxamer | Method of Addition of Poloxamer | Particle Size (nm) | Zeta Potential (mV) | pH |
|---|---|---|---|---|---|
| $W_{80}5EC$/P407 (AC1e-221-02) | 1:5:1 | Internal | 391 | 46 | 5.5 |
| $W_{80}5EC$/P407 (AC1e-221-01) | 1:1:5 | Internal | 253 | 36 | 5.2 |
| $W_{80}5EC$/P188 (AO1e-221-04) | 1:5:1 | Internal | 526 | 54 | 5.1 |
| $W_{80}5EC$/P188 (AO1e-221-34) | 1:3:3 | Internal | 416 | 54 | 5.7 |
| $W_{80}5EC$/P188 (AO1e-221-03) | 1:1:5 | Internal | 370 | 47 | 5.2 |
| $W_{80}5EC$ + 0.3% Chitosan LMW (AX1e-221-23-3) | 1:6 | External | 505 | 60 | 5.7 |
| $W_{80}5EC$ + 0.3% Chitosan MMW (AX1e-221-3-04) | 1:6 | External | 523 | 60 | 5.4 |
| $W_{80}5EC$ + 0.03% β(1,3) Glucan (AX1e-221-23-02) | 1:6 | External | 491 | 41 | 6.3 |

The following formulations were specifically tested in cotton rat IN studies: (1) Formulation 1, $W_{80}5EC$ (NE80), comprising: (a) CPC/Tween 80 (ratio of 1:6), and (b) Particle size ~500 nm (Table 10); and Formulation 2, $W_{80}P_{188}5EC$ (NE188), comprising: (a) CPC/Tween 80/P188 (ratio of 1:1:5), (b) Particle size ~300 nm, (c) enhanced mucoadhesiveness (IN), and (d) enhanced residence time (IM) (Table 11).

TABLE 10

Formulation 1
Composition of 60% $W_{80}5EC$ adjuvant

| Ingredient | w/w % |
|---|---|
| Distilled water | 54.1 |
| CPC | 0.64 |
| Tween 80 | 3.55 |
| Ethanol | 4.04 |
| Soybean oil | 37.7 |

TABLE 11

Formulation 2
Composition of 60% $W_{80}P_{188}5EC$ adjuvant

| Ingredient | w/w % |
|---|---|
| Distilled water | 54.1 |
| CPC | 0.64 |
| Tween 80 | 0.6 |
| Poloxamer 188 | 3 |
| Ethanol | 4.03 |
| Soybean oil | 37.7 |

Example 6

The purpose of this example is to describe RSV viral strains useful in the vaccines of the invention.

NanoBio obtained and evaluated a novel L19 RSV strain to test as an antigen in the nanoemulsion inactivated/nanoemulsion adjuvanted RSV vaccine. This strain was found to cause infection and enhanced respiratory disease (ERD) in mice. Moreover, data published showed that it conferred protection without induction of ERD in mice when formulated with nanoemulsion. This L19 strain was compared to a Wildtype A2 strain obtained from the American Type Culture Collection (ATCC).

The RSV Strain L19 isolate was isolated from an RSV-infected infant with respiratory illness in Ann Arbor, Mich. on 3 Jan. 1967 in WI-38 cells and passaged in SPAFAS primary chick kidney cells followed by passage in SPAFAS primary chick lung cells prior to transfer to MRC-5 cells (Herlocher 1999) and subsequently Hep2 cells (Lukacs 2006). Comparison of RSV L19 genome (15,191-nt; GenBank accession number FJ614813) with the RSV strain A2 (15,222-nt; GenBank accession number M74568) shows that 98% of the genomes are identical. Most coding differences between L19 and A2 are in the F and G genes. Amino acid alignment of the two strains showed that F protein has 14 (97% identical) and G protein has 20 (93% identical) amino acid differences.

RSV L19 strain has been demonstrated in animal models to mimic human infection by stimulating mucus production and significant induction of IL-13 using an inoculum of $1 \times 10^5$ plaque forming units (PFU)/mouse by intra-tracheal administration (Lukacs 2006).

Rationale for Selection of RSV L19 Strain: NanoBio developed and optimized RSV propagation and purification methods for three viral strains grown in Vero cells and has established multiplicity of Infection (MOI), optimized purification and concentration of the antigen using PEG6000 precipitation and ultracentrifugation. Importantly and uniquely, the RSV L19 viral strain is unique in that it produces significantly higher yields of F protein (approximately 10-30 fold more per PFU) than the other strains. F protein content may be a key factor in immunogenicity and the L19 strain currently elicits the most robust immune response. The L19 strain has a shorter propagation time and therefore will be more efficient from a manufacturing perspective. NanoBio proposes to produce RSV L19 strain virus for the vaccine in a qualified Vero cell line following single plaque isolation of the L19 strain and purification of the virus to establish a Master Viral Seed Bank and Working Viral Seed Bank. The results comparing the three viral strains are provided in Table 12.

TABLE 12

Comparison of RSV Strains

| RSV Strain | Days of Propagation | RSV F protein (µg/mL) | RSV G protein (µg/mL) | G/F Ratio | Viral Titer (PFU/mL) |
|---|---|---|---|---|---|
| L19 | 4-5 | 110 | 603 | 5.5 | $0.5 \times 10^7$ |
| A2 Wild Type[1] | 4-5 | 44 | 108 | 2.5 | $1.9 \times 10^7$ |
| rA2cp248/404[2] | 8-9 | 38 | 284 | 7.5 | $0.5 \times 10^8$ |

[1]ATCC (strain number VR-1540). Virus was isolated from an RSV infected infant with respiratory illness in Melbourne, Australia in 1961 and has been propagated in HEp-2 cell culture at least 27 times (Lewis 1961). This virus has been treated to remove adenovirus from the original deposit and has been utilized as a challenge strain in human clinical trials (Lee 2004).
[2]Recombinant temperature-sensitive A2 mutant virus obtained from the NIH (Whitehead 1998).

Example 7

The purpose of this example is to describe Inactivation of RSV L19 viral strain with different nanoemulsion adjuvants.

The nanoemulsions (1) $W_{80}5EC$, (2) $W_{80}5EC$ with P407; (3) $W_{80}5EC$ with P188, (4) $W_{80}5EC$ with high and low molecular weight Chitosan, and (5) $W_{80}5EC$ with Glucan, have been tested with the RSV L19 viral strain to determine viral inactivation.

Figure 7:
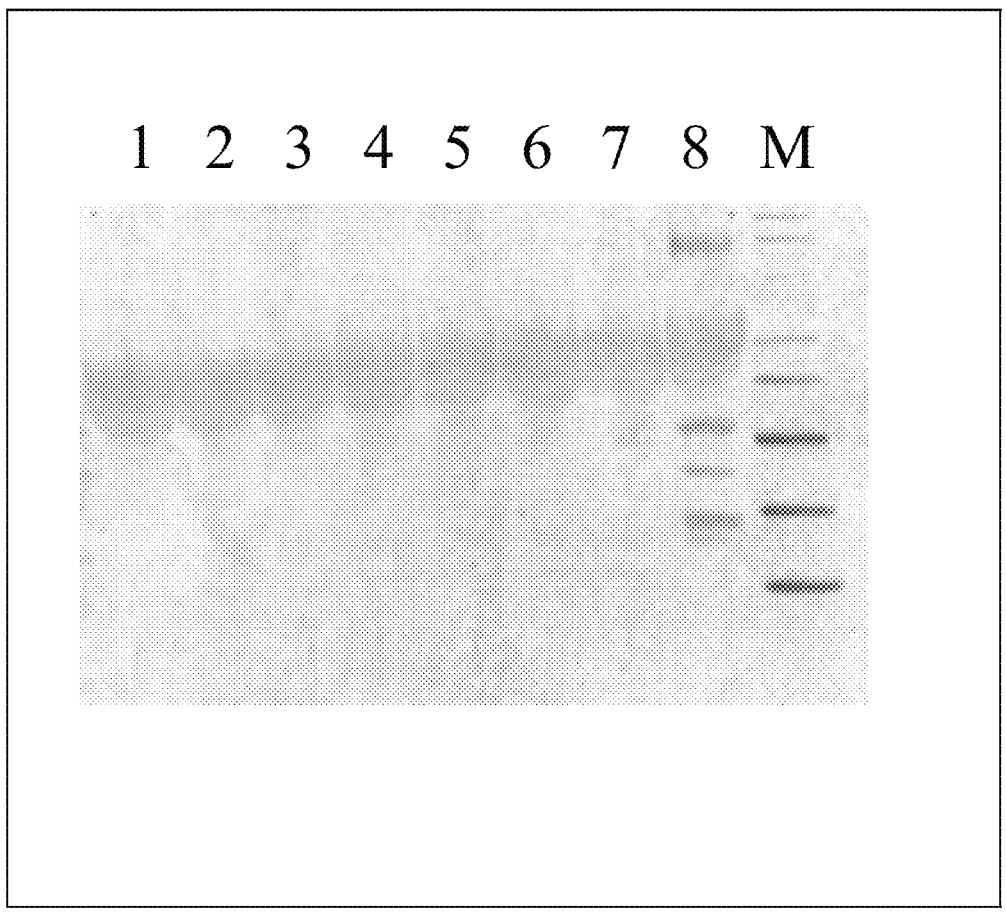

Inactivation with 20% nanoemulsion was performed for 2 hours at room temperature and with 0.25% βPL for 16 hours at 4° C. followed by 2 hours at 37° C. The treated virus was passaged three times in Hep-2 cells and Western blot analysis was performed on cell lysate to determine presence of live virus. See FIG. 7. In particular, FIG. 7 shows the viral inactivation by Western blot assessment, with lanes containing: (1) $W_{80}5EC$ (Lane 1), (2) $W_{80}5EC+0.03\%$ B 1,3 Glucan (lane 2), (3) $W_{80}5EC+0.3\%$ Chitosan (medium molecular weight)+acetic acid (lane 3), (4) $W_{80}5EC+0.3\%$ P407 (lane 4), (5) $W_{80}5EC+0.3\%$ Chitosan (low molecular weight)+0.1% acetic acid (lane 5), (6) media alone (lane 6); (7) βPL-inactivated virus (lane 7), and (8) L19 positive control (lane 8).

RSV L19 was completely inactivated by the nanoemulsion formulations evaluated and by βPL. FIG. 7 shows that three consecutive passages of the NE-treated virus in a cell culture resulted in no detected viral antigen when blotted against RSV antibodies in a western blot. This three cell culture passage test is well established and accepted method for determining viral inactivation. Of note, all lanes in FIG. 7 have a thick background band, which is not a viral band, but is bovine serum albumin. Viral proteins can be detected only in the positive control (lane 8).

Example 8

The purpose of this example was to evaluate the short term stability of RSV vaccines.

Target doses of RSV L19 viral preparations were formulated to achieve a final nanoemulsion concentration of 20%. Vaccine was stored at RT and at 4° C. Stability test parameters included physical and chemical analysis (Table 13).

TABLE 13

Stability Test Parameters

| Stability Test | Acceptance Criteria |
|---|---|
| Physical Appearance | No separation |
| Mean Particle Size | ±10% of initial size |
| Zeta Potential | ±10% of initial charge |
| Western Blot | No change in G band intensity |

Physical appearance, mean particle size, zeta potential and Western Blot acceptance criteria with RSV strain L19 were met following 14 days of storage (longest tested) at RT and 4° C. with $W_{80}5EC+/-$βPL inactivation. $W_{80}5EC+3\%$ P407, $W_{80}5EC+0.3\%$ Chitosan-LMW, and $W_{80}5EC+0.3\%$ Chitosan-MMW were tested for a maximum of 7-8 days and also demonstrated stability. The $W_{80}5EC/P188$ (1:1:5) and $W_{80}5EC/P188$ (1:5:1) formulations were also tested with a live virus RSV A2 strain as opposed to RSV L19 strain for a maximum of 14 days; the 1:1:5 formulation demonstrated stability whereas the 1:5:1 formulation demonstrated potential agglomeration (Table 14).

TABLE 14

Vaccine Stability by Physical and Chemical Parameters and Western Blot

| Adjuvant Lot # | Viral Strain | Starting Adjuvant Composition (60%) | Condition | Z-average (nm) | # of peaks | PDI | Zeta Potential (mV) | Stability Based on G Protein pass/fail |
|---|---|---|---|---|---|---|---|---|
| 566DX01 | βPL inactivated L19 | Reference $W_{80}5EC$ (1:6) | Fresh | 542.1 | 2 | 0.199 | 41.5 | NA |
| | | | 4° C.-14 d | 548.6 | 2 | 0.241 | 43.5 | Pass |
| | | | RT-14 d | 538.6 | 2 | 0.210 | 40.7 | Pass |
| 556DX01 | L19 | Reference $W_{80}5EC$ (1:6) | Fresh | 588.5 | 2 | 0.234 | 39.3 | NA |
| | | | 4° C.-14 d | 545.9 | 2 | 0.210 | 39.9 | Pass |
| | | | RT-14 d | 535.6 | 2 | 0.234 | 41.1 | Pass |
| NB-221-21-03 | L19 + PEG | $W_{80}5EC$ + 3% P407 (external addition) | Fresh | 779.3 | 1 | 0.351 | 20.1 | NA |
| | | | 4° C.-8 d | 654.8 | 1 | 0.313 | 30.4 | Pass |
| | | | RT-8 d | 763.2 | 1 | 0.313 | 30.2 | Pass |
| NB-221-23-03 | L19 + PEG | $W_{80}5EC$ + 0.3% Chitosan-LMW External Addition | Fresh | 557.2 | 1 | 0.253 | 60.1 | NA |
| | | | 4° C.-7 d | 534.7 | 1 | 0.234 | NA | Pass |
| | | | RT-7 d | 534.7 | 1 | 0.229 | 62.4 | Pass |
| NB-221-23-04 | L19 + PEG | $W_{80}5EC$ + 0.3% Chitosan-MMW External Addition | Fresh | 528.4 | 1 | 0.226 | NA | NA |
| | | | 4 C.-7 d | 532.0 | 1 | 0.229 | 63.5 | Pass |
| | | | RT-7 d | 568.0 | 1 | 0.254 | 64.9 | Pass |
| AO1e-221-03 | A2 | $W_{80}5EC/P188$ (1:1:5) | Fresh | 229.5 | 1 | 0.108 | 27.0 | NA |
| | | | 4° C.-14 d | 259.0 | 2 | 0.206 | 27.0 | Pass |
| | | | RT-14 d | 249.9 | 2 | 0.161 | 20.4 | Pass |
| AO1e-221-04 | A2 | $W_{80}5EC/P188$ (1:5:1) | Fresh | 396.1 | 2 | 0.164 | 37.1 | NA |
| | | | 4° C.-14 d | 5544.0* | 2 | 0.619 | −4.3* | Pass |
| | | | RT-14 d | 2010.0* | 2 | 0.753 | −17.1* | Pass |

*potential agglomeration

Figure 8:
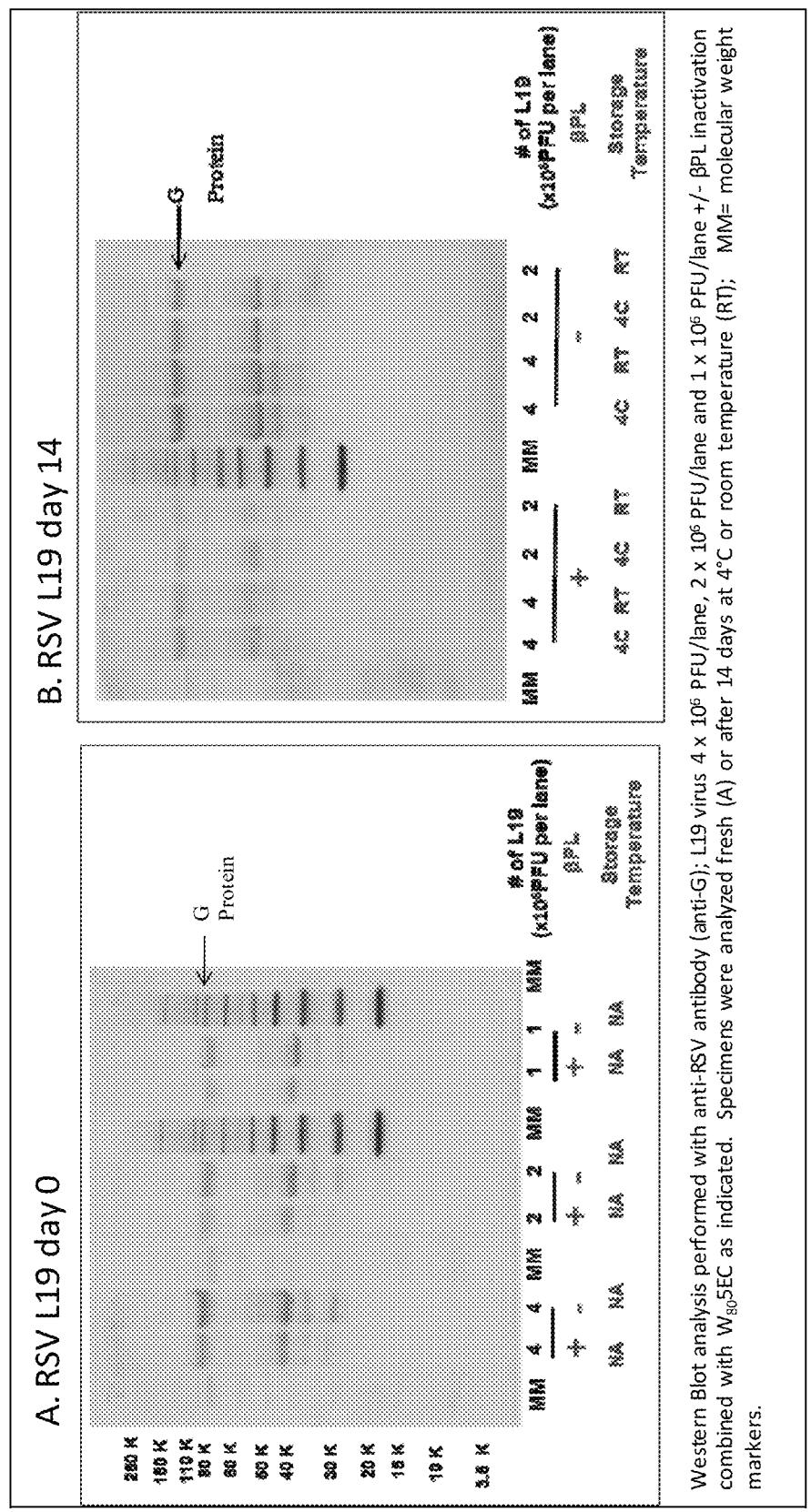

FIG. 8 shows an example of G band intensity of RSV strain L19 with $W_{80}5EC$+/−βPL inactivation by Western blot at day 0 (FIG. 8A) and following 14 days of storage at RT or 4° C. (FIG. 8B). In particular, FIG. 8 shows a Western blot analysis performed with anti-RSV antibody (anti-G); L19 virus $4\times10^6$ PFU/lane, $2\times10^6$ PFU/lane, and $1\times10^6$ PFU/lane+/−βPL inactivation combined with $W_{80}5EC$ as indicated. Specimens were analyzed fresh (FIG. 8A) or after 14 days at 4° C. or room temperature (RT) (FIG. 8B).

Example 9

The purpose of this example was to evaluate the immunogenicity of an RSV vaccine in mice.

Mice were immunized intramuscularly as shown in Table 15. Mice received 50 μl of RSV adjuvanted vaccine IM at 0 weeks. Mice were bled on 0 and 3 weeks and tested for serum antibodies. Chitosan was used as an immune-modulator to enhance the immune response in addition to the adjuvant activity contributed to the nanoemulsion.

TABLE 15

Different arms used in vaccination of the mice

| Arm # | Virus Preparation | NE formulation | # of animals |
|---|---|---|---|
| 1 | RSV L19 - 2 μg F | 2.5% $W_{80}5EC$ + 0.1% Low Mol. Wt. Chitosan | 10 |
| 2 | RSV L19 - 2 μg F | 5% $W_{80}5EC$ | 10 |
| 3 | RSV L19 - 2 μg F | 2.5% $W_{80}5EC$ | 10 |
| 4 | RSV L19 - 2 μg F βPL inactivated | None | 10 |
| 5 | Naive—No vaccine | | 10 |

Figure 9:
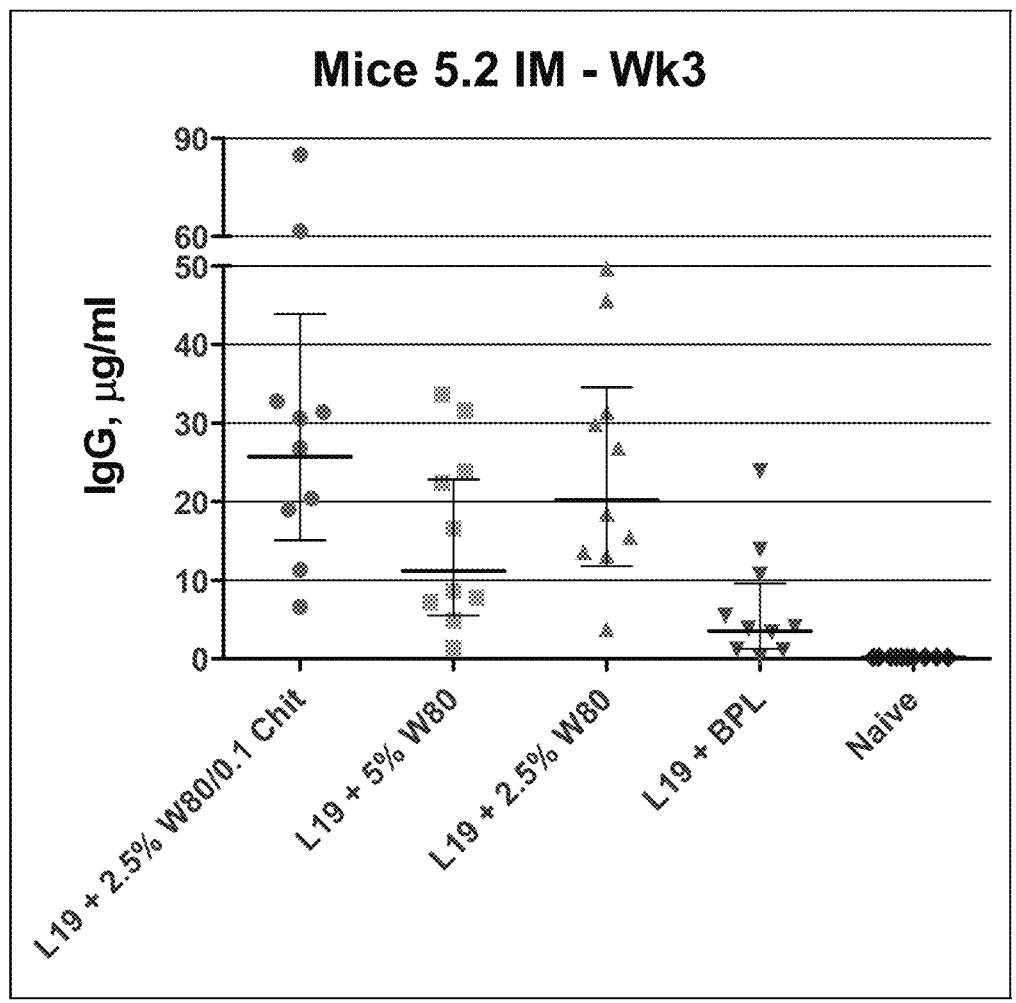

Mice vaccinated with nanoemulsion containing chitosan showed more enhanced immune response following a single dose of nanoemulsion adjuvanted RSV vaccine when compared to nanoemulsion without chitosan (FIG. 9). In particular, FIG. 9 shows the immune response (IgG, μg/ml) at week 3 following vaccination in mice vaccinated IM with different nanoemulsion formulations with and without chitosan: (1) RSV strain L19+2.5% $W_{80}5EC$+0.1% Low Mol. Wt. Chitosan; (2) RSV strain L19+5% $W_{80}5EC$; (3) RSV strain L19+2.5% $W_{80}5EC$; (4) RSV strain L19+βPL inactivated virus; and (5) naive mice (no vaccine). The results depicted in FIG. 9 show the highest levels of IgG were found in mice vaccinated with RSV strain L19+2.5% $W_{80}5EC$+0.1% Low Mol. Wt. Chitosan, with the next highest levels of IgG found in mice vaccinated with RSV strain L19+2.5% $W_{80}5EC$, followed by mice vaccinated with RSV strain L19+5% $W_{80}5EC$. The lowest levels of IgG observed in vaccinated mice were for RSV strain L19+βPL inactivated virus.

Example 10

The purpose of this example was to determine the immunogenicity of RSV vaccines according to the invention in Cotton rats.

Cotton rats are the accepted animal species for evaluating immunogenicity and efficacy of RSV vaccines. Using data generated in mice, two nanoemulsions were selected for evaluation in Cotton rats. The two initial formulations studied include the $W_{80}5EC$ and the $W_{80}P_{188}5EC$ (1:1:5) (see Tables 10 and 11 above).

Figure 10:
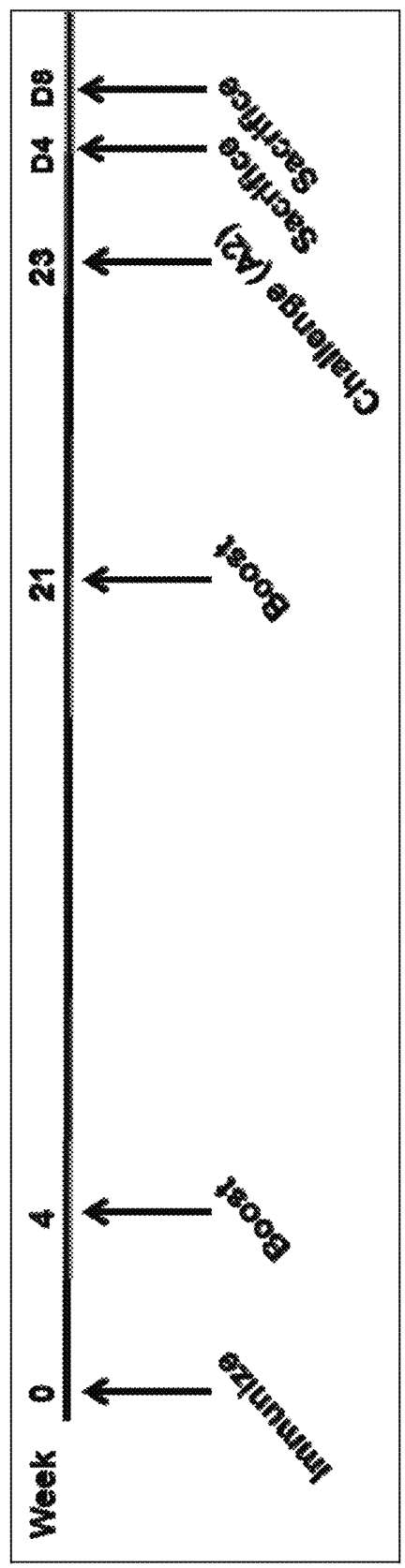

Cotton rats received two doses of 30 μl IN of the nanoemulsion-adjuvanted vaccine containing 6.6 μg F-ptn. They were challenged with $5\times10^5$ pfu RSV strain A2 at week 23. Half of the animals were sacrificed at day 4 and half were sacrificed on day 8. The vaccination schedule is demonstrated in FIG. 10.

Figure 11:
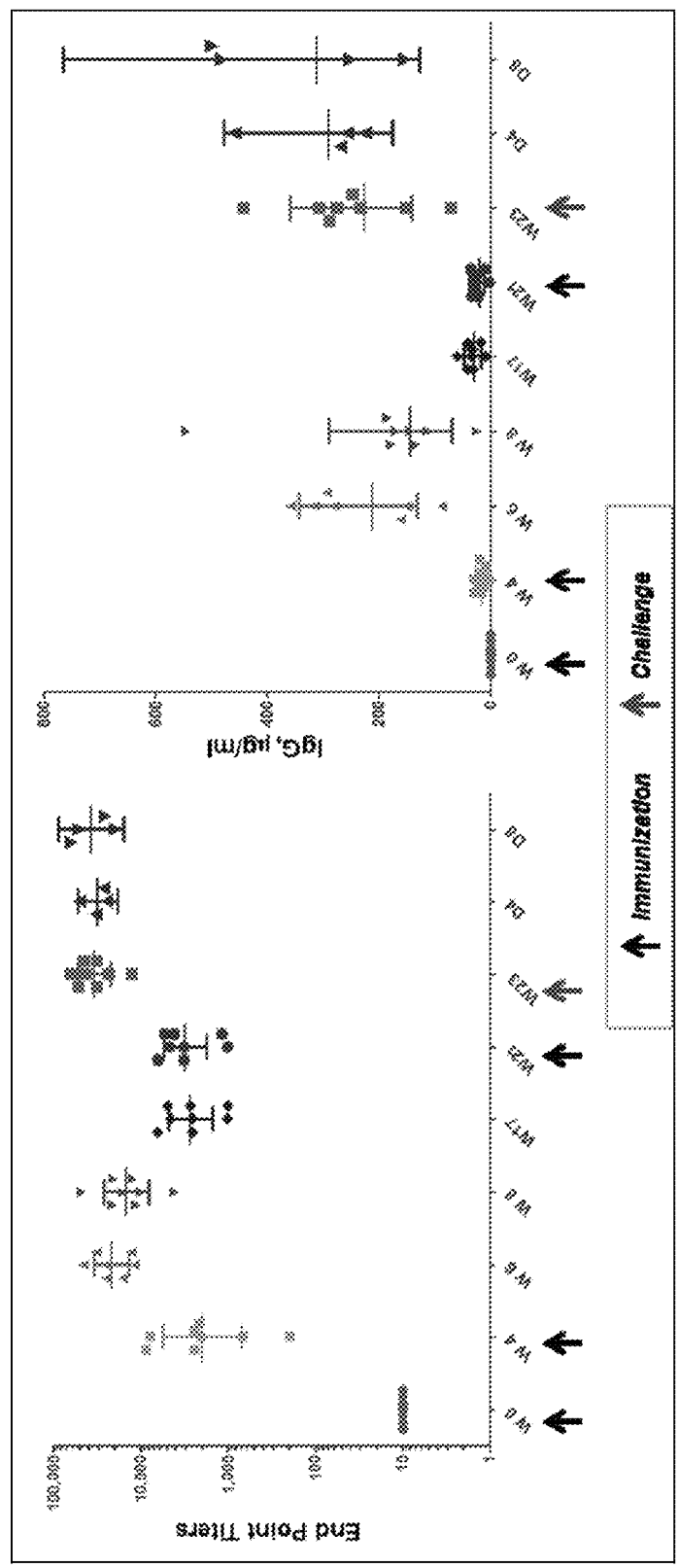
Figure 12:
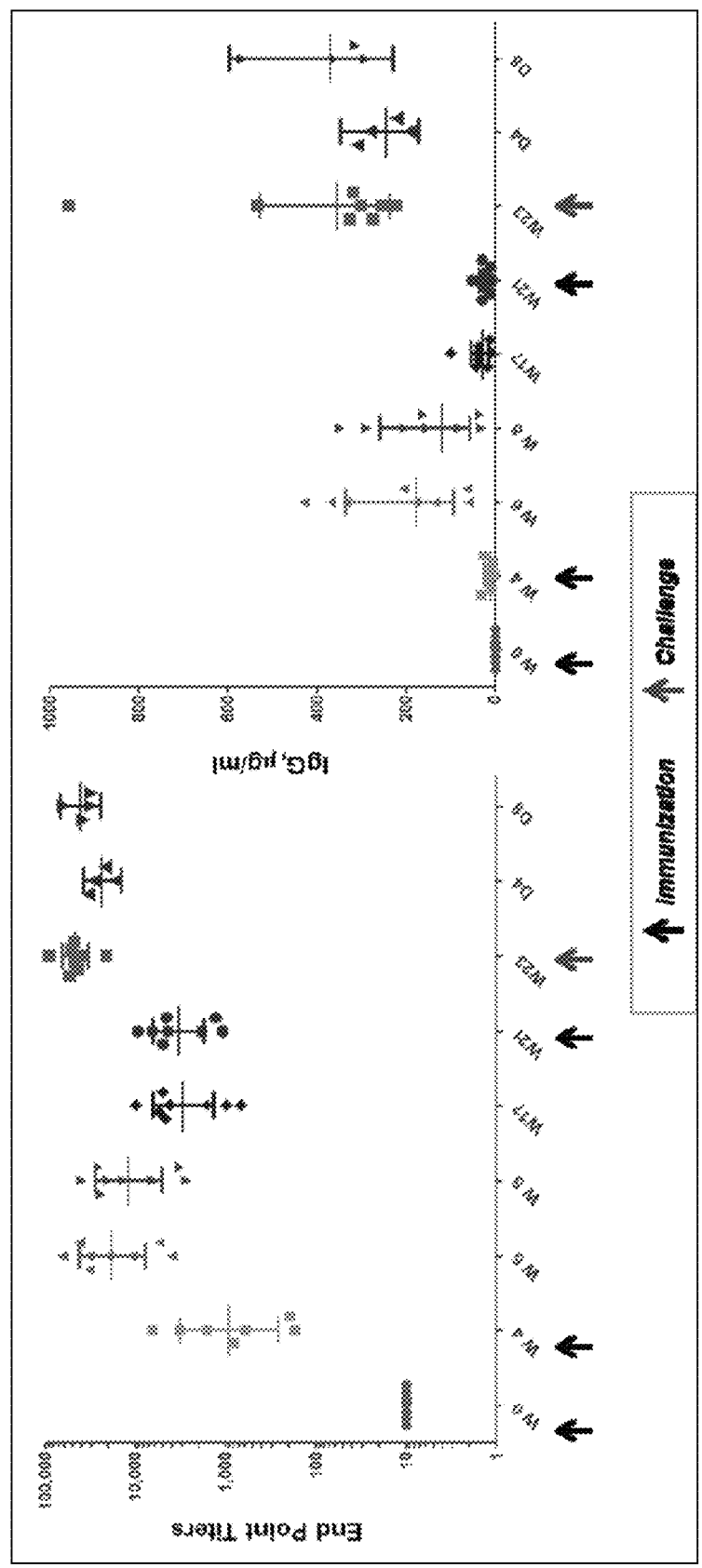

Immunogenicity data presented below show that upon IN immunization with an RSV-nanoemulsion vaccine, a positive immune response was observed. Upon the administration of the second dose, a rapid and significant increase in antibody titers were achieved. Data presented in FIG. 11 show that at week 21, the antibody level in all animals was about one tenth of the maximal values obtained shortly after the administration of the first boost at week 4. Administration of a second boost prior to the challenge yielded an immune response that was almost identical to levels achieved at week 6, two weeks after the first boost. Both nanoemulsions were equally efficient in eliciting a strong and significant immune responses (FIGS. 11 and 12). (The Y axis in FIGS. 11 and 12 shows the end point titers or antibody quantity of specific antibody to F protein and the X axis shows the time period in weeks.)

ELISA Unit/µg/ml:

The amount of specific antibody to F protein was calculated by area under the curve in the ELISA in relation to a defined reference serum which was assigned an arbitrary 100 EU.

Example 11

The purpose of this example was to determine the effect of RSV vaccines according to the invention on neutralizing antibodies, as well as cross-reactivity of an RSV vaccine comprising RSV strain L19 against other RSV strains following IN administration.

Cotton rats were vaccinated with 30 µl of vaccine intranasally, boosted at 4 weeks, and bled at 0, 4, 6, and 8 weeks. Animals were challenged at week 23 with $5\times10^5$ pfu of RSV strain A2. Study groups included two groups that received 20% $W_{80}5EC$ nanoemulsion mixed with either $1.6\times10^5$ PFU RSV strain L19 containing 3.3 µg F protein (n=8) or $3.2\times10^5$ PFU RSV strain L19 containing 6.6 µg F protein (n=8), as well as two groups that received 20% $W_{80}P_{188}5EC$ nanoemulsion mixed with either $1.6\times10^5$ PFU RSV strain L19 containing 3.3 µg F protein (n=8) or $3.2\times10^5$ PFU L19 RSV containing 6.6 µg F protein (n=8).

Figures 13, 13A, 13B:
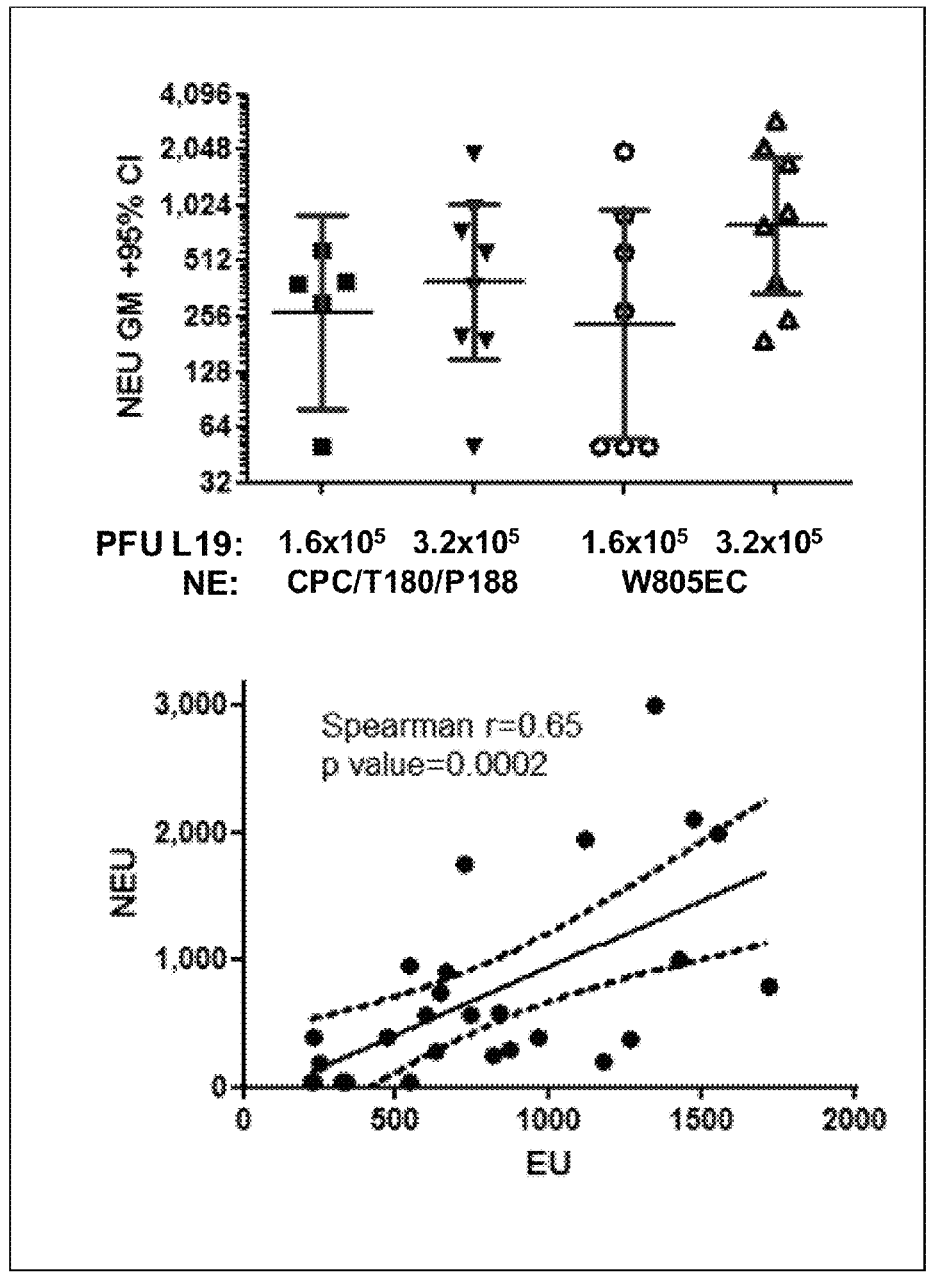

Half of the animals were sacrificed at Day 4 and half at Day 8. Individual cotton rats sera was tested for neutralizing antibodies. Neutralization units (NEU) represent a reciprocal of the highest dilution that resulted in 50% plaque reduction. NEU measurements were performed at 4 weeks (pre boost) and at 6 weeks (2 weeks post boost). Specimens obtained at 6 weeks generated humoral immune responses adequate to allow for NEU analysis. Data is presented as geometric mean with 95% confidence interval (CI) (FIG. 13A). Correlation between EU and NEU is for all animals at 6 weeks using Spearman rho (FIG. 13B).

Specifically, FIG. 13 shows neutralizing antibody titers at 6 weeks time point (FIG. 13A). It is noteworthy that all animals vaccinated with $3.2\times10^6$ PFU RSV strain L19 inactivated with 60% $W_{80}5EC$ or 60% $W_{80}P1885EC$ generated robust neutralizing antibodies. There is a statistically significant positive correlation between EU and neutralizing antibodies (NEU) (FIG. 13B).

Neutralization Unit (NU):

The reciprocal of the highest serum dilution that reduces viral plaques by 50%.

Specific Activity (NU/EU):

Viral neutralizing antibody antibodies (NU) per the one EU F-protein antibody (FIG. 13B)

Figures 14, 14A, 14B:
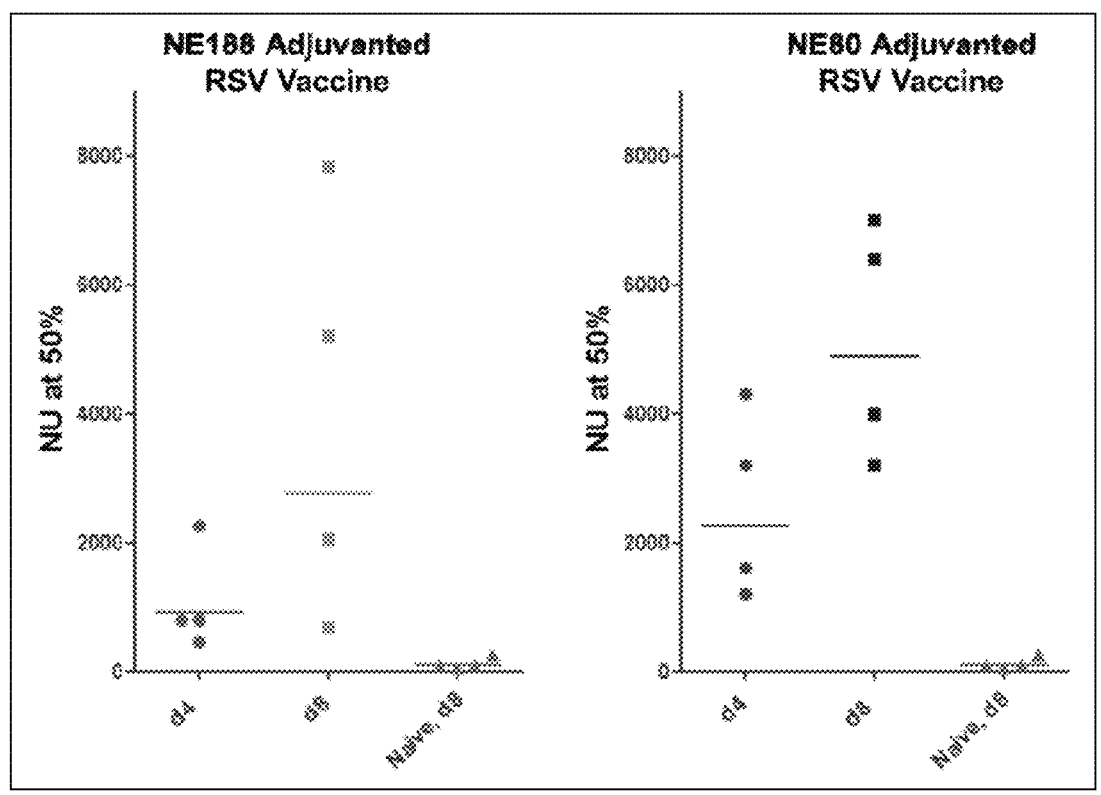

FIG. 14 shows neutralizing antibodies on day 4 and day 8. FIG. 14A shows the results for $W_{80}P1885EC$ nanoemulsion combined with RSV strain L19, and FIG. 14B shows the results for $W_{80}5EC$ nanoemulsion combined with RSV strain L19. All cotton rats demonstrated high neutralizing antibodies (NU) against the vaccine RSV strain L19. Neutralizing antibodies were rising steadily following the challenge (Y axis). Day 8 neutralizing units (NU) were higher than Day 4 NU. Naïve Cotton Rats did not show any neutralization activity in their sera. Serum neutralizing antibodies and specific activity showed a trend to increase from Day 4 to Day 8 post-challenge.

FIG. 15 shows the Specific activity of serum antibodies showed that the specific activity (Neutralizing units/ELISA units) of the serum antibodies tends to increase on Day 8 when compared to Day 4 post-challenge. FIG. 15A shows the results for $W_{80}P1885EC$ nanoemulsion combined with RSV strain L19 (NU/EU for the Y axis), at Day 4 and Day 8. FIG. 15B shows the results for $W_{80}5EC$ nanoemulsion combined with RSV strain L19 (NU/EU for the Y axis), at Day 4 and Day 8. All cotton rats demonstrated high neutralization activity (FIG. 15).

Serum of vaccinated cotton rats showed cross protection against RSV strain A2 (in addition to RSV strain L19) on Day 4 post-challenge (FIG. 16). Specifically, FIG. 16 shows cross protection at Day 4 for cotton rats that received 3 doses of RSV L19 adjuvanted vaccine, then challenged with RSV strain A2. FIG. 16A shows the results for $W_{80}P1885EC$ nanoemulsion combined with RSV strain L19, and FIG. 16B shows the results for $W_{80}5EC$ nanoemulsion combined with RSV strain L19. Serum neutralization activity shows equivalent NU against RSV strain L19 or RSV strain A2, demonstrating cross protection between the two RSV strains. Vaccinated cotton rats cleared all challenged RSV virus on Day 4 post challenge when compared with naïve cotton rats (FIG. 17). As expected by day 8 all animals had cleared the virus. Specifically, FIG. 17 shows viral clearance at Day 4 in the lungs of the cotton rats, by measurement of the RSV strain A2 viral titer (PFU/g) in the lungs of the tested cotton rats. Vaccinated cotton rats (vaccinated with $W_{80}P_{188}5EC$ nanoemulsion combined with RSV strain L19, and $W_{80}5EC$ nanoemulsion combined with RSV strain L19), showed complete clearance of RSV strain A2 challenged virus from the lungs of the cotton rats. In contrast, naïve animals shows $>10^3$ pfu RSV strain A2/gram of lung (limit of detection was $2.1\times10^1$ pfu/g).

Example 12

The purpose of this example was to evaluate Intramuscular vaccination of RSV vaccines according to the invention in Cotton Rats.

Cotton rats were vaccinated IM according to the schedule shown in FIG. 18. Animals received 50 µl RSV adjuvanted RSV vaccine containing 3.3 µg F-protein (20% $W_{80}5EC$ nanoemulsion mixed with $1.6\times10^5$ PFU RSV strain L19 containing 3.3 µg F protein). Cotton rats produced a specific immune response against RSV. The antibody levels were diminished until a second boost was administered on week 14. There was a slight increase in the antibody levels following the challenge (FIGS. 19 and 20). In particular, FIG. 19 shows the serum immune response in the vaccinated cotton rats. The Y axis shows IgG, µg/mL, over a 14 week period, at day 4 post-challenge, and at day 8 post-challenge. FIG. 20 shows the serum immune response in the vaccinated cotton rats. FIG. 20A shows the end point titers (Y axis) over a 14 week period, at day 4 post-challenge, and at day 8 post-challenge. FIG. 20B shows the ELISA units (Y axis) over a 14 week period, at day 4 post-challenge, and at day 8 post-challenge.

The efficacy of IM immunization was assessed by challenging the animals with a live A2 strain of RSV, which is a strain that causes disease in humans. A dose of $5\times10^5$ pfu of RSV strain A2 was administered to animals two weeks after booster immunization of the RSV L19 nanoemulsion-adjuvanted vaccine. A naïve age-matched group was also challenged. Half of the animals in each group were sacrificed on day 4 post challenge, at which time the maximum viral load was demonstrated in the lungs of Cotton Rats. The other half were sacrificed at day 8.

Viral clearance: Lung culture showed that all vaccinated animals had no virus in their lungs at 4 days post challenge while naïve animals had virus loads of $10^3$ pfu RSV strain A2/g of lung tissue (FIG. 21). Specifically, FIG. 21 shows viral clearance at Day 4 in the lungs of the cotton rats, by measurement of the RSV strain A2 viral titer (PFU/g) in the lungs of the tested cotton rats. Vaccinated cotton rats (vaccinated with $W_{80}5EC$ nanoemulsion combined with RSV strain L19), showed complete clearance of RSV strain A2 challenged virus from the lungs of the cotton rats. In contrast, naïve animals showed viral loads of $10^3$ pfu RSV strain A2/gram of lung or greater (limit of detection was $2.1 \times 10^1$ pfu/g).

Cotton Rat Summary: All RSV vaccines formulated in nanoemulsion and administered IN or IM elicited a protective immune response that prevented infection of immunized animals. Moreover, nanoemulsion-inactivated and adjuvanted RSV L19 vaccines are highly immunogenic in the universally accepted cotton rat model. Cotton rats elicited a rise in antibody titers after one immunization and a significant boost after the second immunization (approximately a 10-fold increase). The antibodies generated are highly effective in neutralizing live virus and there is a linear relationship between neutralization and antibody titers. Furthermore, antibodies generated in cotton rats showed cross protection when immunized with the RSV L19 strain and challenged with the RSV A2 strain. Both IM and IN immunization established memory that can be invoked or recalled after an exposure to antigen either as a second boost or exposure to live virus.

Example 13

The purpose of this example was to compare intranasal (IN) versus intramuscular (IM) administration of a $W_{80}5EC$ nanoemulsion adjuvanted RSV vaccine.

Methods: RSV vaccine containing $2 \times 10^5$ plaque forming units (PFU) of L19 RSV virus with 1.7 µg of F protein was inactivated with 20% $W_{80}5EC$ nanoemulsion adjuvant. BALB/C mice (n=10/arm) were vaccinated at weeks 0 and 4 IN or IM. Serum was analyzed for anti-F antibodies (FIG. 22). Cells from spleens, cervical and intestinal lymph nodes (LN) were analyzed for RSV-specific cytokines (FIG. 23). Mice were challenged oropharyngeally with $5 \times 10^5$ PFU L19 at 8 weeks. Airway hyperreactivity was assessed by plethysmography. Lungs were analyzed day 8 post challenge to assess mRNA of cytokines, viral proteins, and histopathology.

Results: Mice vaccinated IM had higher anti-F antibodies (GM 396 [95% CI-240-652] vs. 2 [95% CI 0-91]) (FIG. 22) and generated more IL-4 and IL-13, after challenge (p<0.05) compared to mice vaccinated IN (FIG. 23). In contrast, IL-17 from spleen cells, cervical LN and intestinal LN was higher after IN vs IM vaccination (GM: 57 vs 1, 119 vs 3 and 51 vs 4 µg/mL, respectively, p<0.05) (FIG. 23). FIG. 24 shows measurement of the cytokines IL-4, IL-13, and IL-17 in lung tissue following either IN or IM vaccination. IL-4 and IL-13 were expressed at higher amounts following IM administration, with IL-17 showing greater expression following IN administration. Upon challenge, both routes of immunization resulted in clearance of F and G proteins, but airway resistance was higher in the IM group (p=0.03) with confirmatory histopathology (FIG. 25). Pulmonary IL-4 and IL-13 had a strong positive correlation (r=0.89; p=0.001 and r=0.8; p=0.007, respectively) with airway hyperreactivity.

Pulmonary IL-17 was only generated in mice vaccinated IN (p=0.008) and had a strong negative correlation (r=−0.81 p=0.007) with airway hyperreactivity.

CONCLUSION

Compared to IM vaccination, IN vaccination with a novel nanoemulsion adjuvant $W_{80}5EC$ resulted in less airway hyperreactivity, strongly correlated with high IL-17 production. IL-17 as generated by mucosal vaccination may be an important marker for reduced airway hyperreactivity in RSV infection.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

FULL CITATIONS FOR DOCUMENTS REFERRED IN THE SPECIFICATION

1. Hacking, D., Hull, J. 2002. Respiratory syncytial virus-virus biology and host response. J. Infection. 45: 18-24.
2. Graham, B. 2011. Biological challenges and technological opportunities for respiratory syncytial virus vaccine development. Immunological Reviews. 239: 149-166.
3. Kruijens D., Schijf, M. 2011. Local innate and adaptive immune responses regulate inflammatory cell influx into the lungs after vaccination with formalin inactivated RSV. Vaccine. 29: 2730-2741.
4. Swanson, K., Settembre, E. 2011. Structural basis for immunization with postfusion respiratory syncytial virus fusion F glycoprotein (RSV F) to elicit high neutralizing antibody titers. PNAS. 108: 9619-9624.
5. McLellan, J., Y Yang. et al., 2011. Structure of the Respiratory Syncytial Virus Fusion glycoprotein in the post-fusion conformation reveals preservation of neutralizing epitopes. J Virology. Epub. 1128/JVI00555-11.
6. Gomez, M., Mufson, M. et al. 2009. Phase-I study MEDI-534, of a live attenuated intranasal vaccine against respiratory syncytial virus and parainfluenza-3 virus in seropositive children. Ped Infect J. 28: 655-658.
7. Singh, S., Dennis, V. 2007. Immuogenicity and efficacy of recombinant RSV-F vaccine in a mouse model. Vaccine. 25: 6211-6223.
8. Kim, S., J Jang., et al., 2010. Single mucosal immunization of recombinant adenovirus-based vaccine expressing F1 protein fragment induces protective mucosal immunity against respiratory syncytial virus infection. Vaccine. 28: 3801-3808.
9. Nallet, S., Amacker, M. et al. 2009. Respiratory Syncytial Virus subunit vaccine based on a recombinant fusion protein expressed transiently in mammalian cells. 27: 6415-6419.
10. Huang K., Lawlor, H. 2010. Recombinant respiratory syncytial virus F protein expression is hindered by inefficient nuclear export and mRNA processing. Virus Genes. 40: 212-221.
11. Langley, J., Sales V., et al. 2009. A dose ranging study of a subunit Respiratory Syncytial Virus subtype A vaccine with and without aluminum phosphate adjuvantation in adults 65 years of age. Vaccine. 27: 5913-5919.
12. Herlocher et al. 1999 Immunological properties of plaque purified strains of live attenuated respiratory syncytial virus (RSV) for human vaccine. Vaccine, 17(2): 172-81.

13. Lukacs et al. 2006 Differential immune responses and pulmonary pathophysiology are induced by two different strains of respiratory syncytial virus. Am J Pathol 169(3): 977-86.

We claim:

1. A vaccine composition comprising a purified human respiratory syncytial virus (RSV) strain L19 (RSV-L19) and a nanoemulsion adjuvant, wherein the nanoemulsion adjuvant inactivates the RSV virus, and wherein the nanoemulsion adjuvant comprises:

(a) droplets having an average diameter of less than about 1000 nm;

(b) an aqueous phase;

(c) about 1% to about 80% of at least one cosmetically or pharmaceutically acceptable oil;

(d) about 0.001% to about 10% of at least one surfactant, wherein the surfactant is a polyoxyethylene nonionic surfactant, a cationic quaternary ammonium compound, or a combination thereof; and (e) about 0.1% to about 50% of at least one organic solvent, wherein the organic solvent is an alcohol.

2. The vaccine composition of claim 1, wherein cells infected in culture with the purified human RSV-L19 virus produce a greater amount of Fusion (F) and Glycoprotein (G) structural proteins associated with the viral particles as compared to cells infected with a human RSV strain A2.

3. The vaccine composition of claim 1, wherein the purified human RSV-L19 virus is attenuated.

4. The vaccine composition of claim 1, wherein the purified RSV-L19 virus comprises a human respiratory syncytial virus deposited with the American Type Culture Collection (ATCC) as HRSV-L19.

5. The vaccine composition of claim 1, wherein the vaccine composition is administered parenterally, orally or intranasally.

6. The vaccine composition of claim 5, wherein the parenteral administration is by subcutaneous, intraperitoneal or intramuscular injection.

7. The vaccine composition of claim 1, wherein the nanoemulsion adjuvant and/or the vaccine composition:

(a) is not systemically toxic to the subject; and/or (b) produces minimal or no inflammation upon administration.

8. The vaccine composition of claim 1, wherein the nanoemulsion adjuvant comprises droplets having an average diameter selected from the group consisting of less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, greater than about 50 nm, greater than about 70 nm, greater than about 125 nm, greater than about 125 nm and less than about 600 nm, and any combination thereof.

9. The vaccine composition of claim 1, wherein administration of the vaccine composition to a subject results in seroconversion of the subject after a single administration of the vaccine composition.

10. The vaccine composition of claim 1, wherein the alcohol:

(a) is selected from the group consisting of a $C_1$-$C_{12}$ alcohol, diol, triol, and combinations thereof;

(b) is selected from the group consisting of a nonpolar solvent, a polar solvent, a protic solvent, an aprotic solvent, semi-synthetic derivatives thereof, and combinations thereof;

(c) is selected from the group consisting of ethanol, methanol, isopropyl alcohol, glycerol, n-butanol, butylene glycol, perfumers alcohols, isopropanol, n-propanol, propylene glycols, glycerol, sorbitol, and any combination thereof; or (d) is any combination of (a), (b), and/or (c).

11. The vaccine composition of claim 1, wherein the oil is selected from the group consisting of animal oil, vegetable oil, natural oil, synthetic oil, hydrocarbon oils, silicone oils, and semi-synthetic derivatives there.

12. The vaccine composition of claim 1, wherein:

(a) the nonionic polyoxyethylene surfactant is selected from the group consisting of polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, semi-synthetic derivatives thereof, and mixtures thereof;

(b) the cationic quaternary ammonium compound is selected from the group consisting of an alkyl trimethyl ammonium chloride compound, a dialkyl dimethyl ammonium chloride compound, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Cetylpyridinium chloride, Dimethyldioctadecylammonium bromide, Dodecylethyldimethylammonium bromide, Dodecyltrimethylammonium bromide, Ethylhexadecyldimethylammonium bromide, Girard's reagent T, Hexadecyltrimethylammonium bromide, N,N',N'-Polyoxyethylene(10)-N-tallow-1,3-diaminopropane, Thonzonium bromide, Trimethyl(tetradecyl)ammonium bromide, 1,3,5-Triazine-1,3,5(2H,4H,6H)-triethanol, 1-Decanaminium, N-decyl-N, N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy) ethoxy)ethyl dimethyl benzyl ammonium chloride, Alkyl 1 or 3 benzyl-1-(2-hydroxethyl)-2-imidazolinium chloride, Alkyl bis(2-hydroxyethyl) benzyl ammonium chloride, Alkyl demethyl benzyl ammonium chloride, Alkyl dimethyl 3,4-dichlorobenzyl ammonium chloride (100% $C_{12}$), Alkyl dimethyl 3,4-dichlorobenzyl ammonium chloride (50% $C_{14}$, 40% $C_{12}$, 10% $C_{16}$), Alkyl dimethyl 3,4-dichlorobenzyl ammonium chloride (55% $C_{14}$, 23% $C_{12}$, 20% $C_{16}$), Alkyl dimethyl benzyl ammonium chloride, Alkyl dimethyl benzyl ammonium chloride (100% $C_{14}$), Alkyl dimethyl benzyl ammonium chloride (100% C16), Alkyl dimethyl benzyl ammonium chloride (41% $C_{14}$, 28% $C_{12}$), Alkyl dimethyl benzyl ammonium chloride (47% $C_{12}$, 18% $C_{14}$), Alkyl dimethyl benzyl ammonium chloride (55% $C_{16}$, 20% $C_{14}$), Alkyl dimethyl benzyl ammonium chloride (58% $C_{14}$, 28% $C_{16}$), Alkyl dimethyl benzyl ammonium chloride (60% $C_{14}$, 25% $C_{12}$), Alkyl dimethyl benzyl ammonium chloride (61% $C_{11}$, 23% $C_{14}$), Alkyl dimethyl benzyl ammonium chloride (61% $C_{12}$, 23% $C_{14}$), Alkyl dimethyl benzyl ammonium chloride (65% $C_{12}$, 25% $C_{14}$), Alkyl dimethyl benzyl ammonium chloride (67% $C_{12}$, 24% $C_{14}$), Alkyl dimethyl benzyl ammonium chloride (67% $C_{12}$, 25% $C_{14}$), Alkyl dimethyl benzyl ammonium chloride (90% $C_{14}$, 5% $C_{12}$), Alkyl dimethyl benzyl ammonium chloride (93% $C_{14}$, 4% $C_{12}$), Alkyl dimethyl benzyl ammonium chloride (95% $C_{16}$, 5% $C_{18}$), Alkyl didecyl dimethyl ammonium chloride, Alkyl dimethyl benzyl ammonium chloride ($C_{12-16}$), Alkyl dimethyl benzyl ammonium chloride ($C_{12-18}$), dialkyl dimethyl benzyl ammonium chloride, Alkyl dimethyl dimethybenzyl ammonium chloride, Alkyl dimethyl ethyl ammonium bromide (90% $C_{14}$, 5% $C_{16}$, 5% $C_{12}$), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% $C_{14}$), Alkyl dimethyl isopropylbenzyl ammonium chloride (50% $C_{12}$, 30% $C_{14}$, 17% $C_{16}$, 3% $C_{18}$), Alkyl trimethyl ammonium chloride (58% $C_{18}$, 40% $C_{16}$, 1% $C_{14}$, 1% $C_{12}$), Alkyl trimethyl ammonium chloride (90% $C_{18}$, 10% $C_{16}$), Alkyldimethyl(ethylbenzyl) ammonium chloride ($C_{12-18}$), Di-($C_{8-10}$)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis(2-hydroxyethyl) octyl hydrogen ammonium chloride, Dodecyl dimethyl benzyl ammonium chloride, Dodecylcarbamoyl methyl dinethyl benzyl ammonium chloride, Heptadecyl hydroxyethylimidazolinium chloride, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis (alkyl dimethyl ammonium chloride), Trimethoxysily propyl dimethyl octadecyl ammonium chloride, Trimethoxysilyl quats, Trimethyl dodecylbenzyl ammonium chloride, semi-synthetic derivatives thereof, and combinations thereof; or (d) any combination of (a)-(c) thereof.

13. The vaccine composition of claim 1, wherein:
(a) the nanoemulsion comprises at least one cationic surfactant and at least one polyoxyethylene nonionic surfactant;
(b) the nanoemulsion comprises at least one cationic surfactant and at least one polyoxyethylene nonionic surfactant which is polysorbate 20, polysorbate 80, poloxamer 188, poloxamer 407, or a combination thereof;
(c) the nanoemulsion comprises at least one cationic surfactant and at least one polyoxyethylene nonionic surfactant which is polysorbate 20, polysorbate 80, poloxamer 188, poloxamer 407, or a combination thereof, and wherein the polyoxyethylene nonionic surfactant is present at about 0.01% to about 5.0%, or at about 0.1% to about 3%;
(d) the nanoemulsion comprises at least one cationic surfactant and at least one polyoxyethylene nonionic surfactant, and the non-ionic surfactant is present in a concentration of about 0.05% to about 10%, about 0.05% to about 7.0%, about 0.1% to about 7%, or about 0.5% to about 4%;
(e) the nanoemulsion comprises at least one cationic surfactant and at least one polyoxyethylene nonionic surfactant, wherein the cationic surfactant is present in a concentration of about 0.05% to about 2% or about 0.01% to about 2%; or
(f)(0 any combination of (a)-(f).

14. The vaccine composition of claim 1, further comprising chitosan.

15. The vaccine composition of claim 1, further comprising glucan.

16. The vaccine composition of claim 1, wherein the aqueous phase is present in Phosphate Buffered Saline (PBS).

17. A method for inducing an enhanced immunity against disease caused by human respiratory syncytial virus comprising the step of administering to a subject an effective amount of the vaccine composition of claim 1.

18. The method of claim 17, wherein the subject produces a protective immune response after at least a single administration of the vaccine composition.

19. The method of claim 18, wherein the immune response is protective against one or more strains of RSV.

20. A method for enhancing immunity to human respiratory syncytial virus infections comprising administering to the subject the vaccine composition of claim 1.

21. The method of claim 20, wherein the administering comprises intranasal administration.

22. The vaccine composition of claim 8, wherein the nanoemulsion adjuvant comprises droplets having an average diameter of less than about 800 nm.

23. The vaccine composition of claim 8, wherein the nanoemulsion adjuvant comprises droplets having an average diameter of less than about 600 nm.

24. The vaccine composition of claim 8, wherein the nanoemulsion adjuvant comprises droplets having an average diameter of less than about 500 nm.

25. The vaccine composition of claim 8, wherein the nanoemulsion adjuvant comprises droplets having an average diameter of less than about 400 nm.

* * * * *